US009404148B2

(12) United States Patent
Gale et al.

(10) Patent No.: US 9,404,148 B2

(45) Date of Patent: Aug. 2, 2016

(54) OLIGONUCLEOTIDES AND USES THEREOF

(75) Inventors: Nittaya Gale, Southampton (GB); Paul Debenham, Middlesex (GB); David John French, Middlesex (GB); Rebecca Howard, Middlesex (GB); David Gordon McDowell, Middlesex (GB); Tom Brown, Southampton (GB)

(73) Assignee: LGC Limited (GB)

( * ) Notice: Subject to any disclaimer, the term of this patent is extended or adjusted under 35 U.S.C. 154(b) by 358 days.

(21) Appl. No.: 12/738,977

(22) PCT Filed: Oct. 21, 2008

(86) PCT No.: PCT/GB2008/003555

§ 371 (c)(1), (2), (4) Date: Jul. 14, 2010

(87) PCT Pub. No.: WO2009/053679

PCT Pub. Date: Apr. 30, 2009

(65) Prior Publication Data

US 2011/0003290 A1 Jan. 6, 2011

(30) Foreign Application Priority Data

Oct. 22, 2007 (GB) .................................. 0720675.8
Aug. 19, 2008 (GB) .................................. 0815113.6

(51) Int. Cl.

| | |
|---|---|
| ***C12Q 1/68*** | (2006.01) |
| ***C12P 19/34*** | (2006.01) |
| ***C07H 21/02*** | (2006.01) |
| ***C07H 21/04*** | (2006.01) |
| ***C07H 21/00*** | (2006.01) |

(52) U.S. Cl.

CPC .................................. *C12Q 1/6827* (2013.01)

(58) Field of Classification Search

USPC ............. 435/6.1, 6.11, 6.12, 91.1, 91.2, 183, 435/283.1, 287.1, 287.2; 436/94, 501; 536/23.1, 24.3, 24.33, 25.3

See application file for complete search history.

(56) References Cited

U.S. PATENT DOCUMENTS

| | | | | |
|---|---|---|---|---|
| 5,804,375 | A | 9/1998 | Gelfand et al. | |
| 6,207,373 | B1 * | 3/2001 | Sosnowski et al. | 435/6.12 |
| 6,664,064 | B1 | 12/2003 | Dietmaier | |
| 2002/0137031 | A1 * | 9/2002 | Wolber | 435/6 |
| 2007/0192903 | A1 * | 8/2007 | Heck et al. | 800/285 |

FOREIGN PATENT DOCUMENTS

| | | | |
|---|---|---|---|
| EP | 1 748 083 | A1 | 1/2007 |
| WO | WO 99/43853 | | 9/1999 |
| WO | WO 01/73118 | A2 | 10/2001 |
| WO | WO 2005/113822 | A2 | 12/2005 |
| WO | WO 2007/010268 | A2 | 1/2007 |

OTHER PUBLICATIONS

International Search Report of the ISA/EPO for International Application PCT/GB2008/003555 mailed Jan. 28, 2009.

Written Opinion of the ISA/EPO for International Application PCT/GB2008/003555 mailed Jan. 28, 2009.

Demand for International Preliminary Examination of International Application PCT/GB2008/003555 filed with the IPEA/EPO Aug. 20, 2009.

Letter dated Aug. 20, 2009 to the IPEA/EPO on behalf of the Applicants for International Application PCT/GB2008/003555, with attachment.

Notification Concerning Informal Communications with the Applicant mailed by the IPEA/EPO on Nov. 6, 2009 for International Application PCT/GB2008/003555.

Letter dated Dec. 4, 2009 to the IPEA/EPO on behalf of the Applicants for International Application PCT/GB2008/003555, with attachments.

International Preliminary Report on Patentability of the IPEA/EPO for International Application PCT/GB2008/003555 dated Dec. 10, 2009.

Bart-Delabesse, E., Sarfati, J., Debeaupuis, J.P., van Leeuwen, W., van Belkum, A., Bretagne, S., Latge, J.P. (2001). Comparison of restriction fragment length polymorphism, microsatellite length polymorphism, and random amplification of polymorphic DNA analyses for fingerprinting Aspergillus fumigatus isolates. J. Clin. Microbiol. 39: 2683-6.

Belgrader, P., Smith, J.K., Weedn, V.W., Northrup, M.A. (1998). Rapid PCR for identity testing using a battery-powered miniature thermal cycler. J Forensic Sci. 43(2): 315-9.

Bell, G.I., Selby, M.J., Rutter, W.J. (1982). The highly polymorphic region near the human insulin gene is composed of simple tandemly repeating sequences. Nature 295: 31-5.

Brondani, C., Rangel, P.H., Borba, T.C,. Brondani, R.P. (2003). Transferability of microsatellite and sequence tagged site markers in *Oryza* species. Hereditas. 138(3): 187-92.

Carrier. L,, Hengstenberg. C,, Beckmann. J,S,, Guicheney. P., Dufour, C., Bercovici, J., Dausse, E., Berebbi-Bertrand, I., Wisnewsky, C., Pulvenis, D. et al (1993). Mapping of a novel gene for familial hypertrophic cardiomyopathy to chromosome 11. Nat. Genet. 4: 311-3.

Foulet et al (2005). Microsatellite marker analysis as a typing system for Candida glabrata. J. Clin. Microbiol. 43: 4574-4579.

Frayling, I. M. (1999). Microsatellite instability. Gut 45: 1-4.

Goedecke, N., McKenna, B., El-Difrawy, S., Carey, L., Matsudaira, P., Ehrlich D. (2004). A high-performance multilane microdevice system designed for the DNA forensics laboratory. Electrophoresis 25: 1678-86.

(Continued)

*Primary Examiner* — Frank Lu

(74) *Attorney, Agent, or Firm* — Geoffrey M. Karny

(57) ABSTRACT

A method for determining the number of tandem repeats in a target polynucleotide, the method comprising (a) providing a sample containing the target polynucleotide, wherein one or more of the tandem repeats in the target polynucleotide is in single stranded form, (b) hybridizing a labelled probe oligonucleotide to the single stranded portion of the target polynucleotide, wherein the probe oligonucleotide is complementary to at least one of the tandem repeats, and at least 5 nucleotides of the probe oligonucleotide are complementary to the tandem repeats, in the single stranded portion of the target polynucleotide, and (c) determining the number of tandem repeats in the target polynucleotide based on the hybridization of the probe oligonucleotide to the single stranded portion of the target polynucleotide.

23 Claims, 19 Drawing Sheets

(56) References Cited

OTHER PUBLICATIONS

Figure 1:
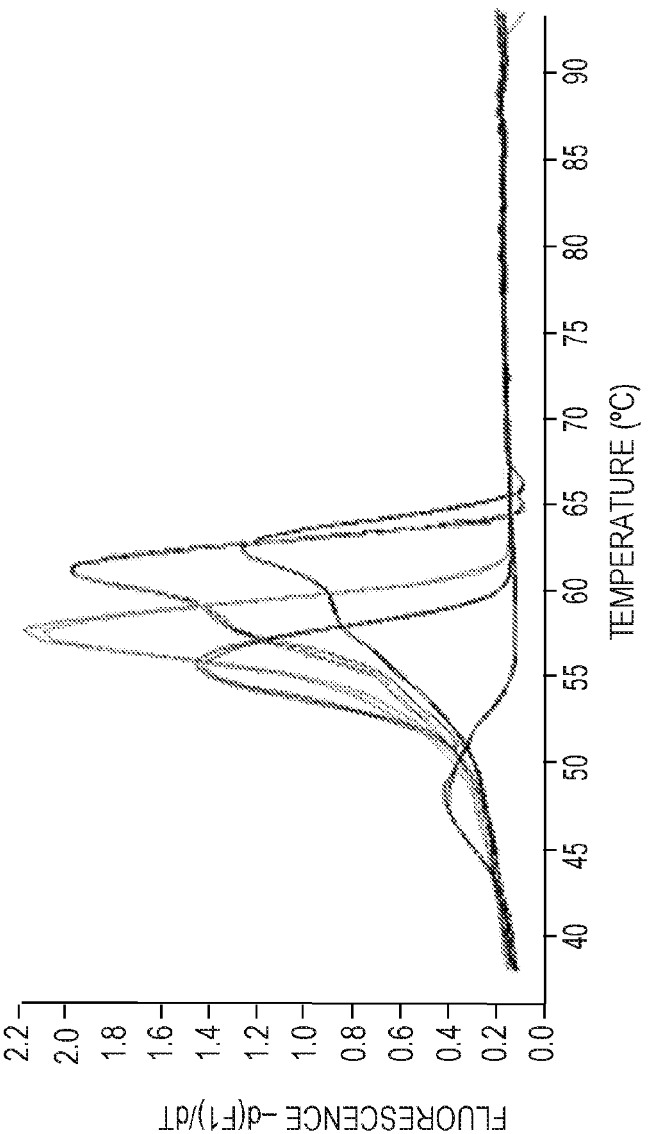

Hennequin (2001). Microsatellite typing as a new tool for identification of *Saccharomyces cerevisiae* strains. J. Clin. Microbiol. 39: 551-559.
Ionov, Y., Peinado, M.A., Malkhosyan, S., Shibata D., and Perucho. M. (1993). Ubiquitous somatic mutations in simple repeated sequences reveal a new mechanism for colonic carcinogenesis. Nature 363: 558-561.
Jeffreys AJ, Wilson V, Thein SL. (1985a). Nature 314: 67-73. Hypervariable 'minisatellite' regions in human DNA.
Jeffreys AJ, Wilson V, Thein SL. Nature. (1985b). 316: 76-9. Individual-specific 'fingerprints' of human DNA.
Lagally, E.T., Emrich, C.A., Mathies, R.A. (2001). Fully integrated PCR-capillary electrophoresis microsystem for DNA analysis. Lab Chip 1: 102-7.
Loeb, L. A. (1994). Microsatellite instability: marker of a mutator phenotype in cancer. Cancer Res. 54: 5059-5063.
Matute, D.R. Sepulveda, V.E., Quesada, L.M., Goldman, G.H., Taylor, J.W., Restrepo, A., McEwen, J.G. (2006). Microsatellite analysis of three phylogenetic species of *Paracoccidioides brasiliensis*. J. Clin. Microbiol. 44: 2153-7.
McCormick, R.M., Nelson, R.J., Alonso-Amigo, M.G., Benvegnu, D.J., Hooper, H.H. (1997). Microchannel electrophoretic separations of DNA in injection-molded plastic substrates. Anal. Chem. 69: 2626-30.
McCouch, S.R., Teytelman, L., Xu, Y., Lobos K.B., Clare K., Walton, M., Fu, B., Maghirang R., Li, Z., Xing, Y., Zhang, Q., Kono, I., Yano M., Fjellstrom, R., DeClerk, G., Schneider, D., Cartinhour, S., Ware, D. and Stein, L. (2002). Development and mapping of 2240 new SSR markers for rice (*Oryza sativa* L). DNA Res. 9: 199-207.
Radtkey, R., Feng, L., Muralhidar, M., Duhon, M., Canter, D., DiPierro, D., Fallon, S., Tu, E., McElfresh, K., Nerenberg, M., Sosnowski, R. (2000). Rapid, high fidelity analysis of simple sequence repeats on an electronically active DNA microchip. Nucleic Acids Res. 28: E17.
Restrepo-Moreno (2003). Paracoccidioidomycosis, p. 328-345. In W.E. Dismukes, P.G. Pappas, and J.D. Sobel (ed.), Clinical mycology. Oxford University Press, New York, N.Y.
Roder., M.S., Korzun, V., Wendehake, K., Plaschke, J., Tixier, M.H., Leroy, P., Ganal, M.W. (1998). Genetics 149: 2007-23. A microsatellite map of wheat.
Schmalzing, D., Koutny, L., Chisholm, D., Adourian, A., Matsudaira, P., Ehrlich, D. (1999). Two-color multiplexed analysis of eight short tandem repeat loci with an electrophoretic microdevice. Anal. Biochem. 270: 148-52.
Shi, Y., Simpson, P.C., Scherer, J.R., Wexler, D., Skibola, C., Smith, M.T., Mathies, R.A. (1999). Radial capillary array electrophoresis microplate and scanner for high-performance nucleic acid analysis. Anal Chem. 71: 5354-61.
Sinden, R.R. (1999). Biological implications of the DNA structures associated with disease-causing triplet repeats. Am. J. Hum. Genet. 64: 346-53.
Thierfelder, L., MacRae, C., Watkins, H., Tomfohrde, J., Williams, M., McKenna., W., Bohm K., Noeske, G., Schlepper, M., Bowcock, A. et al (1993). A familial hypertrophic cardiomyopathy locus maps to chromosome 15q2. Proc. Natl. Acad. Sci U S A. 90: 6270-4.
Watkins, H., MacRae, C., Thierfelder, L., Chou, Y.H., Frenneaux, M., McKenna, W., Seidman, J.G., Seidman, C.E. (1993). A disease locus for familial hypertrophic cardiomyopathy maps to chromosome 1q3. Nat. Genet. 3: 333-7.
Weissenbach, J., Gyapay, G., Dib, C., Vignal, A., Morissette, J., Millasseau, P., Vaysseix, G., Lathrop, M. (1992). A second-generation linkage map of the human genome. Nature 359: 794-801.
Westin, L. Xu, X., Miller, C., Wang, L., Edman, C.F., Nerenberg, M. (2000). Anchored multiplex amplification on a microelectronic chip array. Nature Biotechnol. 18: 199-204.
Wooley, A.T. and Mathies, R.A. (1994). Proc. Natl. Acad. Sci. USA 91: 11348-11352.
Butler (2007) Biotechniques: ii-v, Supplement to vol. 43.
French et al (2008) Forensic Science International : Genetics 2, 333-339.
Gale et al (2008) Organic & Biomolecular Chemistry 6, 4553-4559.
Corbett Life Science web page 2007. High Resolution Melt.

* cited by examiner

```
1    atggctgccc tcacggctgc accgggagga tgactgtntt cccactctca gtcctgccga
61   ggtgcctgac agccctgcac ccaggagctg gggggtctaa gagcttgtaa aaagtgtaca
121  agtgccagat gctcgttgtg cacaaatcta aatgcagaaa agcactgaaa gaagaatcca
181  gaaaaccaca gttcccattt ttatatggga gcaaacaaag gcagatccca agctcttcct
241  cttccctaga tcaatacaga cagacagaca ggtggataga tagatagata gatagataga
301  tagatagata gatagatatc attgaaagac aaaacagaga tggatgatag atacatgctt
361  acagatgcac acacaaacgt aaatggtatn aaaaatngga tncactcttg tanggttgtt
```

FIG. 4

```
1     CCAGCCTGGC CCACACAGTC CCCTGTACAC AGGGCTTCCG AGTGCAGGTC
51    ACAGGGAACA CAGACTCCAT GGTGAATGAA TGAATGAATG AATGAATGAA
101   TGAGGGAAAT AAGGGAGGAA CAGGCCAATG GGAATCACCC CAGAGCCCAG
151   ATACCCTTTG AATTTTGCCC CCTATTTGCC CAGGACCCCC CACCATGAGC
201   TGCTGCTAGA GCCTGGGAAG GGCCTTGGGG CTGCCTCCC
```

FIG. 13

SEQUENCE LISTING

```
<160> NUMBER OF SEQ ID NOS: 71

<210> SEQ ID NO 1
<211> LENGTH: 16
<212> TYPE: DNA
<213> ORGANISM: Artificial Sequence
<220> FEATURE:
<223> OTHER INFORMATION: Short Tandem Repeat D251338

<400> SEQUENCE: 1

tgcctgcctt ccttcc                                                    16

<210> SEQ ID NO 2
<211> LENGTH: 40
<212> TYPE: DNA
<213> ORGANISM: Artificial Sequence
<220> FEATURE:
<223> OTHER INFORMATION: Short Tandem Repeat FGA

<400> SEQUENCE: 2

tttctttctt tcttttttct ctttctttct ccttccttcc                          40

<210> SEQ ID NO 3
<211> LENGTH: 60
<212> TYPE: DNA
<213> ORGANISM: Artificial Sequence
<220> FEATURE:
<223> OTHER INFORMATION: HYBSTR oligonucleotide probe
<220> FEATURE:
<221> NAME/KEY: modified_base
<222> LOCATION: (11) ... (11)
<223> OTHER INFORMATION: C6 FAM dU
<220> FEATURE:
<221> NAME/KEY: modified_base
<222> LOCATION: (19) ... (19)
<223> OTHER INFORMATION: C6 FAM dU
<220> FEATURE:
<221> NAME/KEY: misc_feature
<222> LOCATION: (60) ... (60)
<223> OTHER INFORMATION: 3 prime phosphate blocking group is located
      after this nucleotide

<400> SEQUENCE: 3

ggtggataga uagatagaua gatagataga tagatagata gatagataga tagatagata    60

<210> SEQ ID NO 4
<211> LENGTH: 48
<212> TYPE: DNA
<213> ORGANISM: Artificial Sequence
<220> FEATURE:
<223> OTHER INFORMATION: STRV2 oligonucleotide probe
<220> FEATURE:
<221> NAME/KEY: misc_feature
```

<222> LOCATION: (16) ... (16)
<223> OTHER INFORMATION: A hexaethylene glycol spacer is located after this nucleotide
<220> FEATURE:
<221> NAME/KEY: modified_base
<222> LOCATION: (23) ... (23)
<223> OTHER INFORMATION: C6 FAM dU
<220> FEATURE:
<221> NAME/KEY: modified_base
<222> LOCATION: (31) ... (31)
<223> OTHER INFORMATION: C6 FAM dU
<220> FEATURE:
<221> NAME/KEY: misc_feature
<222> LOCATION: (48) ... (48)
<223> OTHER INFORMATION: 3 prime phosphate blocking group is located after this nucleotide

<400> SEQUENCE: 4
ggtggataga tagatagata gauagataga uagatagata gatagata 48

<210> SEQ ID NO 5
<211> LENGTH: 64
<212> TYPE: DNA
<213> ORGANISM: Artificial Sequence
<220> FEATURE:
<223> OTHER INFORMATION: STRV3 oligonucleotide probe
<220> FEATURE:
<221> NAME/KEY: misc_feature
<222> LOCATION: (16) ... (16)
<223> OTHER INFORMATION: Two hexaethylene glycol spacers are located after this nucleotide
<220> FEATURE:
<221> NAME/KEY: modified_base
<222> LOCATION: (23) ... (23)
<223> OTHER INFORMATION: C6 FAM dU
<220> FEATURE:
<221> NAME/KEY: modified_base
<222> LOCATION: (31) ... (31)
<223> OTHER INFORMATION: C6 FAM dU
<220> FEATURE:
<221> NAME/KEY: misc_feature
<222> LOCATION: (64) ... (64)
<223> OTHER INFORMATION: 3 prime phosphate blocking group is located after this nucleotide

<400> SEQUENCE: 5
ggtggataga tagatagata gauagataga uagatagata gatagataga tagatagata 60
gata 64

<210> SEQ ID NO 6
<211> LENGTH: 24
<212> TYPE: DNA
<213> ORGANISM: Artificial Sequence
<220> FEATURE:
<223> OTHER INFORMATION: RC5 oligonucleotide target sequence

<400> SEQUENCE: 6
tatctatcta tctatctatc cacc 24

<210> SEQ ID NO 7
<211> LENGTH: 32
<212> TYPE: DNA
<213> ORGANISM: Artificial Sequence
<220> FEATURE:
<223> OTHER INFORMATION: RC7 oligonucleotide target sequence

<400> SEQUENCE: 7
tatctatcta tctatctatc tatctatcca cc 32

<210> SEQ ID NO 8

```
<211> LENGTH: 36
<212> TYPE: DNA
<213> ORGANISM: Artificial Sequence
<220> FEATURE:
<223> OTHER INFORMATION: RC8 oligonucleotide target sequence

<400> SEQUENCE: 8

tatctatcta tctatctatc tatctatcta tccacc                             36


<210> SEQ ID NO 9
<211> LENGTH: 44
<212> TYPE: DNA
<213> ORGANISM: Artificial Sequence
<220> FEATURE:
<223> OTHER INFORMATION: RC10 oligonucleotide target sequence

<400> SEQUENCE: 9

tatctatcta tctatctatc tatctatcta tctatctatc cacc                    44


<210> SEQ ID NO 10
<211> LENGTH: 48
<212> TYPE: DNA
<213> ORGANISM: Artificial Sequence
<220> FEATURE:
<223> OTHER INFORMATION: RC11 oligonucleotide target sequence

<400> SEQUENCE: 10

tatctatcta tctatctatc tatctatcta tctatctatc tatccacc                48


<210> SEQ ID NO 11
<211> LENGTH: 44
<212> TYPE: DNA
<213> ORGANISM: Artificial Sequence
<220> FEATURE:
<223> OTHER INFORMATION: RC10b oligonucleotide target sequence

<400> SEQUENCE: 11

tatctgtcta tctgtctatc tgtctatctg tctatctgtc cacc                    44


<210> SEQ ID NO 12
<211> LENGTH: 44
<212> TYPE: DNA
<213> ORGANISM: Artificial Sequence
<220> FEATURE:
<223> OTHER INFORMATION: RC10c oligonucleotide target sequence

<400> SEQUENCE: 12

tgtctgtctg tctgtctgtc tgtctgtctg tctgtctgtc cacc                    44


<210> SEQ ID NO 13
<211> LENGTH: 44
<212> TYPE: DNA
<213> ORGANISM: Artificial Sequence
<220> FEATURE:
<223> OTHER INFORMATION: RC10d oligonucleotide target sequence

<400> SEQUENCE: 13

tatctatcta tctatcccct tatctatcta tctatctatc cacc                    44


<210> SEQ ID NO 14
<211> LENGTH: 40
<212> TYPE: DNA
<213> ORGANISM: Artificial Sequence
<220> FEATURE:
<223> OTHER INFORMATION: RC10e oligonucleotide target sequence

<400> SEQUENCE: 14
```

-continued tatctatcta tctatctatc tatctatcta tctatctatc 40

<210> SEQ ID NO 15
<211> LENGTH: 48
<212> TYPE: DNA
<213> ORGANISM: Artificial Sequence
<220> FEATURE:
<223> OTHER INFORMATION: RC11b oligonucleotide target sequence

<400> SEQUENCE: 15
tatctgtcta tctgtctatc tgtctatctg tctatctgtc tatccacc 48

<210> SEQ ID NO 16
<211> LENGTH: 48
<212> TYPE: DNA
<213> ORGANISM: Artificial Sequence
<220> FEATURE:
<223> OTHER INFORMATION: RC11c oligonucleotide target sequence

<400> SEQUENCE: 16
tgtctgtctg tctgtctgtc tgtctgtctg tctgtctgtc tgtccacc 48

<210> SEQ ID NO 17
<211> LENGTH: 48
<212> TYPE: DNA
<213> ORGANISM: Artificial Sequence
<220> FEATURE:
<223> OTHER INFORMATION: RC11d oligonucleotide target sequence

<400> SEQUENCE: 17
tatctatcta tctatctatc cccttatcta tctatctatc tatccacc 48

<210> SEQ ID NO 18
<211> LENGTH: 44
<212> TYPE: DNA
<213> ORGANISM: Artificial Sequence
<220> FEATURE:
<223> OTHER INFORMATION: RC11e oligonucleotide target sequence

<400> SEQUENCE: 18
tatctatcta tctatctatc tatctatcta tctatctatc tatc 44

<210> SEQ ID NO 19
<211> LENGTH: 28
<212> TYPE: DNA
<213> ORGANISM: Artificial Sequence
<220> FEATURE:
<223> OTHER INFORMATION: STRF2 oligonucleotide primer

<400> SEQUENCE: 19
cagatcccaa gctcttcctc ttccctag 28

<210> SEQ ID NO 20
<211> LENGTH: 31
<212> TYPE: DNA
<213> ORGANISM: Artificial Sequence
<220> FEATURE:
<223> OTHER INFORMATION: STRR2 oligonucleotide primer

<400> SEQUENCE: 20
acgtttgtgt gtgcatctgt aagcatgtat c 31

<210> SEQ ID NO 21
<211> LENGTH: 70
<212> TYPE: DNA

<213> ORGANISM: Artificial Sequence
<220> FEATURE:
<223> OTHER INFORMATION: 02466R oligonucleotide probe
<220> FEATURE:
<221> NAME/KEY: modified_base
<222> LOCATION: (9) ... (9)
<223> OTHER INFORMATION: fluorescein dT
<220> FEATURE:
<221> NAME/KEY: modified_base
<222> LOCATION: (17) ... (17)
<223> OTHER INFORMATION: fluorescein dT
<220> FEATURE:
<221> NAME/KEY: modified_base
<222> LOCATION: (25) ... (25)
<223> OTHER INFORMATION: fluorescein dT
<220> FEATURE:
<221> NAME/KEY: modified_base
<222> LOCATION: (33) ... (33)
<223> OTHER INFORMATION: fluorescein dT
<220> FEATURE:
<221> NAME/KEY: modified_base
<222> LOCATION: (41) ... (41)
<223> OTHER INFORMATION: fluorescein dT
<220> FEATURE:
<221> NAME/KEY: modified_base
<222> LOCATION: (49) ... (49)
<223> OTHER INFORMATION: fluorescein dT

<400> SEQUENCE: 21
caatgatatc tatctatcta tctatctatc tatctatcta tctatctatc tatctatcta 60
tctatccacc 70

<210> SEQ ID NO 22
<211> LENGTH: 69
<212> TYPE: DNA
<213> ORGANISM: Artificial Sequence
<220> FEATURE:
<223> OTHER INFORMATION: 02467R oligonucleotide probe
<220> FEATURE:
<221> NAME/KEY: modified_base
<222> LOCATION: (9) ... (9)
<223> OTHER INFORMATION: fluorescein dT
<220> FEATURE:
<221> NAME/KEY: modified_base
<222> LOCATION: (17) ... (17)
<223> OTHER INFORMATION: fluorescein dT
<220> FEATURE:
<221> NAME/KEY: modified_base
<222> LOCATION: (25) ... (25)
<223> OTHER INFORMATION: fluorescein dT
<220> FEATURE:
<221> NAME/KEY: modified_base
<222> LOCATION: (33) ... (33)
<223> OTHER INFORMATION: fluorescein dT
<220> FEATURE:
<221> NAME/KEY: modified_base
<222> LOCATION: (41) ... (41)
<223> OTHER INFORMATION: fluorescein dT
<220> FEATURE:
<221> NAME/KEY: modified_base
<222> LOCATION: (49) ... (49)
<223> OTHER INFORMATION: fluorescein dT
<220> FEATURE:
<221> NAME/KEY: misc_feature
<222> LOCATION: (50) ... (50)
<223> OTHER INFORMATION: An abasic residue is located after this nucleotide

<400> SEQUENCE: 22
caatgatatc tatctatcta tctatctatc tatctatcta tctatctatc atctatctat 60
ctatccacc 69

<210> SEQ ID NO 23

-continued

<211> LENGTH: 64
<212> TYPE: DNA
<213> ORGANISM: Artificial Sequence
<220> FEATURE:
<223> OTHER INFORMATION: 02468R oligonucleotide probe
<220> FEATURE:
<221> NAME/KEY: modified_base
<222> LOCATION: (3) ... (3)
<223> OTHER INFORMATION: fluorescein dT
<220> FEATURE:
<221> NAME/KEY: modified_base
<222> LOCATION: (11) ... (11)
<223> OTHER INFORMATION: fluorescein dT
<220> FEATURE:
<221> NAME/KEY: modified_base
<222> LOCATION: (19) ... (19)
<223> OTHER INFORMATION: fluorescein dT
<220> FEATURE:
<221> NAME/KEY: modified_base
<222> LOCATION: (27) ... (27)
<223> OTHER INFORMATION: fluorescein dT
<220> FEATURE:
<221> NAME/KEY: modified_base
<222> LOCATION: (35) ... (35)
<223> OTHER INFORMATION: fluorescein dT

<400> SEQUENCE: 23
tatctatcta tctatctatc tatctatcta tctatctatc tatctatcta tctatctatc 60
cacc 64

<210> SEQ ID NO 24
<211> LENGTH: 63
<212> TYPE: DNA
<213> ORGANISM: Artificial Sequence
<220> FEATURE:
<223> OTHER INFORMATION: 02469R oligonucleotide probe
<220> FEATURE:
<221> NAME/KEY: modified_base
<222> LOCATION: (3) ... (3)
<223> OTHER INFORMATION: fluorescein dT
<220> FEATURE:
<221> NAME/KEY: modified_base
<222> LOCATION: (11) ... (11)
<223> OTHER INFORMATION: fluorescein dT
<220> FEATURE:
<221> NAME/KEY: modified_base
<222> LOCATION: (19) ... (19)
<223> OTHER INFORMATION: fluorescein dT
<220> FEATURE:
<221> NAME/KEY: modified_base
<222> LOCATION: (27) ... (27)
<223> OTHER INFORMATION: fluorescein dT
<220> FEATURE:
<221> NAME/KEY: modified_base
<222> LOCATION: (35) ... (35)
<223> OTHER INFORMATION: fluorescein dT
<220> FEATURE:
<221> NAME/KEY: misc_feature
<222> LOCATION: (40) ... (40)
<223> OTHER INFORMATION: An abasic residue is located after this nucleotide

<400> SEQUENCE: 24
tatctatcta tctatctatc tatctatcta tctatctatc atctatctat ctatctatcc 60
acc 63

<210> SEQ ID NO 25
<211> LENGTH: 61
<212> TYPE: DNA
<213> ORGANISM: Artificial Sequence
<220> FEATURE:
<223> OTHER INFORMATION: C5 oligonucleotide target sequence

<400> SEQUENCE: 25
ccctagatca atacagacag acagacaggt ggatagatag atagatagat atcattgaaa 60
g 61

<210> SEQ ID NO 26
<211> LENGTH: 69
<212> TYPE: DNA
<213> ORGANISM: Artificial Sequence
<220> FEATURE:
<223> OTHER INFORMATION: C7 oligonucleotide target sequence

<400> SEQUENCE: 26
ccctagatca atacagacag acagacaggt ggatagatag atagatagat agatagatat 60
cattgaaag 69

<210> SEQ ID NO 27
<211> LENGTH: 73
<212> TYPE: DNA
<213> ORGANISM: Artificial Sequence
<220> FEATURE:
<223> OTHER INFORMATION: C8 oligonucleotide target sequence

<400> SEQUENCE: 27
ccctagatca atacagacag acagacaggt ggatagatag atagatagat agatagatag 60
atatcattga aag 73

<210> SEQ ID NO 28
<211> LENGTH: 77
<212> TYPE: DNA
<213> ORGANISM: Artificial Sequence
<220> FEATURE:
<223> OTHER INFORMATION: C9 oligonucleotide target sequence

<400> SEQUENCE: 28
ccctagatca atacagacag acagacaggt ggatagatag atagatagat agatagatag 60
atagatatca ttgaaag 77

<210> SEQ ID NO 29
<211> LENGTH: 81
<212> TYPE: DNA
<213> ORGANISM: Artificial Sequence
<220> FEATURE:
<223> OTHER INFORMATION: C10 oligonucleotide target sequence

<400> SEQUENCE: 29
ccctagatca atacagacag acagacaggt ggatagatag atagatagat agatagatag 60
atagatagat atcattgaaa g 81

<210> SEQ ID NO 30
<211> LENGTH: 85
<212> TYPE: DNA
<213> ORGANISM: Artificial Sequence
<220> FEATURE:
<223> OTHER INFORMATION: C11 oligonucleotide target sequence

<400> SEQUENCE: 30
ccctagatca atacagacag acagacaggt ggatagatag atagatagat agatagatag 60
atagatagat agatatcatt gaaag 85

<210> SEQ ID NO 31
<211> LENGTH: 89

<212> TYPE: DNA
<213> ORGANISM: Artificial Sequence
<220> FEATURE:
<223> OTHER INFORMATION: C12 oligonucleotide target sequence

<400> SEQUENCE: 31
ccctagatca atacagacag acagacaggt ggatagatag atagatagat agatagatag 60
atagatagat agatagatat cattgaaag 89

<210> SEQ ID NO 32
<211> LENGTH: 93
<212> TYPE: DNA
<213> ORGANISM: Artificial Sequence
<220> FEATURE:
<223> OTHER INFORMATION: C13 oligonucleotide target sequence

<400> SEQUENCE: 32
ccctagatca atacagacag acagacaggt ggatagatag atagatagat agatagatag 60
atagatagat agatagatag atatcattga aag 93

<210> SEQ ID NO 33
<211> LENGTH: 97
<212> TYPE: DNA
<213> ORGANISM: Artificial Sequence
<220> FEATURE:
<223> OTHER INFORMATION: C14 oligonucleotide target sequence

<400> SEQUENCE: 33
ccctagatca atacagacag acagacaggt ggatagatag atagatagat agatagatag 60
atagatagat agatagatag atagatatca ttgaaag 97

<210> SEQ ID NO 34
<211> LENGTH: 101
<212> TYPE: DNA
<213> ORGANISM: Artificial Sequence
<220> FEATURE:
<223> OTHER INFORMATION: C15 oligonucleotide target sequence

<400> SEQUENCE: 34
ccctagatca atacagacag acagacaggt ggatagatag atagatagat agatagatag 60
atagatagat agatagatag atagatagat atcattgaaa g 101

<210> SEQ ID NO 35
<211> LENGTH: 51
<212> TYPE: DNA
<213> ORGANISM: Artificial Sequence
<220> FEATURE:
<223> OTHER INFORMATION: B1 oligonucleotide probe
<220> FEATURE:
<221> NAME/KEY: misc_feature
<222> LOCATION: (51) ... (51)
<223> OTHER INFORMATION: 3 prime phosphate blocking group is located
after this nucleotide

<400> SEQUENCE: 35
tatctatcta tctatctatc cacctgtctg tctgtctgta ttgatctagg g 51

<210> SEQ ID NO 36
<211> LENGTH: 40
<212> TYPE: DNA
<213> ORGANISM: Artificial Sequence
<220> FEATURE:
<223> OTHER INFORMATION: FL1 oligonucleotide probe
<220> FEATURE:
<221> NAME/KEY: modified_base
<222> LOCATION: (1) ... (1)
<223> OTHER INFORMATION: fluorescein dT
<220> FEATURE:
<221> NAME/KEY: modified_base
<222> LOCATION: (9) ... (9)
<223> OTHER INFORMATION: fluorescein dT
<220> FEATURE:
<221> NAME/KEY: modified_base
<222> LOCATION: (17) ... (17)
<223> OTHER INFORMATION: fluorescein dT
<220> FEATURE:
<221> NAME/KEY: modified_base
<222> LOCATION: (25) ... (25)
<223> OTHER INFORMATION: fluorescein dT
<220> FEATURE:
<221> NAME/KEY: modified_base
<222> LOCATION: (33) ... (33)
<223> OTHER INFORMATION: fluorescein dT
<220> FEATURE:
<221> NAME/KEY: misc_feature
<222> LOCATION: (40) ... (40)
<223> OTHER INFORMATION: octanediol blocking group is located after this nucleotide

<400> SEQUENCE: 36
tatctatcta tctatctatc tatctatcta tctatctatc 40

<210> SEQ ID NO 37
<211> LENGTH: 50
<212> TYPE: DNA
<213> ORGANISM: Artificial Sequence
<220> FEATURE:
<223> OTHER INFORMATION: BP1 oligonucleotide probe
<220> FEATURE:
<221> NAME/KEY: misc_feature
<222> LOCATION: (30) ... (30)
<223> OTHER INFORMATION: A hexaethylene glycol spacer is located after this nucleotide

<400> SEQUENCE: 37
tatctatcta tctatctatc cacctgtctg gatcccaagc tcttcctctt 50

<210> SEQ ID NO 38
<211> LENGTH: 46
<212> TYPE: DNA
<213> ORGANISM: Artificial Sequence
<220> FEATURE:
<223> OTHER INFORMATION: FL1 oligonucleotide probe
<220> FEATURE:
<221> NAME/KEY: modified_base
<222> LOCATION: (7) ... (7)
<223> OTHER INFORMATION: fluorescein dT
<220> FEATURE:
<221> NAME/KEY: modified_base
<222> LOCATION: (15) ... (15)
<223> OTHER INFORMATION: fluorescein dT
<220> FEATURE:
<221> NAME/KEY: modified_base
<222> LOCATION: (23) ... (23)
<223> OTHER INFORMATION: fluorescein dT
<220> FEATURE:
<221> NAME/KEY: modified_base
<222> LOCATION: (31) ... (31)
<223> OTHER INFORMATION: fluorescein dT
<220> FEATURE:
<221> NAME/KEY: modified_base
<222> LOCATION: (39) ... (39)
<223> OTHER INFORMATION: fluorescein dT
<220> FEATURE:
<221> NAME/KEY: misc_feature
<222> LOCATION: (46) ... (46)
<223> OTHER INFORMATION: octanediol blocking group is located after this nucleotide

<400> SEQUENCE: 38
caatgatatc tatctatcta tctatctatc tatctatcta tctatc 46

<210> SEQ ID NO 39
<211> LENGTH: 46
<212> TYPE: DNA
<213> ORGANISM: Artificial Sequence
<220> FEATURE:
<223> OTHER INFORMATION: FL2 oligonucleotide probe
<220> FEATURE:
<221> NAME/KEY: modified_base
<222> LOCATION: (11) ... (11)
<223> OTHER INFORMATION: fluorescein dT
<220> FEATURE:
<221> NAME/KEY: modified_base
<222> LOCATION: (19) ... (19)
<223> OTHER INFORMATION: fluorescein dT
<220> FEATURE:
<221> NAME/KEY: modified_base
<222> LOCATION: (39) ... (39)
<223> OTHER INFORMATION: fluorescein dT
<220> FEATURE:
<221> NAME/KEY: misc_feature
<222> LOCATION: (46) ... (46)
<223> OTHER INFORMATION: 3 prime phosphate blocking group is located after this nucleotide

<400> SEQUENCE: 39
caatgatatc tatctatcta tctatctatc tatctatcta tctatc 46

<210> SEQ ID NO 40
<211> LENGTH: 46
<212> TYPE: DNA
<213> ORGANISM: Artificial Sequence
<220> FEATURE:
<223> OTHER INFORMATION: FL3 oligonucleotide probe
<220> FEATURE:
<221> NAME/KEY: modified_base
<222> LOCATION: (7) ... (7)
<223> OTHER INFORMATION: fluorescein dT
<220> FEATURE:
<221> NAME/KEY: modified_base
<222> LOCATION: (13) ... (13)
<223> OTHER INFORMATION: fluorescein dT
<220> FEATURE:
<221> NAME/KEY: modified_base
<222> LOCATION: (19) ... (19)
<223> OTHER INFORMATION: fluorescein dT
<220> FEATURE:
<221> NAME/KEY: modified_base
<222> LOCATION: (25) ... (25)
<223> OTHER INFORMATION: fluorescein dT
<220> FEATURE:
<221> NAME/KEY: modified_base
<222> LOCATION: (31) ... (31)
<223> OTHER INFORMATION: fluorescein dT
<220> FEATURE:
<221> NAME/KEY: modified_base
<222> LOCATION: (37) ... (37)
<223> OTHER INFORMATION: fluorescein dT
<220> FEATURE:
<221> NAME/KEY: modified_base
<222> LOCATION: (43) ... (43)
<223> OTHER INFORMATION: fluorescein dT
<220> FEATURE:
<221> NAME/KEY: misc_feature
<222> LOCATION: (46) ... (46)
<223> OTHER INFORMATION: 3 prime phosphate blocking group is located after this nucleotide

<400> SEQUENCE: 40
caatgatatc tatctatcta tctatctatc tatctatcta tctatc 46

<210> SEQ ID NO 41

-continued

```
<211> LENGTH: 46
<212> TYPE: DNA
<213> ORGANISM: Artificial Sequence
<220> FEATURE:
<223> OTHER INFORMATION: FL4 oligonucleotide probe
<220> FEATURE:
<221> NAME/KEY: modified_base
<222> LOCATION: (11) ... (11)
<223> OTHER INFORMATION: fluorescein dT
<220> FEATURE:
<221> NAME/KEY: modified_base
<222> LOCATION: (17) ... (17)
<223> OTHER INFORMATION: fluorescein dT
<220> FEATURE:
<221> NAME/KEY: modified_base
<222> LOCATION: (39) ... (39)
<223> OTHER INFORMATION: fluorescein dT
<220> FEATURE:
<221> NAME/KEY: misc_feature
<222> LOCATION: (46) ... (46)
<223> OTHER INFORMATION: 3 prime phosphate blocking group is located
      after this nucleotide

<400> SEQUENCE: 41

caatgatatc tatctatcta tctatctatc tatctatcta tctatc                    46


<210> SEQ ID NO 42
<211> LENGTH: 46
<212> TYPE: DNA
<213> ORGANISM: Artificial Sequence
<220> FEATURE:
<223> OTHER INFORMATION: FL5 oligonucleotide probe
<220> FEATURE:
<221> NAME/KEY: modified_base
<222> LOCATION: (13) ... (13)
<223> OTHER INFORMATION: fluorescein dT
<220> FEATURE:
<221> NAME/KEY: modified_base
<222> LOCATION: (21) ... (21)
<223> OTHER INFORMATION: fluorescein dT
<220> FEATURE:
<221> NAME/KEY: modified_base
<222> LOCATION: (29) ... (29)
<223> OTHER INFORMATION: fluorescein dT
<220> FEATURE:
<221> NAME/KEY: modified_base
<222> LOCATION: (37) ... (37)
<223> OTHER INFORMATION: fluorescein dT
<220> FEATURE:
<221> NAME/KEY: misc_feature
<222> LOCATION: (46) ... (46)
<223> OTHER INFORMATION: octanediol blocking group is located after this
      nucleotide

<400> SEQUENCE: 42

caatgatatc tatctatcta tctatctatc tatctatcta tctatc                    46


<210> SEQ ID NO 43
<211> LENGTH: 65
<212> TYPE: DNA
<213> ORGANISM: Artificial Sequence
<220> FEATURE:
<223> OTHER INFORMATION: 5LSB1 blocker oligonucleotide sequence
<220> FEATURE:
<221> NAME/KEY: misc_feature
<222> LOCATION: (45) ... (45)
<223> OTHER INFORMATION: A hexaethylene glycol spacer is located after
      this nucleotide

<400> SEQUENCE: 43

gcggctatct atctatctat ctatccacct gtctgtctgt ctgtagatcc caagctcttc     60

ctctt                                                                 65
```

<210> SEQ ID NO 44
<211> LENGTH: 64
<212> TYPE: DNA
<213> ORGANISM: Artificial Sequence
<220> FEATURE:
<223> OTHER INFORMATION: 7LSB2 blocker oligonucleotide sequence
<220> FEATURE:
<221> NAME/KEY: misc_feature
<222> LOCATION: (64) ... (64)
<223> OTHER INFORMATION: 3 prime phosphate blocking group is located after this nucleotide

<400> SEQUENCE: 44
gcggctatct atctatctat ctatctatct atccacctgt ctgtctgtct gtattgatct 60
aggg 64

<210> SEQ ID NO 45
<211> LENGTH: 45
<212> TYPE: DNA
<213> ORGANISM: Artificial Sequence
<220> FEATURE:
<223> OTHER INFORMATION: 10SFL1 blocker oligonucleotide sequence
<220> FEATURE:
<221> NAME/KEY: modified_base
<222> LOCATION: (11) ... (11)
<223> OTHER INFORMATION: fluorescein dT
<220> FEATURE:
<221> NAME/KEY: modified_base
<222> LOCATION: (12) ... (12)
<223> OTHER INFORMATION: pyrrolo-deoxycytosine
<220> FEATURE:
<221> NAME/KEY: modified_base
<222> LOCATION: (23) ... (23)
<223> OTHER INFORMATION: fluorescein dT
<220> FEATURE:
<221> NAME/KEY: modified_base
<222> LOCATION: (24) ... (24)
<223> OTHER INFORMATION: pyrrolo-deoxycytosine
<220> FEATURE:
<221> NAME/KEY: modified_base
<222> LOCATION: (32) ... (32)
<223> OTHER INFORMATION: pyrrolo-deoxycytosine
<220> FEATURE:
<221> NAME/KEY: modified_base
<222> LOCATION: (33) ... (33)
<223> OTHER INFORMATION: fluorescein dT
<220> FEATURE:
<221> NAME/KEY: misc_feature
<222> LOCATION: (45) ... (45)
<223> OTHER INFORMATION: 3 prime phosphate blocking group is located after this nucleotide

<400> SEQUENCE: 45
tatctatcta tctatctatc tatctatcta tctatctatc gccgc 45

<210> SEQ ID NO 46
<211> LENGTH: 37
<212> TYPE: DNA
<213> ORGANISM: Artificial Sequence
<220> FEATURE:
<223> OTHER INFORMATION: 8SFL2 blocker oligonucleotide sequence
<220> FEATURE:
<221> NAME/KEY: modified_base
<222> LOCATION: (8) ... (8)
<223> OTHER INFORMATION: pyrrolo-deoxycytosine
<220> FEATURE:
<221> NAME/KEY: modified_base
<222> LOCATION: (9) ... (9)
<223> OTHER INFORMATION: fluorescein dT
<220> FEATURE:
<221> NAME/KEY: modified_base
<222> LOCATION: (16) ... (16)
<223> OTHER INFORMATION: pyrrolo-deoxycytosine
<220> FEATURE:
<221> NAME/KEY: modified_base
<222> LOCATION: (17) ... (17)
<223> OTHER INFORMATION: fluorescein dT
<220> FEATURE:
<221> NAME/KEY: modified_base
<222> LOCATION: (24) ... (24)
<223> OTHER INFORMATION: pyrrolo-deoxycytosine
<220> FEATURE:
<221> NAME/KEY: modified_base
<222> LOCATION: (25) ... (25)
<223> OTHER INFORMATION: fluorescein dT
<220> FEATURE:
<221> NAME/KEY: misc_feature
<222> LOCATION: (37) ... (37)
<223> OTHER INFORMATION: 3 prime phosphate blocking group is located after this nucleotide

<400> SEQUENCE: 46
tatctatcta tctatctatc tatctatcta tcgccgc 37

<210> SEQ ID NO 47
<211> LENGTH: 39
<212> TYPE: DNA
<213> ORGANISM: Artificial Sequence
<220> FEATURE:
<223> OTHER INFORMATION: Short Tandem Repeat locus - TH01 9.3 allele

<400> SEQUENCE: 47
aatgaatgaa tgaatgaatg aatgatgaat gaatgaatg 39

<210> SEQ ID NO 48
<211> LENGTH: 30
<212> TYPE: DNA
<213> ORGANISM: Artificial Sequence
<220> FEATURE:
<223> OTHER INFORMATION: HYBTH01 oligonucleotide probe
<220> FEATURE:
<221> NAME/KEY: modified_base
<222> LOCATION: (4) ... (4)
<223> OTHER INFORMATION: fluorescein dT
<220> FEATURE:
<221> NAME/KEY: modified_base
<222> LOCATION: (12) ... (12)
<223> OTHER INFORMATION: fluorescein dT
<220> FEATURE:
<221> NAME/KEY: misc_feature
<222> LOCATION: (30) ... (30)
<223> OTHER INFORMATION: 3 prime phosphate blocking group is located after this nucleotide

<400> SEQUENCE: 48
tggtgaatga atgaatgaat gaatgaatga 30

<210> SEQ ID NO 49
<211> LENGTH: 28
<212> TYPE: DNA
<213> ORGANISM: Artificial Sequence
<220> FEATURE:
<223> OTHER INFORMATION: TH01_BL blocker oligonucleotide sequence
<220> FEATURE:
<221> NAME/KEY: misc_feature
<222> LOCATION: (28) ... (28)
<223> OTHER INFORMATION: 3 prime phosphate blocking group is located after this nucleotide

<400> SEQUENCE: 49
atgaatgaat gaatgaggga aataaggg 28

<210> SEQ ID NO 50
<211> LENGTH: 19

<212> TYPE: DNA
<213> ORGANISM: Artificial Sequence
<220> FEATURE:
<223> OTHER INFORMATION: TH01_F oligonucleotide primer

<400> SEQUENCE: 50
ggcttccgag tgcaggtca 19

<210> SEQ ID NO 51
<211> LENGTH: 19
<212> TYPE: DNA
<213> ORGANISM: Artificial Sequence
<220> FEATURE:
<223> OTHER INFORMATION: TH01_R oligonucleotide primer

<400> SEQUENCE: 51
ggtgattccc attggcctg 19

<210> SEQ ID NO 52
<211> LENGTH: 20
<212> TYPE: DNA
<213> ORGANISM: Artificial Sequence
<220> FEATURE:
<223> OTHER INFORMATION: D8F oligonucleotide primer

<400> SEQUENCE: 52
cggcctggca acttatatgt 20

<210> SEQ ID NO 53
<211> LENGTH: 28
<212> TYPE: DNA
<213> ORGANISM: Artificial Sequence
<220> FEATURE:
<223> OTHER INFORMATION: D8R oligonucleotide primer

<400> SEQUENCE: 53
gccttaattt atttacctat cctgtaga 28

<210> SEQ ID NO 54
<211> LENGTH: 38
<212> TYPE: DNA
<213> ORGANISM: Artificial Sequence
<220> FEATURE:
<223> OTHER INFORMATION: HYBD8 oligonucleotide probe
<220> FEATURE:
<221> NAME/KEY: modified_base
<222> LOCATION: (27) ... (27)
<223> OTHER INFORMATION: fluorescein dT
<220> FEATURE:
<221> NAME/KEY: modified_base
<222> LOCATION: (33) ... (33)
<223> OTHER INFORMATION: fluorescein dT
<220> FEATURE:
<221> NAME/KEY: misc_feature
<222> LOCATION: (38) ... (38)
<223> OTHER INFORMATION: 3 prime phosphate blocking group is located
after this nucleotide

<400> SEQUENCE: 54
tctatctatc tatctatcta tctatctatc tattcccc 38

<210> SEQ ID NO 55
<211> LENGTH: 42
<212> TYPE: DNA
<213> ORGANISM: Artificial Sequence
<220> FEATURE:
<223> OTHER INFORMATION: D8BL5 blocker oligonucleotide sequence
<220> FEATURE:
<221> NAME/KEY: misc_feature
<222> LOCATION: (42) ... (42)
<223> OTHER INFORMATION: 3 prime amino C7 blocking group is located
      after this nucleotide

<400> SEQUENCE: 55
gtatttcatg tgtacattcg tatctatcta tctatctatc ta 42

<210> SEQ ID NO 56
<211> LENGTH: 54
<212> TYPE: DNA
<213> ORGANISM: Artificial Sequence
<220> FEATURE:
<223> OTHER INFORMATION: D8BL8 blocker oligonucleotide sequence
<220> FEATURE:
<221> NAME/KEY: misc_feature
<222> LOCATION: (54) ... (54)
<223> OTHER INFORMATION: 3 prime amino C7 blocking group is located
      after this nucleotide

<400> SEQUENCE: 56
gtatttcatg tgtacattcg tatctatcta tctatctatc tatctatcta tcta 54

<210> SEQ ID NO 57
<211> LENGTH: 66
<212> TYPE: DNA
<213> ORGANISM: Artificial Sequence
<220> FEATURE:
<223> OTHER INFORMATION: D8BL11 blocker oligonucleotide sequence
<220> FEATURE:
<221> NAME/KEY: misc_feature
<222> LOCATION: (66) ... (66)
<223> OTHER INFORMATION: 3 prime amino C7 blocking group is located
      after this nucleotide

<400> SEQUENCE: 57
gtatttcatg tgtacattcg tatctatcta tctatctatc tatctatcta tctatctatc 60
tatcta 66

<210> SEQ ID NO 58
<211> LENGTH: 52
<212> TYPE: DNA
<213> ORGANISM: Artificial Sequence
<220> FEATURE:
<223> OTHER INFORMATION: D8BL7.2 blocker oligonucleotide sequence
<220> FEATURE:
<221> NAME/KEY: misc_feature
<222> LOCATION: (52) ... (52)
<223> OTHER INFORMATION: 3 prime amino C7 blocking group is located
      after this nucleotide

<400> SEQUENCE: 58
gtatttcatg tgtacattcg tatctatcta tctatctatc tatctatcta tc 52

<210> SEQ ID NO 59
<211> LENGTH: 65
<212> TYPE: DNA
<213> ORGANISM: Artificial Sequence
<220> FEATURE:
<223> OTHER INFORMATION: D8BL10.3 blocker oligonucleotide sequence
<220> FEATURE:
<221> NAME/KEY: misc_feature
<222> LOCATION: (65) ... (65)
<223> OTHER INFORMATION: 3 prime amino C7 blocking group is located
      after this nucleotide

<400> SEQUENCE: 59
gtatttcatg tgtacattcg tatctatcta tctatctatc tatctatcta tctatctatc 60
tatct 65

<210> SEQ ID NO 60
<211> LENGTH: 16
<212> TYPE: DNA
<213> ORGANISM: Artificial Sequence
<220> FEATURE:
<223> OTHER INFORMATION: Short Tandem Repeat D3S1358 - 1 repeat

<400> SEQUENCE: 60
tctatctgtc tatcta 16

<210> SEQ ID NO 61
<211> LENGTH: 20
<212> TYPE: DNA
<213> ORGANISM: Artificial Sequence
<220> FEATURE:
<223> OTHER INFORMATION: Short Tandem Repeat D3S1358 - 2 repeats

<400> SEQUENCE: 61
tctatctgtc tgtctatcta 20

<210> SEQ ID NO 62
<211> LENGTH: 24
<212> TYPE: DNA
<213> ORGANISM: Artificial Sequence
<220> FEATURE:
<223> OTHER INFORMATION: Short Tandem Repeat D3S1358 - 3 repeats

<400> SEQUENCE: 62
tctatctgtc tgtctgtcta tcta 24

<210> SEQ ID NO 63
<211> LENGTH: 24
<212> TYPE: DNA
<213> ORGANISM: Artificial Sequence
<220> FEATURE:
<223> OTHER INFORMATION: Short Tandem Repeat vWA - 3 repeats

<400> SEQUENCE: 63
tctatctgtc tgtctgtcta tcta 24

<210> SEQ ID NO 64
<211> LENGTH: 28
<212> TYPE: DNA
<213> ORGANISM: Artificial Sequence
<220> FEATURE:
<223> OTHER INFORMATION: Short Tandem Repeat vWA - 4 repeats

<400> SEQUENCE: 64
tctatctgtc tgtctgtctg tctatcta 28

<210> SEQ ID NO 65
<211> LENGTH: 16
<212> TYPE: DNA
<213> ORGANISM: Artificial Sequence
<220> FEATURE:
<223> OTHER INFORMATION: Short Tandem Repeat D2S1338

<400> SEQUENCE: 65
tgcctgcctt ccttcc 16

<210> SEQ ID NO 66
<211> LENGTH: 45
<212> TYPE: DNA
<213> ORGANISM: Artificial Sequence
<220> FEATURE:

<223> OTHER INFORMATION: Short Tandem Repeat D21S11

<400> SEQUENCE: 66
tctatctatc tgtctgtcta tctatctata tctatctatc tatca 45

<210> SEQ ID NO 67
<211> LENGTH: 22
<212> TYPE: DNA
<213> ORGANISM: Artificial Sequence
<220> FEATURE:
<223> OTHER INFORMATION: Short Tandem Repeat D21S11 - 2

<400> SEQUENCE: 67
tctatctatc catatctatc ta 22

<210> SEQ ID NO 68
<211> LENGTH: 16
<212> TYPE: DNA
<213> ORGANISM: Artificial Sequence
<220> FEATURE:
<223> OTHER INFORMATION: Short Tandem Repeat D19S433

<400> SEQUENCE: 68
aaggaaagaa ggtagg 16

<210> SEQ ID NO 69
<211> LENGTH: 32
<212> TYPE: DNA
<213> ORGANISM: Artificial Sequence
<220> FEATURE:
<223> OTHER INFORMATION: Short Tandem Repeat FGA

<400> SEQUENCE: 69
tttctttctt tctttttct ctttctttct cc 32

<210> SEQ ID NO 70
<211> LENGTH: 420
<212> TYPE: DNA
<213> ORGANISM: Homo sapiens
<220> FEATURE:
<221> NAME/KEY: unsure
<222> LOCATION: (38) ... (38)
<223> OTHER INFORMATION: Unknown nucleotide
<220> FEATURE:
<221> NAME/KEY: unsure
<222> LOCATION: (390) ... (390)
<223> OTHER INFORMATION: Unknown nucleotide
<220> FEATURE:
<221> NAME/KEY: unsure
<222> LOCATION: (397) ... (397)
<223> OTHER INFORMATION: Unknown nucleotide
<220> FEATURE:
<221> NAME/KEY: unsure
<222> LOCATION: (402) ... (402)
<223> OTHER INFORMATION: Unknown nucleotide
<220> FEATURE:
<221> NAME/KEY: unsure
<222> LOCATION: (413) ... (413)
<223> OTHER INFORMATION: Unknown nucleotide

<400> SEQUENCE: 70
atggctgccc tcacggctgc accgggagga tgactgtntt cccactctca gtcctgccga 60
ggtgcctgac agccctgcac ccaggagctg gggggtctaa gagcttgtaa aaagtgtaca 120
agtgccagat gctcgttgtg cacaaatcta aatgcagaaa agcactgaaa gaagaatcca 180
gaaaaccaca gttcccattt ttatatggga gcaaacaaag gcagatccca agctcttcct 240
cttccctaga tcaatacaga cagacagaca ggtggataga tagatagata gatagataga 300

-continued

```
tagatagata gatagatatc attgaaagac aaaacagaga tggatgatag atacatgctt    360

acagatgcac acacaaacgt aaatggtatn aaaaatngga tncactcttg tanggttgtt    420


<210> SEQ ID NO 71
<211> LENGTH: 239
<212> TYPE: DNA
<213> ORGANISM: Homo sapiens

<400> SEQUENCE: 71

ccagcctggc ccacacagtc ccctgtacac agggcttccg agtgcaggtc acagggaaca     60

cagactccat ggtgaatgaa tgaatgaatg aatgaatgaa tgagggaaat aagggaggaa    120

caggccaatg ggaatcaccc cagagcccag ataccctttg aattttgccc cctatttgcc    180

caggaccccc caccatgagc tgctgctaga gcctgggaag ggccttgggg ctgcctccc     239
```

OLIGONUCLEOTIDES AND USES THEREOF

This application is a U.S. national phase application of, and claims priority to and the benefit of, International Patent Application No. PCT/GB2008/003555, filed Oct. 21, 2008, and it claims priority to, and the benefit of, foreign patent applications GB 0720675.8, filed Oct. 22, 2007, and GB 0815113.6, filed Aug. 19, 2008. The disclosures of all of these applications are expressly incorporated herein by reference in their entireties.

The present invention relates to oligonucleotides, and in particular to their use in detecting tandem repeats in DNA.

A multitude of technologies and probe systems for detecting specific DNA sequences and scoring known single nucleotide polymorphisms (SNPs) are known, including homogeneous polymerase chain reaction (PCR), TaqMan™ probes, Eclipse probes, molecular beacons, Scorpion primers, simple hybridisation probes, ResonSense probes, GenePin probes and Hybridisation Beacons (HyBeacone). These are discussed, for example, in our earlier patent applications WO 01/73118 and WO 2007/010268.

Although many DNA polymorphisms and mutations are SNPs, many are due to tandem repeats of DNA sequences. Typically, at present, such repeats in genomic DNA are analysed by size analysis or DNA sequencing, for example following PCR amplification of the target DNA sequence. Although attempts have been made to use oligonucleotide probe systems to identify tandem repeats in DNA (for example, see Radtkey et al (2000) *Nucl. Acids Res.* 28, e17(i-vi)), until now, there has been no practical way of analysing these repeat sequences using hybridisation probes.

DNA fingerprinting or profiling was invented by Alec Jeffreys following his discovery of repeated DNA sequences within the human genome (Jeffreys 1985a, 1985b). The repeated sequences termed STRs (short tandem repeats) or VNTRs (variable number tandem repeats) were found to be of different lengths in different individuals. In the first description of DNA profiling, a number of such loci were typed by the use of restriction enzymes, enzymes which cut DNA at specific nucleotide sequences, to release fragments of different lengths based on the number of iterations of the repeated sequence between the enzyme recognition sequences. In those early days of DNA profiling, the fragments were separated on agarose gels and the specific fragments containing the STRs of interest identified by the use of radioactive DNA probes. This was a complex and time consuming process and since the first description of DNA profiling and identity determination a number of improvements and developments have impacted dramatically on the methodology improving the ease of analysis and therefore the number of samples which can be processed as well as the discriminatory power and cost.

In the most current form of the method, the polymerase chain reaction (PCR) is used to amplify the STR loci which are then separated by a technique such as capillary electrophoresis (CE). Within the UK, hundreds of thousands of samples are processed annually ranging from routine mouth swabs to serious crime scene samples for comparison to the national DNA data base which currently holds in excess of 2 million such profiles.

Despite the ability of laboratories to generate profiles from simple samples such as mouth swabs in as little as a single working day for urgent cases, it is difficult to see how this could be achieved on a routine basis for all samples. Further, if the time from sample collection to arrival at the laboratory is taken into account, it is clear that the majority of profiles cannot be determined in a timely manner. In consequence, a suspect in custody must often be released in the absence of additional evidence before a DNA profile can be obtained analysed. The consequence of this may be that an individual, apprehended for a relatively minor offence and subsequently released, may later be determined to be the perpetrator of a serious crime who must then be re-arrested if indeed they can be located. This is not only a time consuming and costly process but there is also the risk that such an individual may commit further potentially serious offences which would have been entirely preventable if the profile could have been made available whilst they were still in custody.

In the current PCR based method comprising DNA extraction, STR amplification, CE based size separation and analysis, aspects of the process and the cost and complexity of the equipment used mean that STR profiling is predominantly confined to the specialist laboratory with the consequential restriction on turnaround times which can ultimately be achieved. However, if profiling is to become sufficiently rapid that results can be obtained routinely whilst an individual is still in custody then a way must be found in which analysis can be performed on site.

In other non-forensic DNA analysis a suitable approach has been to use homogeneous PCR in which the DNA is both amplified and analysed in a single tube by simple changes in fluorescence. A number of such fluorescent based probe systems including HyBeacon and TaqMan probes (reviewed in WO 01/73118 and WO 2007/010268) have been used to determine variations in DNA sequence such as single nucleotide polymorphisms (SNPs) insertions and deletions. However, such probes have not been used to determine longer length polymorphisms as is required for STR or other DNA sequence analysis nor indeed is it obvious how such length polymorphisms could be determined using homogeneous probe systems.

A number of groups have described homogeneous probe systems enabling the analysis of PCR products within a single tube using for example the cycle at which amplification is first detected in order to provide a relative quantification of one DNA sequence within another such as for mixtures of animal species in food analysis, or of one allelic variant within another such as for genotyping and carrier status with respect to a single nucleotide polymorphism or SNP. We have previously described novel fluorescent probe systems, HyBeacons, which can identify subtle sequence differences such as SNPs or small insertions or deletions because of their dramatic influence on melting temperature and the novel nature of the structure of HyBeacons enabling this to be achieved. Such approaches could be used to identify individuals by SNP profiles in a homogeneous and potentially portable format. However, existing data bases are currently based on STRs which, because of the significantly more variable nature of STRs which average in the region of 10 alleles per locus, by comparison to SNPs which generally have only 2 alleles per locus. In consequence, the industry standard within the UK of forensic DNA profiling is the SGM+ kit from Applied Biosystems comprising 10 STRs and a gender test in preference to alternative SNP typing panels which would require in the region of 50-100 SNPs to achieve comparative levels of individual discrimination. Of course, whilst a SNP panel could be used for the comparison of individual samples there is currently only an STR based database to which individual samples can be compared.

In an attempt to enable STR typing to be applied in settings outside the specialist laboratory, there have been efforts to combine the various steps of the standard profiling method into a homogeneous format by the use of miniaturised CE. A major advantage of such miniaturised systems is that shorter capillaries result in more rapid analysis. Such capillaries are often etched into microscope slide and are generally 10-50 μm deep by 50 μm wide with a length of the order of a few cm and sealed with a glass coverslip (Wooley and Mathies, 1994). Alternative formats have also been described such as the use of injection moulded plastic (McCormick et al, 1997).

Miniatured CE columns with a length of a few cm, in contrast to the more common ABI systems with a column length of 36 cm, can reduce separation times from around 45 minutes to as little as 2.5 minutes for the Promega PowerPlex™ 1.1 STR kit (Schmalzing et al, 1999). Capillary array systems which can analyse up to 96 samples simultaneously in as little as 2 minutes have also been described (Shi et al., 1999) and more recently multicolour systems have been developed although possessing relatively long separation times (Goedecke et al, 2004).

Portable PCR systems to amplify the DNA prior to separation are also required and a number of such systems ranging from battery powered systems demonstrated for use with 4 loci (Belgrader et al, 1998), to systems integrated with microchip CE devices (Lagally et al, 2001) have been demonstrated. One of the challenges for the future will be the use of multiplex STR kits with rapid amplification technology. Multiplex PCR requires careful optimisation and necessarily involves compromise and balance between reaction optima for the different primer pairs. Rapid PCR is generally more stringent in its reaction conditions and therefore less tolerant of any compromises required particularly in multiplex PCR systems.

In an attempt to simplify the analysis of STRs still further, Nanogen Inc. (San Diego, Calif.) attempted the use of a hybridisation format in which PCR amplified targets were hybridised to capture probes of different lengths immobilised at various positions of a silicon microchip. A probe of constant length with a terminal label was then used to detect the remaining portion of the target sequence and which was directed towards predominantly non-repetitive sequence. Under stringency conditions which were required to be tightly controlled by electronic field and temperature in order to control slippage during hybridisation of the repeat units, only targets enabling probe and capture sequence to hybridise immediately adjacent to each other permitted the terminal bases to participate in base stacking and stabilised this structure. Such complexes were sufficiently stabilised to allow the various alleles of a given locus to be identified by the position of fluorescence on the microchip (Radtkey et al, 2000, Westin et al, 2000) although signal was also produced from shorter capture probe sequences. Such probes were end labelled with a single fluorophore and did not change in fluorescence based upon their hybridisation state. Consequently, it was necessary to rely on capture of the probe and for any unhybridised probe to be washed away in order to detect a given sequence at a given location.

The identification of length polymorphisms, particularly repeat length polymorphisms, has been highly informative in a forensic setting. However, such polymorphisms have many other uses. There are more than 15,000 STR markers across the human genome and, depending upon the informity, can be used to exclude up to several centimorgans of genome in mapping studies (Weissenbach et al, 1992). By way of example, STR mapping studies have been used to identify new loci in associated with Hypertrophic cardiomyophathy (Watkins et al, 1993, Carrier et al, 1993, Thierfelder et al, 1993).

Other length polymorphisms, particularly triplet repeat expansions, are known to cause disease, particularly in the neurodegenerative and other disease areas, including myotonic dystrophy, fragile X syndrome, Huntington disease, several spinocerebellar ataxias and Friedreich ataxia (Sinden 1999). Still other length polymorphorisms may be associated with disease predisposition. For example a minisatellite composed of 14 bp repeat units 600 bases upstream of the insulin gene affects an individual's risk of diabetes (Bell et al, 1982) whereas microsatellite instability and loss of heterozygosity is also a feature of many cancers including lung carcinomas (Ionov et al, 1993). Microsatellite instability has been correlated with a high mutational rate and DNA repair processes (Loeb, L. A. 1994, Frayling, I. M. 1999).

Length polymorphisms are found in many other species and may be advantageously used for typing purposes. For example, *Paracoccidioides brasiliensis* is the etiological agent of paracoccidioidomycosis an endemic mycosis in Latin America where it is estimated that 10 Million people being affected (Restrepo-Moreno, 2003). The study of individual isolates and phylogenetic species in order to further understand this clinically important organism has until recently been hampered by a lack of molecular markers for typing purposes recently rectified by Matute (Matute et al, 2006) building on the success of others. Microsatellite marker systems have provided highly effective methods for the DNA profiling of a number of other organisms and has been successfully used for typing fungi such as *Saccharomyces cerevisiae* (Hennequin 2001), *Aspergillus fumigatus* (Bart-Delabesse et al, 2001) and *Candida* spp. (Foulet et al, 2005).

Similar typing methods have also been published for plant species. More than 2,000 simple sequence repeat markers have been identified from within the sequenced rice genome (McCouch et al, 2002) and other markers also identified within the wheat genome (Roder et al, 1998) rice genome (Brondani et al., 1998, 2003) and others.

The listing or discussion of an apparently prior-published document in this specification should not necessarily be taken as an acknowledgement that the document is part of the state of the art or is common general knowledge.

The present invention provides oligonucleotides, and methods of using oligonucleotides, which can be used to detect and discriminate between different numbers of tandem repeats in a polynucleotide sequence. Thus, the invention finds utility in the fields of medical diagnostics and forensic science; it also finds applications in paternity and relationship testing, linkage mapping, microbial typing, traceability within the food chain and so on.

A first aspect of the invention provides a method for determining the number of tandem repeats in a target polynucleotide, the method comprising (a) providing a sample containing the target polynucleotide, wherein one or more of the tandem repeats in the target polynucleotide is in single stranded form, (b) hybridising a labelled probe oligonucleotide to the single stranded portion of the target polynucleotide, wherein the probe oligonucleotide is complementary to at least one of the tandem repeats, and at least 5 nucleotides of the probe oligonucleotide are complementary to the tandem repeats, in the single stranded portion of the target polynucleotide, and (c) determining the number of tandem repeats in the target polynucleotide based on the hybridisation of the probe oligonucleotide to the single stranded portion of the target polynucleotide.

The method may also be considered to be an assay of the number of tandem repeats in a target polynucleotide.

The target polynucleotide may be DNA or may be RNA. Typically, it is DNA.

As is well known, many naturally occurring polynucleotides, particularly DNA molecules, contain tandem repeats, such as repeats of the form $(ABCD\ldots)_n$ where A, B, C and D are nucleotides and n is the number of times the nucleotide sequence is repeated. The repeats may be more complex than that and particular repeats may be interspersed with other particular repeats. Typically, each tandem repeat contains two or three or four or five or six nucleotides and it may be repeated from 2 to 50 or more times ie n may be 2 to 50 or more. Partial repeats may occur within the repetitive target sequence. Furthermore, STR alleles may comprise more than one type of repeat and may contain non-repetitive sequence located between repetitive elements, eg $(TGCC)_m(TTCC)_n$ and $(TTTC)_3$ TTTTTTCT$(CTTT)_n$CTCC$(TTCC)_2$ for D251338 and FGA STR loci, respectively (SEQ ID NOs.: 1 and 2). Common tandem repeat sequences are given in Table 21 below.

Examples of common tandem repeats are $(GATA)_n$, $(CAG)_n$, and $(TCTTA)_n$.

In some tandem repeats, the repeat sequence may be polymorphic so, for example, one or more of the repeated sequences is slightly varied from the core repeat sequence. For example, the STR THO1 has the specific core repeat sequence AATG. However, in one allele termed 9.3, the seventh repeat is lacking an A base. As discussed in more detail in Example 12, some STRs contain variable TCTA and TCTG repeats.

In step (a) of the method a sample containing the target polynucleotide is provided, wherein one or more of the tandem repeats in the target polynucleotide is in single stranded form. This allows a probe oligonucleotide to hybridise to the single stranded region of the target as is discussed in more detail below. The target polynucleotide may be part of a synthetic DNA molecule or it may be part of a natural DNA molecule. Typically, when the target polynucleotide is DNA it is produced by amplification of a region of another DNA molecule, such as a natural DNA molecule. In this embodiment, the amplification process itself, or the further processing of the amplification product, produces the target DNA wherein one or more of the tandem repeats is in single stranded form. For example, a PCR reaction may be used in which primers are employed that hybridise to regions that flank the tandem repeat in a natural DNA (eg human genomic DNA). The PCR product may be made single stranded, eg by using asymmetric PCR in which one primer is in molar excess to the other as is well known in the art, or a double stranded PCR product may be made single stranded, for example by melting.

It will be appreciated that given tandem repeats may occur in more than one region of a natural DNA. Thus, it is generally desirable for the particular target polynucleotide (eg DNA) of interest to be amplified from the natural DNA (such as genomic DNA), for example using PCR primers which hybridise to unique regions which flank the tandem repeat region of interest found within the natural DNA.

Typically, when the target polynucleotide is an RNA molecule, it is produced by transcription from a suitable DNA template. For example, target RNA may be produced by in vitro transcription of a DNA molecule which contains a promoter upstream of the locus to be analysed. Suitable RNA polymerases for the production of target RNA include SP6 and T7 RNA polymerases. Thus, for example, DNA may be amplified from a natural DNA using PCR in which one of the primers contains the recognition site for RNA polymerase. In the presence of RNA polymerase and suitable nucleotides, single stranded RNA may be produced.

In a preferred embodiment, the method includes the further step after or with step (a) of (a1) hybridising a blocking oligonucleotide to at least one but not all of the tandem repeats in the target polynucleotide provided in step (a) so that one or more of the tandem repeats in the target polynucleotide remains in single stranded form following hybridisation of the blocking oligonucleotide.

In one embodiment in step (a1) two or more blocking oligonucleotides are hybridised to at least one but not all of the tandem repeats provided in step (a) so that one or more of the tandem repeats in the target polynucleotide remains in single stranded form following hybridisation of the blocking oligonucleotides.

It will be appreciated that by using a blocking oligonucleotide (or blocking oligonucleotides), it is possible to limit the number of tandem repeats which are present in single stranded form in the target polynucleotide in the sample. For example, if the target polynucleotide (in the absence of blocking oligonucleotide) contains 12 tandem repeats in the target polynucleotide in single stranded form, and the blocking oligonucleotide is able to hybridise to three of them (because it contains a portion of polynucleotide complementary to three tandem repeats), the number of repeats present in single stranded form in the target polynucleotide in the sample in the presence of blocking oligonucleotide is nine.

Conveniently, the blocking oligonucleotide (or blocking oligonucleotides) hybridises to at least two tandem repeats in the single stranded portion of the target DNA, for example 3 or 4 or 5 or 6 or 7 or 8 or 9 or 10 or 20 or 30 or 40. The number of tandem repeats in the blocking oligonucleotide is determined by the possible number of tandem repeats that may be present at a particular locus which is to be analysed. Typically the blocking oligonucleotide is complementary to at least 8 nucleotides (or at least 12 or at least 16 or at least 20 nucleotides) in the tandem repeat(s) present in the single stranded portion of the target DNA. With current technologies, oligonucleotides can be synthesised with up to 250 nucleotide units, and even longer could be expected to be synthesisable in the future.

Preferably the blocking oligonucleotide (when it is complementary along its length to single stranded DNA in the target DNA) is from 12 to 150 nucleotides in length, for example from 12 to 120 or 12 to 100 or from 12 to 90. When the blocking oligonucleotide has an additional function (as described below) the oligonucleotide may be longer, for example from 20 to 180 nucleotides, typically 30 to 150 nucleotides in length, for example, 30 to 120, 30 to 100, 30 to 80 nucleotides in length.

The blocking oligonucleotide or blocking oligonucleotides need not be an integral multiple of the bases in a tandem repeat. Rather, they may include partial repeats so that the blocking oligonucleotide binds to the tandem repeat in an "off-set" manner.

The use of "off-set" blocking oligonucleotides is particularly preferred when two or more blocking oligonucleotides are used, and the use of such "off-set" blocking oligonucleotides is useful as exemplified in the following circumstances.

A sample containing types 8,10 repeats analysed in the presence of a 7 repeat blocker reveals a combination of 1 and 3 repeat units for the probe to hybridise to. However this will appear as a similar result to a sample containing 11,13 repeats if analysed in the presence of a 10 repeat blocker. Thus, with both blockers present, it is difficult to determine which combination of repeats is present in the sample.

In the example described above, if instead of the 10 repeat blocker a 10.2 repeat blocker is used (the '0.2' designates the first two bases of the next repeat) then the sample containing the 11,13 repeats will now only have a 0.2 and 2.2 repeat sequence to hybridise to which will result in shifted melt peaks. Thus, the off-set blocker approach is especially useful where otherwise the melt peaks are otherwise superimposed. This off-set blocking approach may, for example, be used for the combination of up to 4 blockers with a 4 base repeat sequence (by using increasing size range blockers with lengths offset by the addition of 1 base), or 5 blocker for a 5 base repeat, and so on.

In this way, blocking oligonucleotides may be "superimposed" to provide an all-in-one-tube assay which can be used to distinguish different numbers of repeats in the same sample. Typically, the different super-imposable off-set blocking oligonucleotides with partial repeats are selected so that there is a difference in melting peak $T_m$ of at least 0.5° C. between each different length variant (in tandem repeat number). Typically, with the use of different off-set blocking oligonucleotides it is possible to analyse a single, variable locus which may contain multiple alleles differing in the number of tandem repeats in a single PCR. This embodiment is described in more detail in Example 12.

For the avoidance of doubt, a target DNA of the invention which contains x tandem repeats in single stranded form may be converted into a target DNA of the invention which contains x-y tandem repeats in single stranded form by using a blocking oligonucleotide or blocking oligonucleotides which is able to hybridise to y tandem repeats.

Typically, there are 2 or 3 or 4 or 5 or 6 or 7 or 8 or 9 or 10 or 11 or 12 or 13 or 14 or 15 tandem repeats in the target polynucleotide in single stranded form. Preferably, there are between 2 and 10, more preferably between 4 and 8. These typical number of tandem repeats in the target polynucleotide in single stranded form may be available in the presence of blocking oligonucleotide or in its absence. Conveniently, the single stranded portion of the target polynucleotide which contains tandem repeats contains at least 8, preferably at least 12, more preferably at least 16 or at least 20 nucleotides.

As is well known, a common type of polymorphism relates to the number of tandem repeats at a particular locus, which may vary significantly. It will be appreciated that the method of the invention is to be used to determine the number of tandem repeats and it is preferred that in any given assay a small range of tandem repeats are in single stranded form. Thus, in order to determine the number of tandem repeats which may be present at a particular locus, it may be necessary to carry out the method with no blocking oligonucleotide and also to carry out the method separately with one or more blocking oligonucleotide which are able to hybridise to different numbers of tandem repeats. In this way, for any given locus which is known to have multiple alleles which vary by the number of tandem repeats, it is possible to produce target polynucleotides which have similar size single stranded portions (e.g. with a reduced variability in the number of repeats in single stranded form). It will be appreciated that more than one blocking oligonucleotide may be used, provided that there is retained one or more tandem repeats in the target polynucleotide which remain in single stranded form following hybridisation of the blocking oligonucleotides.

In one embodiment, in which the tandem repeat sequences are polymorphic (for example in the STR THO1, or in the STRs described in Example 12), it is desirable that the blocking oligonucleotide blocks the region of variability so that the target polynucleotide in single stranded form contains only the same repeats. For example, as described in Example 12, the blocking oligonucleotide for the STR D8S1179 leaves only TCTA repeats available for hybridisation with the probe oligonucleotide.

Preferably, unless off-set blockers are used as mentioned above, it is preferred that different target polynucleotides containing one or more tandem repeats remaining in single stranded form following hybridisation of the blocking oligonucleotide are generated by the blockers so as to avoid the same Tm for different alleles.

As is discussed in more detail below, the blocking oligonucleotide may be an oligonucleotide which is also used to produce the target polynucleotide wherein one or more of the tandem repeats in the target polynucleotide is in single stranded form, for example as part of a primer used in a PCR reaction.

The labelled probe oligonucleotide in step (b) may be any suitable probe oligonucleotide. Conveniently, the probe oligonucleotide is complementary to at least 2 or 3 or 4 or 5 or 6 or 7 or 8 of the tandem repeats and this may be determined based on the locus to be analysed. Preferably, the probe oligonucleotide is complementary to from 4 to 10 of the tandem repeats, although for a dinucleotide repeat it may be preferred that the probe oligonucleotide is complementary to at least 5 or 6 of the tandem repeats. Conveniently, a portion of between 5 and 40 nucleotides of the probe oligonucleotide is complementary to the tandem repeats in the single stranded region of the target polynucleotide. Typically, the probe oligonucleotide is complementary to at least 8 nucleotides in the tandem repeat(s) present in the single stranded portion of the target polynucleotide: more preferably it is complementary to at least 10 or 12 or 15 or 20 nucleotides in the tandem repeat(s) present.

It is preferred that the oligonucleotide probe is able to bind to the single stranded target polynucleotide with a Tm in the range 40° C. to 70° C. as is described in more detail below.

In a preferred embodiment the oligonucleotide probe is fluorescently labelled. It may contain a single fluorescent label or it may contain a plurality of fluorescent labels. Typically the fluorescent label is attached to an internal residue.

Typically, the oligonucleotide has 2 or 3 or 4 or 5 or 6 or 7 or 8 or 9 or 10 internal residues labelled with a fluorophore. The number may depend on the length of the oligonucleotide. Typically up to about one-third of the internal residues are labelled with a fluorophore, but it may be fewer.

The length of the probe oligonucleotide of the invention is preferably such that it is suitable for hybridising with a single stranded portion of the target polynucleotide, to provide a stable hybrid whose melting temperature depends on the exact sequence of the target and the number of tandem repeats in the single stranded portion of the target, but which typically is within the range 40° C. to 70° C. Oligonucleotides containing less than 15 nucleotide residues in many cases do not form sufficiently stable hybrids, particularly where the two hybridising sequences are not fully complementary, although they can be used in some circumstances. Oligonucleotides, which are longer than about 40 nucleotide residues may form hybrids whose melting temperature is relatively insensitive to the possible presence of a single nucleotide mismatch, although they can be used in some circumstances. Hybridisation of long oligonucleotide probes to long repetitive sequences yields small differences in Tm with targets exhibiting length polymorphisms. The use of oligonucleotide probes which hybridise to more than about 30 to 40 nucleotides of a target polynucleotide typically requires the use of highly sensitive methods for melting curve and melting peak analysis, as is discussed further below.

Typically, the probe oligonucleotide is from 10 to 60 nucleotide residues in length, preferably from 15 to 50 nucleotide residues in length, more preferably 15 to 40 nucleotide residues in length. Thus, typically, the oligonucleotide is from 10 or 11 or 12 or 13 or 14 or 15 nucleotide residues in length up to (and including) 35 or 36 or 37 or 38 or 39 or 40 or 45. Thus, the invention includes the use of probe oligonucleotides within any of the size ranges mentioned.

An oligonucleotide within the size range from 15 to 60 nucleotides may be singly labelled or may have up to around 14 (for 60mer oligonucleotides) of its internal nucleotide residues labelled with a fluorophore, but conveniently an oligonucleotide in this size range has 2 or 3 or 4 or 5 or 6 of its internal residues labelled with a fluorophore. Typically, there is around 3 bases between non-terminal fluorescently labelled nucleotides.

Nucleotide residues are usually derived from the naturally occurring nucleosides A, C, G, T and U. However, nucleotide analogues may be used at one or more locations of the probe oligonucleotide used in the invention, such nucleotide analogues being modified e.g. in the base portion and/or the sugar portion and/or the phosphate link. Base modifications, such as propynyl dU (dT-analogue) and 2-amino dA (dA analogue), generally alter the hybridisation properties and may make the use of oligonucleotides having less than 15 nucleotide residues attractive. In the case of propynyl dU-containing oligonucleotides, they are around 10 residues in length depending on the melting temperature with the target sequence required. Base modifications, such as N4-ethyl-dC (dC analogue) may also be employed to destabilise long oligonucleotide probes, thereby increasing differences in melting temperature with long target sequences. Thus, in some embodiments base modifications may be used to achieve an appropriate Tm shift.

Alternatively, oligonucleotides composed of or comprising peptide nucleic acid (PNA), locked nucleic acid (LNA), 2'-O-methyl RNA, phosphoramidite DNA, phosphorothioate DNA, methyl phosphonate DNA or phosphotriester DNA may be employed to form chemically or enzymatically more stable interactions with target sequences.

It is preferred if the same fluorophore is used throughout the probe oligonucleotide for use in the invention. However, the use of two or more different fluorophores in the same oligonucleotide may be particularly advantageous when the oligonucleotide is used in multiplexing. For example, spectrally distinct fluorophores may also be employed on different probes to simultaneously analyse multiple STR alleles in a single reaction tube. Any fluorophore that can be attached to a nucleotide residue may be used, provided that it does not prevent the oligonucleotide from hybridising to its target sequence. (Multiplex analysis may also be enhanced by the use of different lengths of oligonucleotide probes employed with or without different blocking oligonucleotides, especially with very long STR alleles).

Suitable fluorophores include fluorescein-based fluorophores such as FAM (6-Carboxyfluorescein), TET (Tetrachlorofluorescein), HEX (hexachlorofluorescein); rhodamine-based fluorophores such as ROX (6-Carboxy-X-Rhodamine) and TAMRA (6-Carboxytetramethylrhodamine); the Cy family of dyes, especially Cy3 and Cy5, all available from Glen Research, 22825 Davis Drive, Sterling, Va. 20164, USA.

Other fluorescein dyes, for example those with different emission spectra may be used, such as NED and JOE. Other fluorophores may also be used, such as those in the Alexa, Atto, Dyomics, Dyomics Megastokes and Thilyte dye families as detailed in Tables 14 to 20 below.

In a preferred embodiment of the invention, the probe oligonucleotide is labelled at the 5-position of internal uracil/thymine bases using C6 FAM dU (available from University of Southampton, UK) or Fluorescein dT (available from Glen Research, Sterling, Va.) respectively (in this context, the structure of dT and dU are identical and the terms therefore interchangeable). FMOC-protected phosphoramidites may be incorporated at internal T positions within oligonucleotides and can be used as a point of attachment for a variety of fluorescent dyes, including but not limited to FAM, TET, HEX, ROX, TAMRA, Cy3 and Cy5, all available from Glen Research After oligonucleotide synthesis, the FMOC group may be removed from the 2'-protected uridine and a fluorophore phosphoramidite, such as a suitably protected 6-carboxyfluorescein phosphoramidite, may be coupled to the free 2"-hydroxy group. In yet another embodiment, oligonucleotides may be labelled at internal A, C or G positions, where labelled nucleotides are either incorporated as phosphoramidites during solid phase oligonucleotide synthesis or fluorophores attached post oligonucleotide synthesis using protected phosphoramidites (eg 8-aminoalkyl-dA, 7-aminoalkyl 7-deaza-dA, N(4)-aminoalkyl dC and 5-aminoalkyl-dC).

It is particularly preferred if the labelled probe oligonucleotide is a HyBeacon® probe as disclosed in WO 01/73118 or an oligonucleotide probe as disclosed in WO 2007/010268.

It will be appreciated that in a further embodiment the probe oligonucleotide may be labelled with a quencher molecule, and the target polynucleotide contains a fluorescent molecule whose fluorescence is quenched when the probe oligonucleotide binds the target polynucleotide. Alternatively, the probe oligonucleotide may be labelled with a fluorescent molecule, and the target polynucleotide contains a quencher molecule which quenches the fluorescence of the fluorescent molecule on the probe oligonucleotide when the probe oligonucleotide binds the target polynucleotide. In a further embodiment, probe and blocker oligonucleotides may be labelled with fluorophore and quencher moieties to enhance/quench emission upon hybridisation to (or dissociation from) adjacent target sequences.

In a further alternative, the probe oligonucleotide is labelled with one fluorophore and the target polynucleotide contains another fluorophore such that upon binding of the probe oligonucleotide to the target polynucleotide, there is fluorescence resonance, energy transfer (FRET) that can be measured. In a further embodiment, probe and blocker oligonucleotides may be labelled with donor and acceptor fluorophores to facilitate FRET upon hybridisation to adjacent target sequences.

In the embodiment of the method of the invention in which step (a1) is used and therefore one or more blocking oligonucleotides is employed, it is convenient if the blocking oligonucleotide comprises a fluorophore and the probe oligonucleotide comprises a quencher, or vice versa. Suitable fluorophore/quencher pairs are well known in the art. Similarly, it is convenient if the probe oligonucleotide and blocker oligonucleotide are labelled with fluorophores which are able to participate in FRET with each other. Again, suitable fluorophore pairs are known in the art.

It will be appreciated that the two fluorophores which are able to participate in FRET should be within a suitable distance for FRET to occur when the oligonucleotide or oligonucleotides carrying the fluorophores are hybridised in a configuration to indicate a particular desired result. Similarly, the fluorophore and quencher should be within a suitable distance for quenching to occur when indicating a particular, desired result. In the embodiment where the blocking oligonucleotide contains a quencher and the probe oligonucleotide contains a fluorophore (or in the embodiment where the blocking and probe oligonucleotides contain respective fluorophores capable of performing FRET), the blocking oligonucleotide and probe oligonucleotide hybridise adjacently to the tandem repeats so that the fluorophore/quencher (or fluorophore/fluorophore) pairs are adjacent.

It will be appreciated that in a preferred embodiment, the label (e.g. quencher molecule or fluorescent molecule) can be associated with, and become part of the target polynucleotide, upon binding of a suitably labelled blocking oligonucleotide.

In a preferred embodiment, the probe oligonucleotide is fully complementary to the at least one tandem repeat in the single stranded portion of the target polynucleotide.

In other words, over the region of hybridisation between the single stranded portion of the target polynucleotide and the probe oligonucleotide, Watson-Crick base pairing occurs. However, it will be appreciated that certain mismatches or non-Watson-Crick base pairing may occur, yet the probe is still able to hybridise. In this case, the probe oligonucleotide is partially complementary to the single stranded target polynucleotide. In some circumstances it may be desirable for the probe oligonucleotide to be partially complementary to the single stranded portion of the target polynucleotide, since mismatches can reduce the Tm of an oligonucleotide-target hybrid, thus allowing some degree of control over the Tm (and ΔTm ie difference in Tm which occurs depending on the number of tandem repeats to which the probe oligonucleotide hybridises).

In a similar way, the blocking oligonucleotide may be fully complementary to the single stranded target polynucleotide (preferred) or partially complementary (less preferred).

In a further preferred embodiment, the tandem repeat(s) in the target polynucleotide is flanked by one or two regions which are single stranded. In this case, either the blocking oligonucleotide (if used) or the probe oligonucleotide or both (if both flanking regions are single stranded in the target polynucleotide) may contain an anchor portion which is complementary to a region which flanks the tandem repeat. It will be appreciated that if both a blocking oligonucleotide and a probe oligonucleotide are used which contain an anchor portion, the anchor portion in one of the oligonucleotides will be complementary to one flanking region and the anchor portion in the other oligonucleotide will be complementary to the other flanking region.

Typically, the anchor portion of the blocking oligonucleotide or the probe oligonucleotide will contain from 3 to 40 nucleotides; conveniently from 4 to 30 nucleotides, for example from 4 to 20 nucleotides. Conveniently, for the probe oligonucleotide, the anchor portion is from 5 to 10 nucleotides. Typically, the anchor portion is fully complementary to the flanking region. It will be appreciated that the size and composition of the anchor portion of the blocking oligonucleotide (if used) and probe oligonucleotide may influence the Tm of the blocking oligonucleotide and probe oligonucleotide, and therefore changes in the anchor region of the probe oligonucleotide may allow for some degree of control over the Tm (and ΔTm).

Also, it will be appreciated that the anchor portion is useful in reducing or preventing "slippage" (i.e. it anchors the hybridisation of the oligonucleotide to the flanking region). This allows for improved selectivity of hybridisation of the oligonucleotide to the target polynucleotide, and also improved discrimination between different numbers of tandem repeats to which the oligonucleotide (particularly the probe oligonucleotide) binds.

In a preferred embodiment, steps (a) and (a1)) of the method are carried out simultaneously. In this embodiment, therefore, a sample containing the target polynucleotide is provided at the same time as providing a blocking oligonucleotide or blocking oligonucleotides, such that the target polynucleotide in the sample contains some tandem repeats which are blocked by the blocking oligonucleotide or blocking oligonucleotides and some that are (and remain) in single stranded form in the presence of the blocking oligonucleotide or blocking oligonucleotides and so are free for hybridisation with a probe oligonucleotide. In one embodiment, the blocking oligonucleotide is separate from (ie not covalently joined to) the target polynucleotide. This embodiment is illustrated diagrammatically, in one embodiment, in FIG. 6. This may be considered to be a bimolecular reaction, at least with respect to the generation and blocking of the target polynucleotide.

In a particularly preferred embodiment, a PCR generates the target DNA in which one or more of the tandem repeats in the target DNA is in single stranded form, and a primer used in the PCR also comprises the blocking oligonucleotide. This is illustrated diagrammatically, in one embodiment, in FIG. 8. This may be considered to be a unimolecular reaction, at least with respect to the generation and blocking of the target polynucleotide. It is preferred that the PCR primer that also comprises the blocking oligonucleotide does not possess any regions of substantial self-complementarity.

In a preferred embodiment, the primer used in the PCR (which primer also comprises the blocking oligonucleotide) includes at its 3' end a portion which is complementary to a region in the target DNA which is 3' of the tandem repeats to be analysed and includes at its 5' end a portion which is complementary to at least one tandem repeat in the strand of the PCR product synthesised by said primer. Thus, this primer is one which, in a PCR reaction, generates a strand of DNA which includes the tandem repeats in the target DNA. Because the primer also contains a portion which is complementary to one or more of these tandem repeats, it forms a hair-pin structure by intramolecular hybridisation of the 5' part of the primer (which is also a blocking oligonucleotide in this embodiment) to one or more of the tandem repeats synthesised by use of the primer in the PCR. The 5' part of the primer is not complementary to any region of either primer or oligonucleotide probe and will not participate in hybridisation until after the target sequence is amplified by PCR. It will be appreciated that if the primer contains at its 5' end a portion which is complementary to y of the tandem repeats, y will be blocked. If x tandem repeats are present at the locus amplified in the PCR, x-y tandem repeats will be present in single stranded form in the target DNA produced.

In this embodiment of the invention it is particularly preferred that the primer comprises, from 3' to 5', (i) a portion which is complementary to a region in the target DNA which is 3' of the tandem repeats, (ii) optionally, a spacer portion, (iii) an anchor portion which is complementary to the flanking region in the strand of the PCR product synthesised by said primer, and (iv) a portion which is complementary to at least one tandem repeat in the strand of the PCR product synthesised by said primer.

In a further embodiment, the primer further comprises (v) a clamp portion which is complementary to a clamp portion at the 3' end of the probe oligonucleotide. The clamp portion is located 5' of (iv) (the portion which is complementary to at least one tandem repeat in the strand of the PCR product synthesised by said primer).

In a still further embodiment, at least two different pairs of PCR primer and probe oligonucleotide are used in which the respective clamp portions of each pair of blocking oligonucleotide and probe oligonucleotide are complementary to each other. Preferably, the nucleotide sequence of the clamp portion is selected so that each pair of complementary clamp portion has a different $T_m$. Typically the different Tms differ by at least 0.5° C.

In the embodiments in which the PCR primer contains a clamp portion, the clamp portion has the properties of the clamp portion of the blocking oligonucleotide discussed in more detail below.

Figure 15:
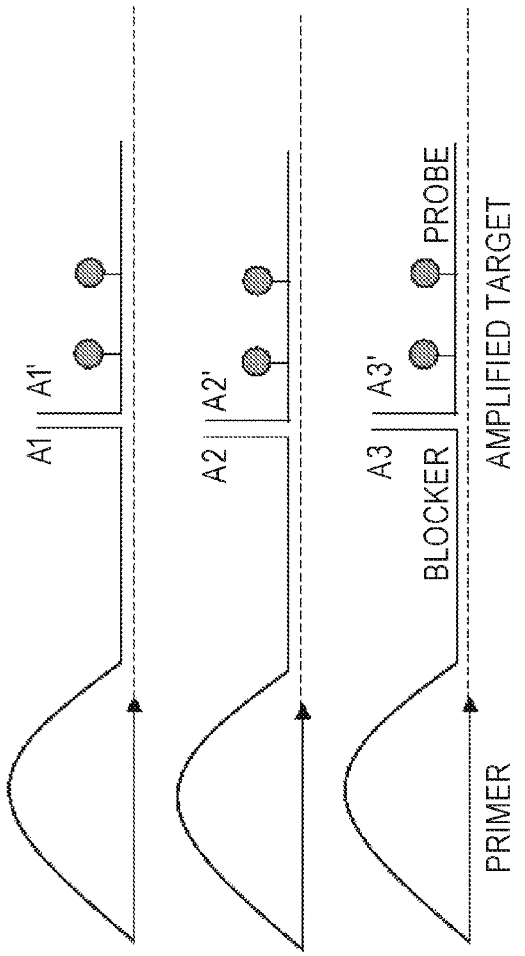

This embodiment is illustrated diagrammatically in FIG. 15.

It is particularly preferred if asymmetric PCR is used to enhance blocker and probe hybridisation to synthesised targets. For example, the unimolecular blocking oligonucleotide/primer may be present at excess concentration compared to the other primer in the PCR which may be employed in a limiting concentration such that it is exhausted early in the PCR thereby generating single-stranded DNA target.

Figure 8:
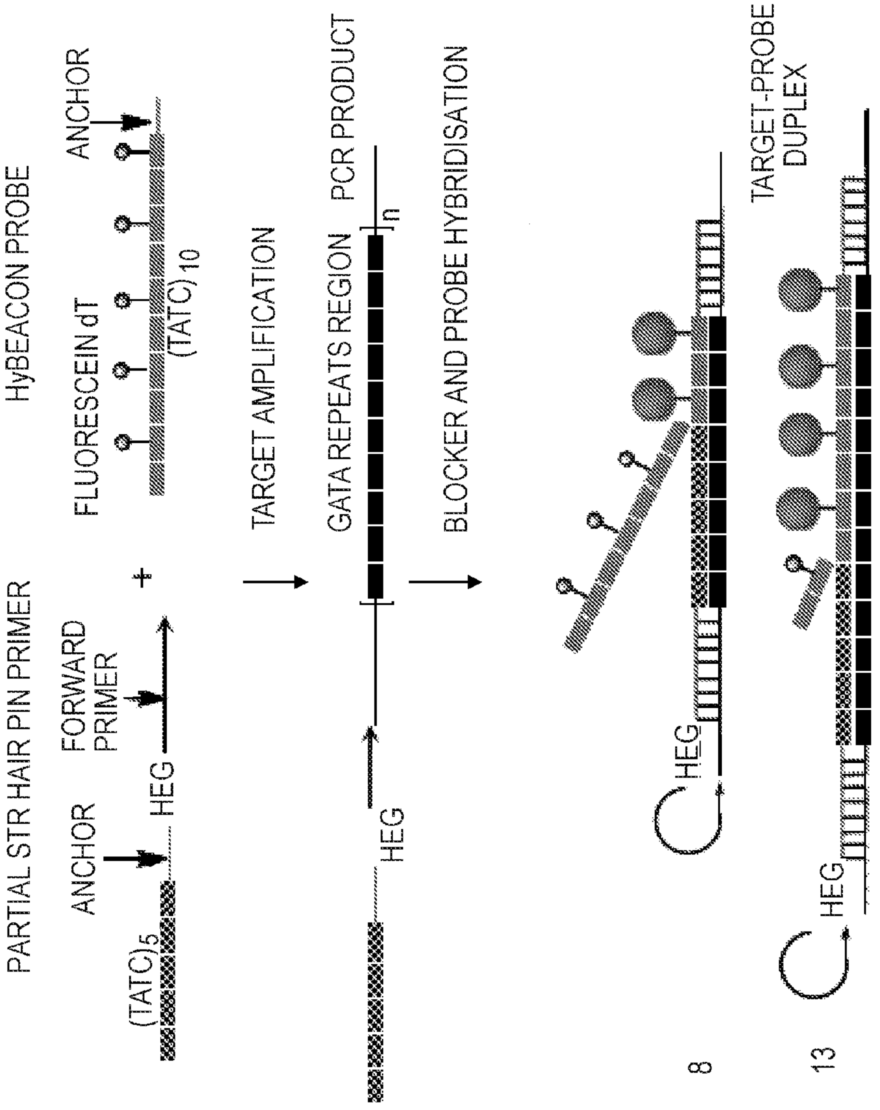

An example of this embodiment is shown diagrammatically in FIG. 8 (in this embodiment the PCR primer and the probe oligonucleotide do not contain clamp portions).

In a different embodiment, the primer used in the PCR (which primer also comprises the blocking oligonucleotide) also comprises the probe oligonucleotide. This embodiment is illustrated diagrammatically in FIG. 16. Typically, a spacer portion is also present between the probe oligonucleotide and the blocking oligonucleotide. Thus, in a typical embodiment the primer comprises, from 3' to 5', (i) a portion which is complementary to a region in the target DNA which is 3' of the tandem repeats, (ii) optionally, a spacer portion, (iii) an anchor portion which is complementary to the flanking region in the strand of the PCR product synthesised by said primer, (iv) a portion which is complementary to at least one tandem repeat in the strand of the PCR product synthesised by said primer, (v) a second spacer portion, and (vi) a probe oligonucleotide. The probe oligonucleotide (vi) is comprised within the PCR primer and may be considered to be a probe portion. It is typically fluorescently labelled, and is complementary to at least one tandem repeat in the strand of the PCR product synthesised by said primer. The portion of the primer which is complementary to a region in the target DNA which is 3' of the tandem repeats is able to hybridise 3' of the tandem repeats, for example under PCR conditions. Typically, this portion of the primer contains from 10 to 30 nucleotides, for example 15 to 30 or 15 to 20 nucleotides, which are complementary to the 3' flanking region. Preferably, it contains 18 to 25 nucleotides. The 3' flanking region typically is located 1 to 200 nucleotides 3' of the target sequence.

Preferably, this portion is fully complementary to the region in the target DNA which is 3' of the tandem repeats; however it may be partially complementary provided that it can still hybridise and participate in a PCR. The 3' end of the primer is free to participate in a chain extension reaction and so contains a 3' OH group. Primers may also contain "universal" bases, such as 5-nitroindole and inosine, in order to "neutralise" known single nucleotide polymorphisms identified within the population.

The spacer portion (ii) is optional. When present it may contain any suitable spacer, by which we include the meaning of a chemical unit which occupies the length of from around 1 to 20 nucleotide residues but which does not participate in base pairing. Typically, the spacer may be a hexaethylene glycol (HEG) or tetraethyleneglycol (TEG) moiety. In another embodiment, the spacer may be one or more abasic residues. Abasic residues retain the spacing of a nucleotide residue but do not participate in base pairing (because the base is absent). In a further embodiment, nucleotide residues are present, but they mismatch the nucleotide residues in the target strand and so do not participate in base pairing.

Typically, the spacer occupies the length of around 1 or 2 or 3 or 4 or 5 nucleotide residues.

In the embodiment in which the probe oligonucleotide is comprised in the PCR primer (FIG. 16), the spacer (v) between the probe oligonucleotide and the blocking oligonucleotide typically has the following properties. It acts as a physical spacer which allows the probe oligonucleotide and blocking oligonucleotide to hybridise independently, without a cumulative effect on stability and probe Tm. Suitably, a simple linear molecule, such as a polymer of a carbohydrate or peptide is used such as to have minimal 3-dimensional rotational constraints, and is long enough to complete a circular structure in space (so that the ends can come back into close proximity). Preferably, the spacer has no intrinsic affinity for, and does not bind, nucleic acid. The spacer is preferably neutral to the hybridisation process to the target sequence. Clearly, the spacer must be able to join chemically to the blocking and probe oligonucleotides.

The anchor portion of the primer which is complementary to the flanking region in the strand of the PCR product synthesised by said primer will contain from 5 to 25 nucleotides, conveniently from 5 to 20 nucleotides, such from 10 to 20. This may be varied depending on the sequence composition of the flanking region. Conveniently, the anchor portion of the primer has a higher Tm than the anchor portion of the probe oligonucleotide. Typically, the anchor portion is fully complementary to the flanking region.

The portion which is complementary to at least one tandem repeat in the strand of the PCR product synthesised by the primer (of which it is a part) typically is complementary to at least one or two or three or four or five tandem repeats. Typically, it is complementary to between 2 and 20 tandem repeats, for example between 4 and 8. It is preferred that this portion is fully complementary to the tandem repeats, but it may be partially complementary, provided that it is still able to hybridise to the tandem repeats in the PCR product synthesised by the primer.

Spacer portions as described above may also be present in probe oligonucleotides and in blocking oligonucleotides. In these cases, it is preferred if the spacer has the length of around 1 or 2 or 3 or 4 or 5, or more, nucleotides.

It will be appreciated that, in the embodiment where the blocking oligonucleotide is not part of a PCR primer, it is preferable that its 3' end does not contain an OH group. This is so that it cannot participate in a chain extension reaction. Thus, the 3' end is typically blocked, for example with a phosphate group or octanediol.

Similarly, it will be appreciated that it is generally desirable for the probe oligonucleotide not to contain a 3' OH, and to be blocked to prevent chain extension, for example by a phosphate or octanediol. In this way, when the method of the invention is carried out using a PCR, the probe oligonucleotide (if present during the PCR) cannot be extended by the DNA polymerase present.

In a further embodiment, the blocking oligonucleotide contains at its 3' (or 5') end a clamp portion which is complementary to a clamp portion which is present at the 5' (or 3') end of the probe oligonucleotide. In this embodiment, the clamp portion of the blocking oligonucleotide and the clamp portion of the probe oligonucleotide hybridise together when the blocking oligonucleotide and the probe oligonucleotide hybridise to the single stranded portion of the target polynucleotide. This embodiment is illustrated diagrammatically, in one particular embodiment, in FIG. 12. The clamp portions typically have from 3 to 10 nucleotides, for example from 4 to 8, such as from 6 to 8. Typically, the clamp portion contains a majority of G or C residues; preferably greater than 75% of the bases are G or C. The sequence of the clamp portion is preferably not complementary to any part of the STR. Conveniently, the clamp portion contributes from 10° C. to 30° C. to thermal stability, typically ensuring that the probe hybridises to the correct sequence and prevents slippage. The Tm of the clamp portion should not increase the Tm of the probe oligonucleotide to the extent that it prevents discrimination of similar length target repeats. In one embodiment, the clamp portion of the probe oligonucleotide contains a fluorescent label and the clamp portion of the blocking oligonucleotide contains a quencher molecule (or vice versa) such that upon binding to the single stranded portion of the target polynucleotide, the fluorophore and quencher interact. Alternatively, the clamp portions of both the probe oligonucleotide and the blocking oligonucleotide contain fluorophores and upon hybridisation to the target polynucleotide are able to participate in FRET (see FIG. 17).

In a preferred embodiment, at least two different pairs of blocking oligonucleotide and probe oligonucleotide are used in which the respective clamp portions of each pair of blocking oligonucleotide and probe oligonucleotide are complementary to each other. Typically, the different pairs of blocking oligonucleotide and probe oligonucleotide differ in the camp portions. Thus one pair may have clamp portions represented by A1:A1' (A1 and A1' being complementary), and another pair may have clamp portions represented by B1:B1', and so on, where, for example A1 is present on the blocking oligonucleotide and A1' is present on the probe oligonucleotide. Typically, the nucleotide sequence of the clamp portion is selected so that each pair of complementary clamp portions has a different $T_m$.

The blocking oligonucleotide with the clamp portion and the probe oligonucleotide with the clamp portion may be considered to be junction oligonucleotides.

In a bimolecular format, the blocking oligonucleotide would typically comprise (i) an anchor portion which is complementary to the flanking region immediately located 5' or 3' of the tandem repeats, (ii) a portion which is complementary to at least one tandem repeat in the synthesised PCR product and (iii) a short G/C rich clamp sequence complementary to a clamp sequence attached to the 5' or 3' end of the probe oligonucleotide to be used.

In a unimolecular format, the blocking oligonucleotide/primer would typically comprise from 3' to 5' (i) a portion which is complementary to a region in a target DNA which is 3' of the tandem repeats (ii) optionally, a spacer portion, (iii) an anchor portion which is complementary to the flanking region in the strand of the PCR product synthesised by said primer, (iv) a portion which is complementary to at least one tandem repeat in the strand of the PCR product synthesised by said primer and (v) a short G/C rich clamp sequence complementary to a clamp sequence attached to the 5' end of the probe oligonucleotide to be used.

The method of the invention is conveniently performed wherein the probe oligonucleotide is selected to allow discrimination between the number of tandem repeats in the single stranded portion of the target polynucleotide according to its melting temperature (Tm). Thus, the same probe oligonucleotide is able to discriminate between different numbers of tandem repeats present. Typically, the probe oligonucleotide can discriminate between 2, 3 and 4 tandem repeats, or 3, 4 and 5 or 4, 5 and 6 or 5, 6 and 7 or 6, 7 and 8 or 7, 8 and 9 or 8, 9 and 10 or 9, 10 and 11 and so on, which are present in single stranded form in the target polynucleotide. Conveniently, the probe oligonucleotide can discriminate between 2, 3, 4, 5, and 6 tandem repeats which are present in single stranded form in the target polynucleotide. However, with the use of suitable blocking oligonucleotides, it is possible to analyse STRs with a very wide range of possible tandem repeats.

It is preferred that the ΔTm (ie the difference in Tm which occurs depending on the number of tandem repeats to which the probe oligonucleotide hybridises) is no less than 0.5° C. between consecutive number of repeat. More preferably, the ΔTm is at least 1° C., typically at least 2° C., for example at least 3° C. The hybridisation properties of the probe oligonucleotide can be adjusted by altering its length, composition, degree of complementarity with the single stranded polynucleotide target, anchor portion (if present) or clamp portion (if present).

Preferably, the hybridisation step (b) of the method is performed at a predetermined temperature near to the Tm or Tms of the hybrid or hybrids formed between the single stranded portion of the target polynucleotide and the probe oligonucleotide. The predetermined temperature may be chosen by reference to the number of tandem repeats to be assayed in the single stranded portion of the target polynucleotide, whether or not there is single stranded flanking region present, and the properties of the probe oligonucleotide as discussed above.

More preferably, the hybridisation step (b) is performed over a range of temperatures encompassing the Tms of the hybrid or hybrids formed between the single stranded portion of the target polynucleotide and the probe oligonucleotide.

Conveniently, the temperature range may be from 30° C. to 75° C. Typically, the hybrids formed have a Tm within this range 40° C. to 65° C. Melt peak analysis typically applies a set algorithms that smoothes data (ie removes fluorescence noise), reducing the potential for allele discrimination when ΔTms are small. The number of repeats is determined by the Tm of melt peaks. High resolution melting curve analysis averages the levels of fluorescence emission in the low and high regions of the temperature range for background correction. Polymorphic alleles exhibiting small ΔTms are more likely to be differentiated using high resolution melting curve analysis. STR alleles may be differentiated by the shape of melt curves, but determination repeat number may require a full complement of length standards for comparison.

Various instruments are available which have low limits of thermal resolution, and which can be used to discriminate between the melting of molecules whose Tms are very close. For example, the high resolution melt (HRM) HR-1 instrument from Idaho Technologies can discriminate between Tms which vary by less than 1° C., for example by 0.5° C., or even by only 0.1° C. Other suitable instruments include LightScanner (Idaho Technologies), Light Cycler 480 (Roche Diagnostics) and Rotor-Gene 6000 (Corbett Life Sciences), which are reported to process thermal resolutions exceeding 1.0° C. Corbett claims that its Rotor-Gene 6000 has a thermal resolution of 0.02° C., although this is based on melting curves rather than peaks.

The target polynucleotide may be any target polynucleotide which contains tandem repeats. Typically, the target polynucleotide is DNA or RNA generated from a natural DNA to be analysed. Typically, the natural DNA is genomic DNA from a plant or animal or microorganism. As is described in the introduction, tandem repeat sequences are found in many genomes, and their analysis is useful in many situations. Analysis of tandem repeats in human and other mammalian DNA may be used for medical diagnostics, forensic science, paternity and relationship testing and linkage mapping.

Analysis of tandem repeats in microorganisms' genomes may be used in disease control (eg strain determination) and in an industrial setting (for example brewing and baking yeast strain determination).

Analysis of tandem repeats in DNA in foodstuffs is useful for tracing materials in the food chain, for example type of plant material used and so on.

A particularly preferred natural DNA is human genomic DNA. As has been discussed above, the target DNA is typically generated by an amplification reaction, such as a PCR.

A second aspect of the invention provides a system for determining the number of tandem repeats in a target polynucleotide wherein one or more of the tandem repeats in the target polynucleotide is in single stranded form, the system comprising (a) a labelled probe oligonucleotide which is complementary to at least one of the tandem repeats, and at least 5 nucleotides of the probe oligonucleotide are complementary to the tandem repeats, in the single stranded portion of the target polynucleotide, and (b) a blocking oligonucleotide which is complementary to at least one but not all of the tandem repeats in the target polynucleotide.

The labelled probe oligonucleotide and the blocking oligonucleotide preferably have the attributes as discussed with respect to the method of the first aspect of the invention.

Convenient systems include but are not limited to:

(1)(a) a labelled probe oligonucleotide containing a clamp portion and (b) a blocking oligonucleotide containing a complementary clamp portion;

(2)(a) a labelled probe oligonucleotide and (b) a PCR primer containing a blocking oligonucleotide as discussed above;

(3)(a) a labelled probe oligonucleotide containing a clamp portion and (b) a PCR primer containing a blocking oligonucleotide and a clamp portion as discussed above; and (4) a PCR primer containing a blocking oligonucleotide and a probe oligonucleotide as discussed above.

The system may be considered to be a "kit of parts" containing the two oligonucleotides (or one oligonucleotide in a certain embodiment). Conveniently, the kit may also comprise components of a PCR for producing the target polynucleotide form a naturally occurring DNA molecule. The kit may also contain methods for detecting the hybridisation of the probe oligonucleotide to the target polynucleotide.

A third aspect of the invention provides an oligonucleotide comprising a portion containing at least two tandem repeats joined to an anchor portion, wherein the sequence of the anchor portion and the at least two tandem repeats occurs contiguously in a target polynucleotide.

Preferably, the oligonucleotide is labelled. Preferably, the labelling of the oligonucleotide is as described above. In this third aspect, the target DNA is typically all or part of a human STR and its flanking region. Preferably, the target DNA is all or part of any of the STRs and flanking regions shown in Table 21.

Preferably, the anchor portion has the same attributes as preferred with respect to the blocking oligonucleotide or the probe oligonucleotide as discussed above.

Preferably, the oligonucleotide of this aspect of the invention also contains a spacer portion. Preferably, the spacer portion has the attributes of the spacer portions as discussed above.

A fourth aspect of the invention provides an oligonucleotide primer for participating in a PCR reaction to amplify a target DNA containing tandem repeats comprising, from 3' to 5', (i) a portion which is complementary to a region in the target DNA which is 3' of the tandem repeats (ii) optionally, a spacer portion, (iii) an anchor portion which is complementary to the flanking region in the strand of the PCR product synthesised by said primer, and (iv) a portion which is complementary to at least one tandem repeat in the strand of the PCR product synthesised by said primer.

Optionally, the oligonucleotide may further comprise (v) a clamp portion. This oligonucleotide may be used in the appropriate embodiments of the invention as discussed above.

Optionally, in a different embodiment, the oligonucleotide may further comprise (v) a spacer portion and (vi) a probe oligonucleotide. This oligonucleotide may be used in the appropriate embodiments of the invention as discussed above.

The oligonucleotide primer preferably does not possess any regions of substantial self-complementarity. The anchor portion and blocking portion (ie portion (iv)) do not participate in hybridisation until after the target DNA has been synthesised.

In this fourth aspect, the target DNA is preferably as described with respect to the third aspect above.

Similarly, the anchor portion and spacer portions are preferably as described with respect to the third aspect above.

The invention also includes a system for determining the number of tandem repeats in a target DNA, the system comprising a oligonucleotide according to the third aspect of the invention to the fourth aspect of the invention.

The invention also includes a method for preparing an oligonucleotide according to the third aspect of the invention, the method comprising (a) selecting a target DNA containing tandem repeats, (b) obtaining the sequence of the tandem repeats and the sequence of one or more of the flanking regions, (c) synthesising an oligonucleotide comprising a portion containing at least two tandem repeats joined to an anchor portion, wherein the sequence of the anchor portion and the at least two tandem repeats occurs contiguously in a target DNA, and, optionally, a clamp portion at its 3' end.

The invention also includes a method for preparing an oligonucleotide according to the fourth aspect of the invention, the method comprising (a) selecting a target DNA containing tandem repeats, (b) obtaining the sequence of the tandem repeats and the sequence of one or more of the flanking regions, (c) synthesising an oligonucleotide comprising, from 3' to 5', (i) a portion which is complementary to a region in the target DNA which is 3' of the tandem repeats (ii) optionally, a spacer portion, (iii) an anchor portion which is complementary to the flanking region in the strand of the PCR product synthesised by said primer, (iv) a portion which is complementary to at least one tandem repeat in the strand of the PCR product synthesised by said primer, and, optionally, (v) a clamp portion or, optionally, (v) a spacer portion and (vi) a probe oligonucleotide.

It is appreciated that if the oligonucleotide is a primer that possesses blocking repeats, it may be preferable if the spacer is present in order to enable formation of the stem-loop for hybridisation.

The target DNA selected in these aspects of the invention may be any DNA which contains a tandem repeat. Typically, the target DNA is genomic DNA. Preferably, it is mammalian genomic DNA, more preferably human genomic DNA. However, it may be DNA from a plant or yeast or bacterium.

Preferably, the target DNA contains a human STR including flanking sequences. More preferably, the STR is one which is described in Table 21.

All documents herein referred to are expressly incorporated into the description by reference in their entireties.

The invention will now be described in more detail with reference to the following figures and examples.

FIG. 1. Melt peaks generated with the STRV2 Oligonucleotide hybridised to oligonucleotide targets. Melt peaks from left to right were generated with targets possessing 5, 7, 8, 10 and 11 tandem repeats of TATC.

Figure 2C:
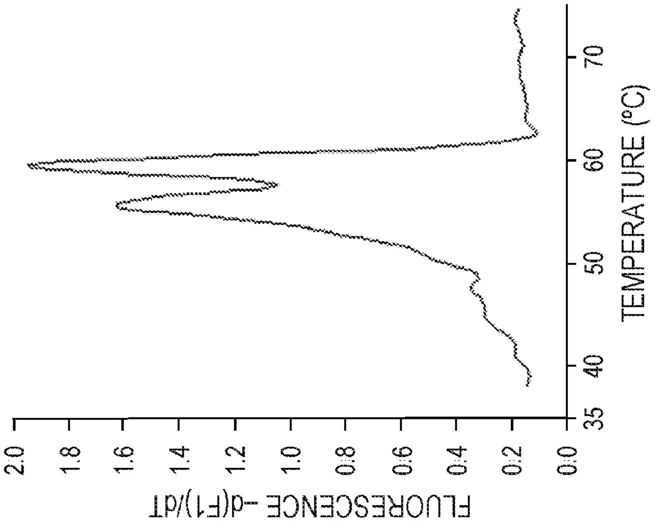
Figure 2A:
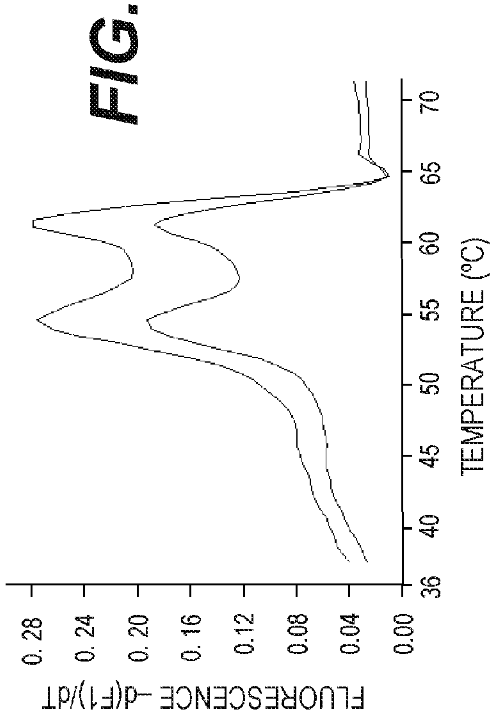
Figure 2B:
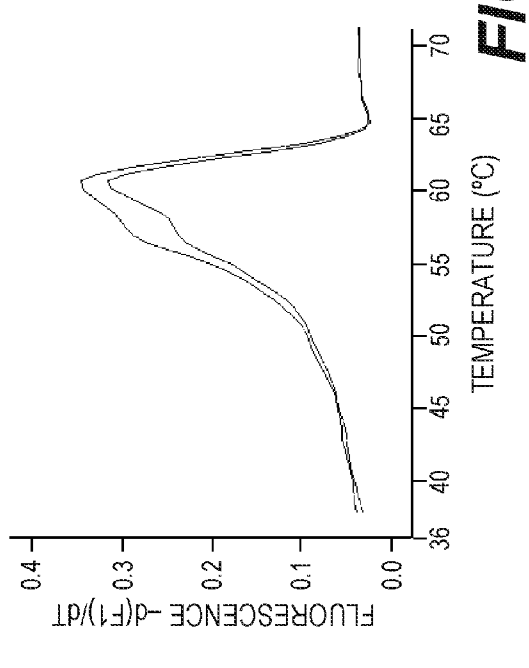

FIG. 2: A) Melting curve analysis of 150 nM of STRV2 Oligonucleotide hybridised to 75 nM of RC7 and 75 nM of RC11 target oligonucleotides. Two clear melt peaks were generated with a ΔTm of 6.6° C. B) Melting curve analysis of 150 nM of STRV2 probe hybridised to 75 nM RC10 and 75 nM RC11 target oligonucleotides. A broad melt peak was produced preventing clear identification of constituent alleles. C) Hybridisation of the STRV2 probe to a mixture of RC8 and RC10 oligonucleotides yields two clear melt peaks with a ΔTm of 3.7° C.

FIG. 3: A) Melt peaks generated with the STRV3 probe hybridised to RC10d and RC11d target oligonucleotides. Two melt peaks were observed. B) Hybridisation of the HYBSTR probe to the RC10e target oligonucleotide resulted in broad and noisy melt peaks due to the absence of an anchor sequence.

FIG. 4: Sequence of the D16S539 STR obtained from the NCBI database (Accession number G07925) (SEQ ID No.: 70).

Figure 5A:
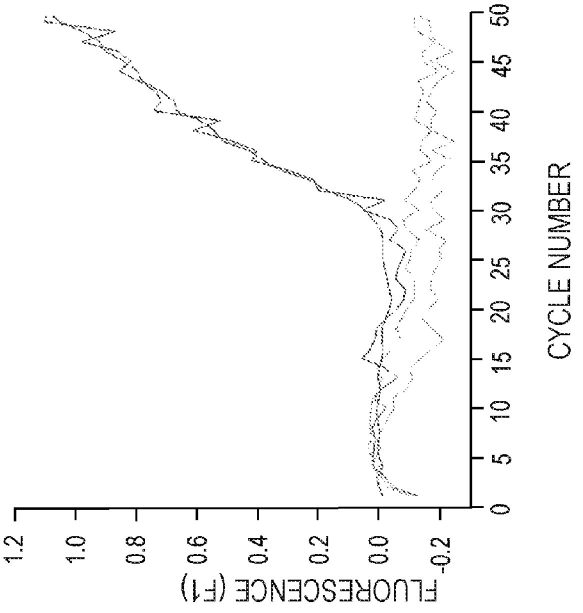
Figure 5B:
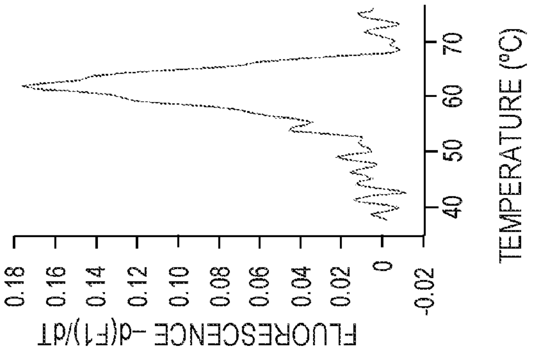
Figure 5C:
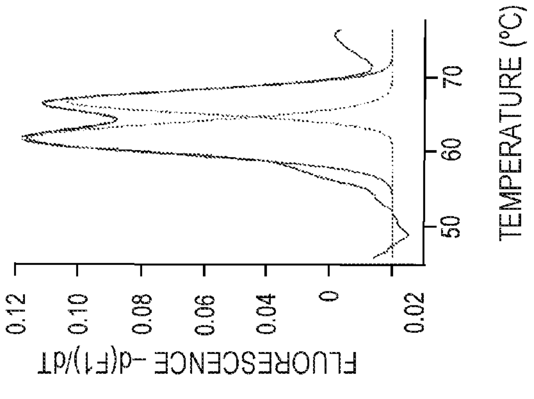

FIG. 5: A) Real-time amplification and detection of D16S539 sequences using a LightCycler instrument and the HYBSTR Oligonucleotide probe. B) Melt peaks generated with a sample heterozygous for 11 and 13 repeats. C) Melt peaks generated with a sample heterozygous for 8 and 13 repeats.

FIG. 6: A) Analysis of STR targets using the bimolecular blocker strategy. STR targets are represented by black boxes, repeats in the blocker oligonucleotide are represented by chequered boxes and repeats in the fluorescent probe are represented by grey squares. The long anchor of the blocker and the molar excess employed (relative to the probe) prevents probe from fully hybridising to targets when repeat number is less than 15. B) Melt peaks generated with target oligonucleotides using the FL1 probe in the presence of the B1 blocker. Melt peaks from left to right were generated with targets possessing 8, 9, 10, 11 and 12 repeats of GATA. C) Melt peaks generated with target oligonucleotides using the FL1 probe in the absence of the B1 blocker. Melt peaks from left to right were generated with targets possessing 5, 6, 7, 8, 9 and 10 repeats of GATA.

FIG. 7: A) Real-time amplification of STR targets from extracted DNA and saliva samples using a LightCycler instrument, the FL1 probe and B1 blocker. The bimolecular B1 blocker reduces the efficiency of PCR, such that detection cycles (Cts) are delayed until approximately 38-40 cycles. Omitting the blocker from PCR assays yields Cts of approximately 32 cycles. B) Melt peaks generated with a sample heterozygous for 9 and 12 repeat alleles.

FIG. 8: A) Analysis of STR targets using the unimolecular blocker/primer strategy. STR targets are represented by black boxes, repeats in the blocker oligonucleotide are represented by chequered boxes and repeats in the fluorescent probe are represented by grey boxes. The blocker repeats, anchor sequence and forward primer are all included in a single oligonucleotide. The blocker and amplified target sequence become part of the same DNA strand, therefore the unimolecular blocker may not inhibit PCR by obstructing the progression of Taq polymerase. The unimolecular binding of the blocker to amplified repeats is thermodynamically favoured over probe hybridisation, preventing full length probe binding when repeat number is less than 15. An illustration of probe hybridisation to D16S539 alleles possessing 8 and 13 repeats is presented.

FIG. 9: A) Real-time amplification of STR targets from extracted DNA and saliva samples using a LightCycler instrument, the FL1 probe and the unimolecular BP1 blocker/primer. Detection Cts for amplified product were approximately 32 cycles. B) From left to right, melt peaks generated with samples homozygous for 11, 12 and 13 repeat alleles. C) Melt peaks generated with a sample heterozygous for 8 and 13 repeat alleles. D) A heterozygous sample possessing 9 and 12 repeat alleles. E) A heterozygous sample possessing 11 and 13 repeat alleles. F) A heterozygous sample possessing 11 and 12 repeat alleles. G) A heterozygous sample possessing 12 and 13 repeat alleles.

FIG. 10: Melt peaks generated with the FL4 probe and BP1 blocker. A) An extracted DNA sample heterozygous for 9 and 12 repeat alleles. B) Direct analysis of an unpurified saliva sample of 11/13 genotype. C) Direct analysis of an unpurified saliva sample of 8/13 genotype. D) An extracted DNA sample of 10/11 genotype. E) An extracted DNA sample of 10/13 genotype.

FIG. 11: LightCycler capillaries containing amplified target sequences, BP1 molecular blocker/probe and FL1 Oligonucleotide were reanalysed using an HR-1 high resolution melting instrument. A) From left to right, melt peaks generated with 11, 12 and 13 repeat alleles. Homozygous 11/11, 12/12 and 13/13 genotypes generate a single melt peak, whereas heterozygous 11/12 and 12/13 genotypes yield broader peaks with shoulders. B) High resolution melt curve data demonstrating reliable differentiation of 11, 12 and 13 repeat alleles. C) 11/12 and 12/13 genotypes are differentiated from 11/11, 12/12 and 13/13 genotypes. D) Reanalysis of LightCycler data using OriginPro 7.5 software (OriginLab, Massachusetts, USA). The FL1 probe, in the presence of BP1 blocker, generated a broad melt peak with an 11/13 genotype saliva sample, only presenting a small peak shoulder for the 11 repeat allele. The OriginPro software identified the shoulder as a true peak and plotted the two component melt peaks for 11 and 13 repeat alleles.

Figure 12:
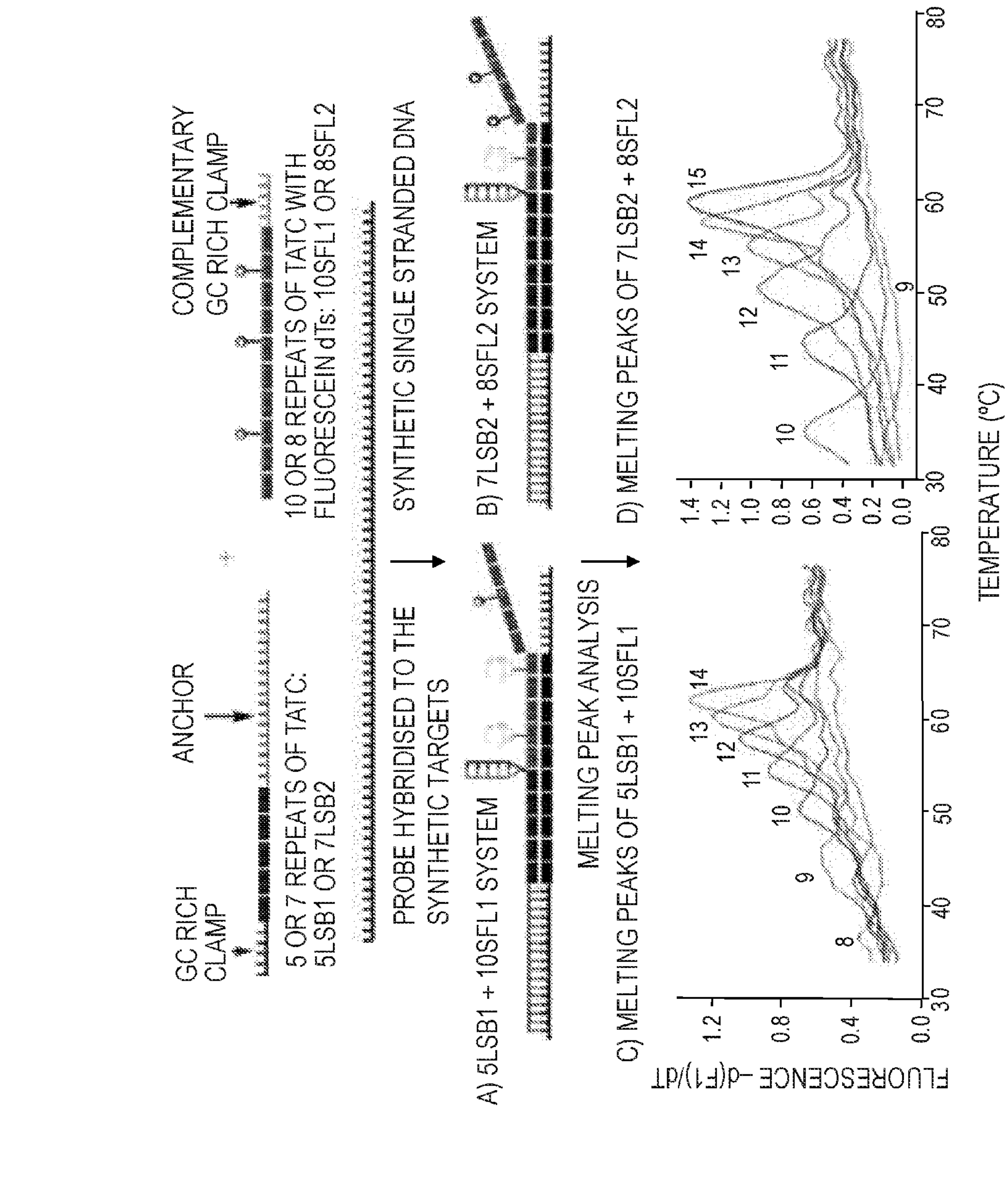

FIG. 12: Blocker oligonucleotides were synthesised with 5 and 7 TATC repeats, an anchor sequence and a GC rich clamp. Oligonucleotides with 10 and 8 TATC repeats were synthesised with a GC clamp complementary to that in the blocker. A) Only 5 repeats of the 10SFL1 Oligonucleotide would hybridise to a 10 repeat target in the presence of the 5LSB1 blocker. B) Only 3 repeats of the 8SFL2 Oligonucleotide would hybridise to a 10 repeat target in the presence of the 7LSB2 blocker. C) Melt peaks generated with 5LSB1 and 10SFL1 using complementary oligonucleotides possessing 8-14 GATA repeats. D) Melt peaks generated with 7LSB2 and 8SFL2 using complementary oligonucleotides possessing 10-15 GATA repeats.

FIG. 13: Sequence of the TH01 STR obtained from the NCBI database (Accession number NT_009237) (SEQ ID No.: 71).

Figure 14:
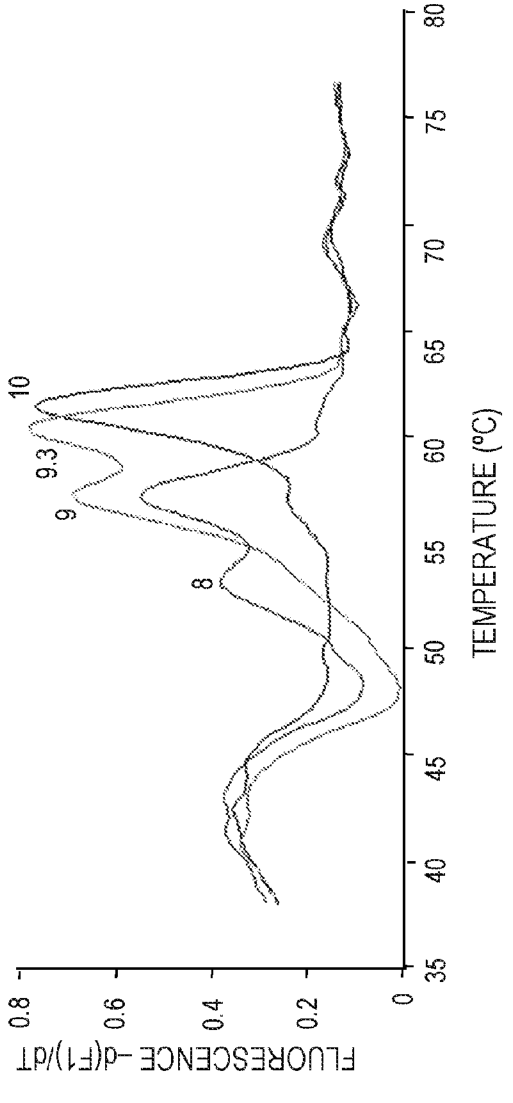

FIG. 14: Melting peaks obtained with amplified TH01 STR alleles, using the HYBTH01 probe and the bimolecular blocker TH01_BL. Melting peaks representing 8, 9, 9.3 and 10 repeat alleles are presented.

FIG. 15: Unimolecular blockers may possess clamp portions of varying length and/or composition (A1, A1, A3 etc), and probe oligonucleotides may contain clamp portions complementary to the clamp portions on the PCR primers (A1', A2', A3' etc).

Figure 16:
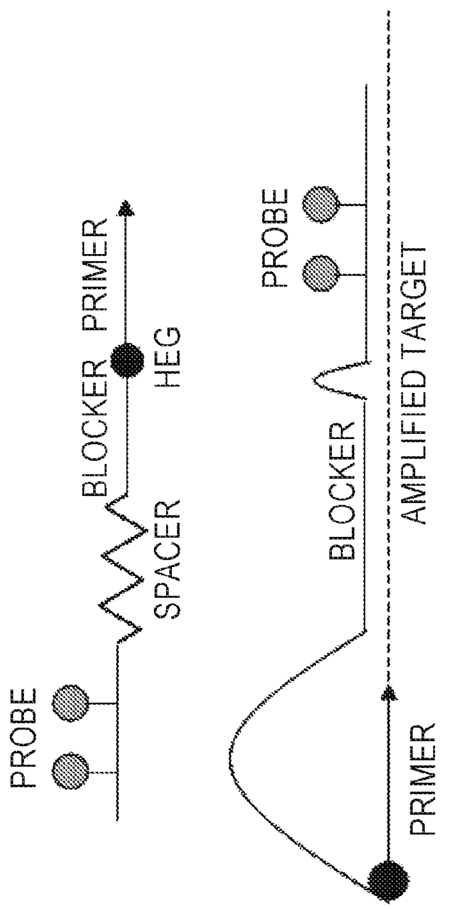

FIG. 16: Probe oligonucleotide attached to PCR primer in a unimolecular construct.

Figure 17:
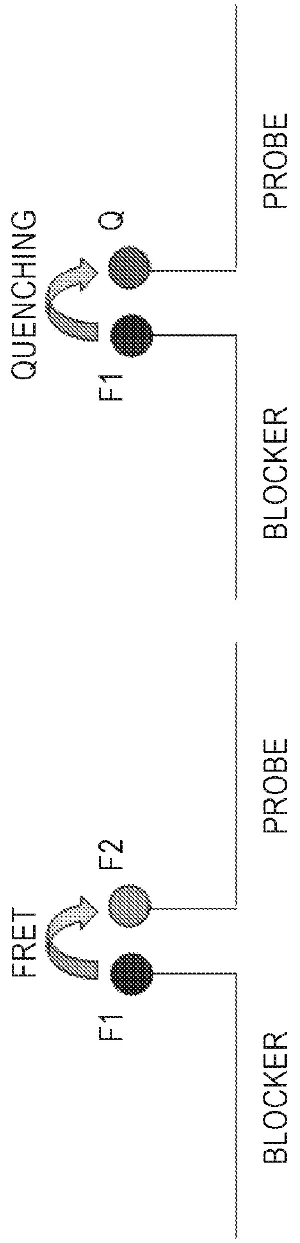

FIG. 17: Complementary clamp portions containing fluorophore, capable of FRET, or fluorophore: quencher pairs.

Figure 18:
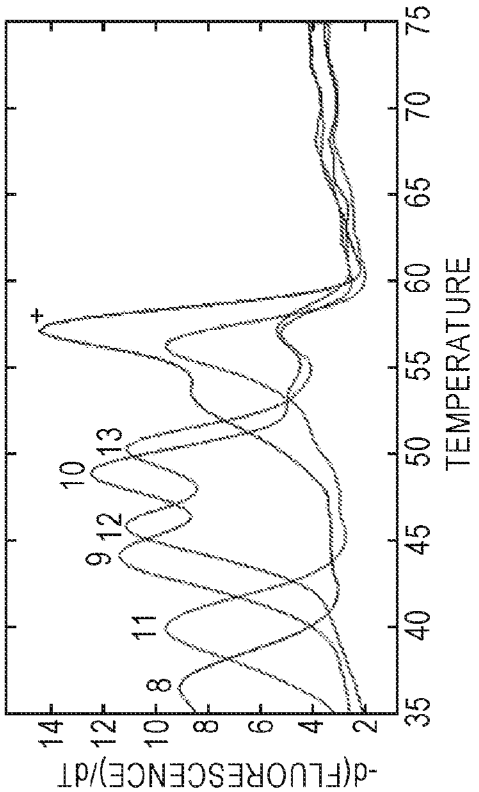

FIG. 18: Results using two "off-set" D8S1179 blockers, permitting detection of 8, 9, 10, 11, 12 and 13 repeat alleles. The "+" melting peak arises from full length probe hybridisation to unblocked target repeats.

Figure 19:
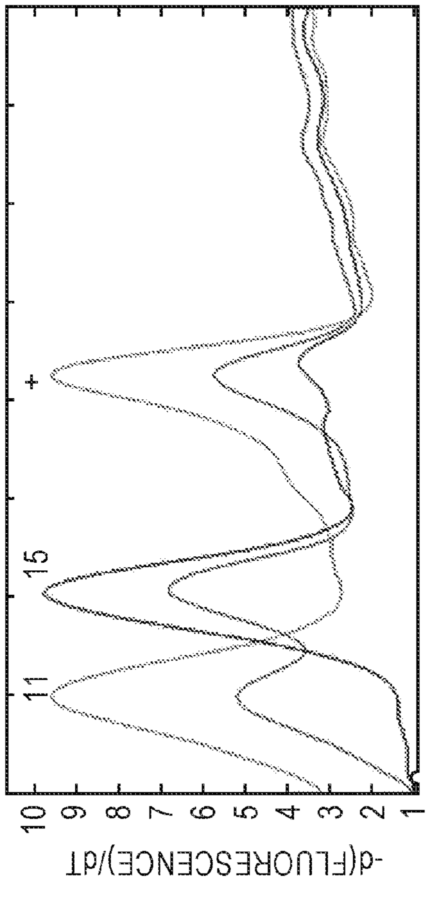

FIG. 19: Detection of 11 and 15 repeat D8S1179 alleles. The 11 and 15 repeat alleles are detected simultaneously using the HYBD8 probe in combination with 7.2 repeat and 10.3 repeat blocker blockers respectively, including all oligonucleotides in a single tube.

EXAMPLE 1

Materials and Methods for the Examples

Oligonucleotide Probe Design and Synthesis

Standard DNA phosphoramidites, solid supports and additional reagents were purchased from Link Technologies or Applied Biosystems Ltd. The psoralen C6 phosphoramidite was purchased from Glen Research Inc. All oligonucleotides were synthesised on an Applied Biosystems 394 automated DNA/RNA synthesiser using a 0.2 μmole phosphoramidite cycle of acid-catalysed detritylation, coupling, capping and iodine oxidation. Normal monomers (A, G, C and T) were allowed to couple for 25 seconds and all other monomers for an additional 300 seconds. Stepwise coupling efficiencies and overall yields of monomers with DMT protection were determined by measuring trityl cation conductivity and in all cases were >98.0%. Cleavage of the oligonucleotides from the solid support was carried out in a concentrated aqueous ammonia (33%) at 55° C. for 5 hours in a sealed tube. Fluorophores were attached to internal residues in the probe sequence using either C6 FAM dU (University of Southampton, UK) or Fluorescein dT (Glen Research, Sterling, Va.). In the case of C6 FAM dU, 6-Carboxyfluorescein (FAM) was attached to the 5-position of uracil bases through methods of DNA synthesis which are well known to those in the field. The oligonucleotides of the invention may possess a 3"-phosphate component or other blocking agent to prevent Taq mediated extension when the probes are incorporated into real-time PCR assays. The quantity of probe obtained from the synthesis was determined by dissolving an aliquot of the oligonucleotide probe in a specific volume of water and measuring the UV absorbance at 260 nm. The concentration of the probe was calculated from the UV absorbance of the oligonucleotide and its extinction coefficient at 260 nm. The extinction coefficient of the oligonucleotide was calculated from the sum of the individual extinction coefficients of the unmodified and fluorescently labelled nucleosides of which it is composed.

Oligonucleotide Purification.

Purification of oligonucleotides was carried out by reversed phase HPLC on a Gilson system using an ABI Aquapore column (C8), 8 mm×250 mm, pore size 300 Å controlled by Gilson 7.12 software. The following protocol was used: Run time 30 minutes, flow rate 3 mL per minute, binary system: Time in minutes (% buffer B); 0 (0); 3(0); 5(20); 22 (100); 25(100); 27 (0); 30(0). Elution buffer A: 0.1 M ammonium acetate, pH 7.0, buffer B: 0.1 M ammonium acetate with 25% acetonitrile pH 7.0. Elution was monitored by ultraviolet absorption at 310 nm (fluorescein oligomers) or 295 nm (all other oligomers). After HPLC purification oligonucleotides were desalted using disposable NAP 10 Sephadex columns (Pharmacia) using the manufacturer's instructions, aliquoted into Eppendorf tubes and stored at −20° C. in distilled deionised water.

Polymerase Chain Reaction

PCR volumes were typically 20 μl, generally comprising 2 μl of sample, 1× QIAGEN PCR buffer, 0.5 μM forward primer, 0.1 μM reverse primer, 1 unit Taq HotStarTaq polymerase, 3 mM total $MgCl_2$, 5 ng/μl BSA (Roche Diagnostics), 1 mM dNTPs (GE Healthcare) and 150 nM of probe. Homogeneous amplification and detection of targets was performed with a LightCycler instrument (Roche Diagnostics) where, following an initial denaturation reaction step (95° C. 15 min), targets were amplified using 50 cycles comprising denaturation (95° C. 5 s), primer annealing (55° C. 10 s) and extension of products (72° C. 10 s). Fluorescence acquisition was performed once per cycle at the end of each primer-annealing step. Melting curve analysis was performed immediately following LightCycler amplification, by briefly denaturing (95° C. 5 seconds) and cooling (35° C. 30 seconds) samples prior to increasing temperature from 35° C. to 95° C. using a 0.1° C./sec transition rate and continuous fluorescence acquisition. Melt peaks were constructed using the LightCycler software (version 3.5) by plotting the negative derivative of fluorescence with respect to temperature (−dF/dT on the y-axis) against temperature (x-axis). Targets were detected and identified using the melting temperatures (Tm) of probe peaks.

Amplification of target sequences was also performed using white 384 well PCR plates (Bio-Rad) and a 384 well Tetrad thermocycler (MJ Research Inc). Thermal protocols generally consisted of an initial denaturation phase (95° C. 15 minutes) to activate the hotstart enzyme, followed by 50 PCR cycles comprising denaturation (95° C. 15 s), primer annealing (55° C. 30 s) and extension of products (72° C. 30 s). Melting curve analysis was performed immediately following amplification using a LightTyper instrument (Roche Diagnostics), gradually heating samples from 35° C. to 75° C. using either a 0.1° C./sec or 0.05° C./sec transition rate.

Analysis of Short Random Repeats

The potential for oligonucleotide probes to analyse short tandem repeats (STRs) was investigated using a series of oligonucleotide targets. Three probes were synthesised to detect and discriminate D16S539 alleles (table 1), which may comprise between 5 and 15 GATA repeats. All probes comprised a 5' GGTG anchor sequence which was found to reduce the possibility of probe slippage along the repeating sequence, thereby preventing the generation of broad and noisy melt peaks. In the absence of an anchor, the 5' repeat of the STR probe might interact with any one of the target repeats, such that full length and partial hybridisation events could occur. The anchor sequence, immediately flanking the repetitive sequence, encourages the probe to hybridise in specific locations and helps prevent the phenomenon of DNA slippage. The stability and effectiveness of the anchor is determined largely by its length and sequence composition. Insufficient stability may enable a degree of DNA slippage, whilst an anchor of excessive Tm might preclude differentiation of STR alleles. Thus, an anchor sequence helps to achieve hybridisation of the first repeat of the target sequence with the first homologous repeat of the oligonucleotide probe in preference to the probe binding in any number of positions.

The STRV2 and STRV3 probes also comprised hexaethylene glycol (HEG) modifications in an attempt to separate the probe into two separate components, thereby reducing overall probe Tm and improving the potential for allele discrimination. Probes were labelled with two fluorescein moieties and possessed a 3' phosphate to prevent extension by Taq polymerase when included in PCR assays.

TABLE 1

Oligonucleotide and oligonucleotide target sequences, where 5, (HEG) and 3P represent the fluorophore C6 FAM dU, hexaethylene glycol and 3' phosphate respectively.

| OLIGO | SEQ ID | SEQUENCE | COMMENT |
|---|---|---|---|
| HYBSTR | 3 | GGTGGATAGA5AGATAGA5AGATAGATAGATA GATAGATAGATAGATAGATAGATAGATA3P | 14 Repeats |
| STRV2 | 4 | GGTGGATAGATAGATA(HEG)GATAGA5AGAT AGA5AGATAGATAGATAGATA3P | 11 Repeats |
| STRV3 | 5 | GGTGGATAGATAGATA(HEG)(HEG)GATAGA5 AGATAGA5AGATAGATAGATAGATAGATAGAT AGATAGATA3P | 16 Repeats |
| RC5 | 6 | TATCTATCTATCTATCTATCCACC | 5 Repeats |
| RC7 | 7 | TATCTATCTATCTATCTATCTATCTATCCACC | 7 Repeats |
| RC8 | 8 | TATCTATCTATCTATCTATCTATCTATCTATCC ACC | 8 Repeats |
| RC10 | 9 | TATCTATCTATCTATCTATCTATCTATCTATCT ATCTATCCACC | 10 Repeats |
| RC11 | 10 | TATCTATCTATCTATCTATCTATCTATCTATCT ATCTATCTATCCACC | 11 Repeats |
| RC10b | 11 | TATCTGTCTATCTGTCTATCTGTCTATCTGTCT ATCTGTCCACC | 5 G/T mismatches |
| RC10c | 12 | TGTCTGTCTGTCTGTCTGTCTGTCTGTCTGTC TGTCTGTCCACC | 10 G/T mismatches |
| RC10d | 13 | TATCTATCTATCTATCCCCTTATCTATCTATCT ATCTATCCACC | Repeat 6 'knock-out' |
| RC10e | 14 | TATCTATCTATCTATCTATCTATCTATCTATCT ATCTATC | 4 bp anchor removed |
| RC11b | 15 | TATCTGTCTATCTGTCTATCTGTCTATCTGTCT ATCTGTCTATCCACC | 5 G/T mismatches |
| RC11c | 16 | TGTCTGTCTGTCTGTCTGTCTGTCTGTCTGTC TGTCTGTCTGTCCACC | 11 G/T mismatches |
| RC11d | 17 | TATCTATCTATCTATCTATCCCCTTATCTATCT ATCTATCTATCCACC | Repeat 6 'knock-out' |
| RC11e | 18 | TATCTATCTATCTATCTATCTATCTATCTATCT ATCTATCTATC | 4 bp anchor removed |

The probe HYBSTR was the starting point for development. Improvements to probe Δ Tm and allele discrimination should be referred back to this probe.

Oligonucleotide targets were synthesised to simulate various D16S539 alleles, possessing 5, 7, 8, 10 and 11 TATC repeats along with a 3' CACC sequence complementary to the probe anchor (table 1). 150 nM of the D16 oligonucleotide probes were hybridised to 150 nM of each target oligonucleotide in TaKaRa PCR buffer and a total of 3 mM of $MgCl_2$. Melting curve analysis was performed using a LightCycler instrument where, following an initial denaturation (95° C. 5 seconds) and cool (35° C. 30 seconds), reactions were heated from 35° C. to 95° C. using a 0.1° C./sec temperature transition rate. Probe melting temperatures observed with synthetic target sequences are detailed in Table 2. The melt peaks generated with the STRV2 probe and each oligonucleotide target are presented in FIG. 1.

Probes were also analysed with combinations of target oligonucleotides, simulating heterozygous genotypes possessing alleles with different numbers of repeats (Table 2). The ability to genotype heterozygous samples is dependent upon the ΔTm of the two D16 alleles present. A Tm difference of at least 3° C. is typically required by the LightCycler instrument to generate heterozygous melt traces with clear constituent peaks (however, other instruments are available which provide greater discriminations, such as a High Resolution Melt instrument like HR-1 from Idaho Technologies). The shorter D16 targets (e.g. 5 and 7 repeats) display much larger ΔTms than longer sequences (e.g. 10 and 11 repeats) and are therefore easier to discriminate. FIG. 2 demonstrates that whilst 7/11 and 8/10 genotypes may be clearly discriminated using STRV2 10 and 11 repeat Tms are too similar to enable simultaneous detection. (However, as discussed below, simultaneous detection of 10 and 11 repeats is achieved using a blocking oligonucleotide (BP1) and a different probe oligonucleotide (FL1), demonstrating a ΔTm of 3.5° C.)

TABLE 2

Probe Tms and ΔTms derived from hybridisation to oligonucleotide target sequences.

| | Probe Tm & (ΔTm) | | |
|---|---|---|---|
| Repeat combination | HYBSTR | STRV2 | STRV3 |
| 5/5 | | 47.66° C. | |
| 7/7 | | 55.09° C. | |
| 8/8 | | 56.83° C. | |
| 10/10 | 63.62° C. | 60.60° C. | 59.84° C. |
| 11/11 | 64.54° C. | 61.70° C. | 61.83° C. |
| 5/7 | | (7.4° C.) | |
| 5/8 | | (9.2° C.) | |
| 5/10 | | (12.9° C.) | |
| 5/11 | | (14.0° C.) | |
| 7/8 | | (1.7° C.) | |
| 7/10 | | (5.5° C.) | |
| 7/11 | | (6.6° C.) | |
| 8/10 | | (3.7° C.) | |
| 8/11 | | (4.9° C.) | |
| 10/11 | (0.92° C.) | (1.1° C.) | (1.99° C.) |

EXAMPLE 2

Heterozygous samples comprising long repeat sequences may not always be typed accurately using the oligonucleotide designs described in Example 1. Since the magnitude of probe ΔTm depends on the length and composition of the STR targets, destabilisation of hybridisation may increase the sensitivity to length polymorphisms. Probe destabilisation may be achieved by a strategy such as:

Introducing nucleotide mismatches to reduce probe Tm. The number of mismatches depends on the length and the sequence composition of the probe and the type of mismatch employed. Larger numbers of stable mismatches, such as G/T, may be employed in multiple repeats along the probe length to reduce Tm. Fewer highly destabilising mismatches, such as C/A, would be required to achieve the same reduction in Tm. An alternative to distributing the mismatches along the length of the probe is to cluster the mismatches thereby removing a whole repeat from the oligonucleotide, such that a 15 repeat probe may for example be separated into 5 and 9 repeating components.

Incorporating base analogues, such as N4-ethyl-dC7-deaza-dG, 7-deaza-dC, C-5 propynyl-dC, C-5 propynyl-dU, 5-methyl-dC, 2-amino-dA, G-clamp1 (a tricyclic aminoethylphenoxazine 2'-dC analogue), Locked Nucleic Acid (LNA), 5'-trimethoxystilbene cap, 5'-pyrene cap. There may be advantages in increasing Tm using such analogues in order to further differentiate the contribution of different probe regions to overall melting temperature in order to further enhance the observed delta Tm between different repeat lengths to modify probe Tm.

Including longer HEG, TEG (or other) spacers to split the probe into individual components.

Label the oligonucleotide probe with more than two fluorophores.

To investigate the affect of nucleotide mismatches on probe Tms and ΔTms, base substitutions were included in oligonucleotide targets rather than the probes for ease of experimental evaluation. The modifications made to target sequences comprising 10 and 11 repeats are detailed in Table 1.

The RC10b, RC10c, RC11b and RC11c incorporated 5 and 10 G/T nucleotide mismatches regularly distributed through the probe/target duplex. The base substitutions reduced the Tm of probe/target duplexes considerably (compare Tables 2 & 3) and also increased the ΔTm of HYBSTR, STRV2 and STRV3 probes. However, the magnitude of the ΔTm increase was insufficient for reliable discrimination of the 10 and 11 STR repeat alleles using the LightCycler software.

Figure 3A:
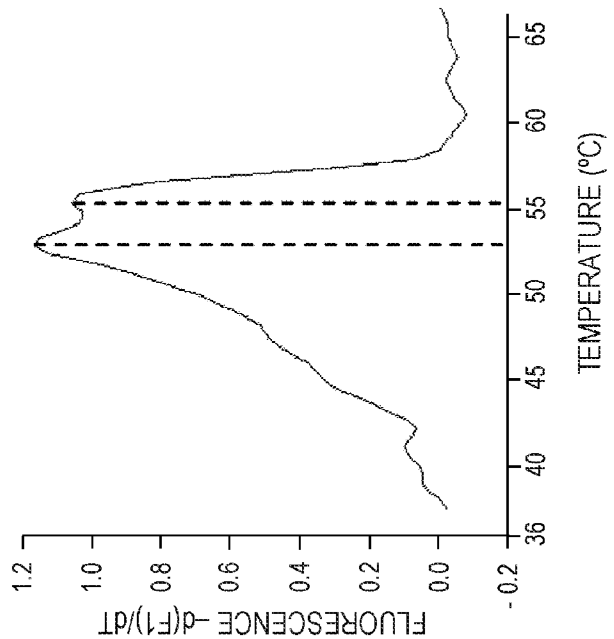

The RC10d and RC11d oligonucleotides incorporated four nucleotide mismatches in the common sixth repeat of the STR targets. These mismatches reduced the Tm of D16 Oligonucleotides and increased the ΔTm between 10 and 11 repeat oligonucleotides (Table 3). Both 10 and 11 repeat peaks were visible using the STRV3 probe (FIG. 3A). However, further enhancements to probe ΔTm are required to reliably identify and discriminate long STR targets using the LightCycler software, and this is demonstrated below.

Figure 3B:
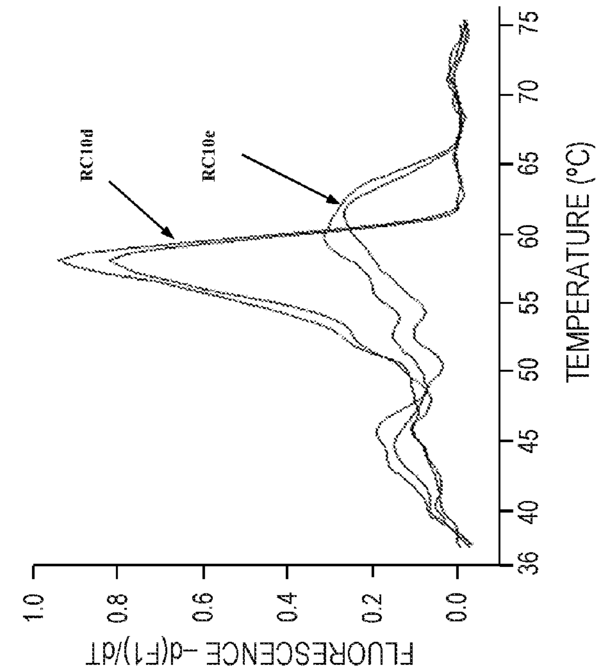

The RC10e and RC11e target oligonucleotides demonstrated the requirement of the 4 bp anchor with the HYBSTR probe. The oligonucleotide generated smooth defined curves with all other modified and unmodified targets, but generated broad and noisy traces in the absence of anchor (FIG. 3B). This reduction in peak quality was caused by probe slippage along the target sequence. Interestingly, the STRV2 probe did not exhibit such a reduction in peak quality in the absence of anchor, possibly due to the presence of the internal HEG modification.

TABLE 3

Probe Tms and ΔTms with mismatched oligonucleotide targets

| Probe | RC10b | RC11b | ΔTm | RC10c | RC11c | ΔTm | RC10d | RC11d | ΔTm |
|---|---|---|---|---|---|---|---|---|---|
| HYBSTR | 56.33 | 57.44 | 1.11 | 48.34 | 49.37 | 1.03 | 57.80 | 59.46 | 1.66 |
| STRV2 | 52.18 | 53.47 | 1.29 | 46.03 | 45.02 | 1.01 | 53.2 | 55.3 | 2.1 |
| STRV3 | 51.05 | 53.54 | 2.49 | 43.22 | 44.54 | 1.32 | 54.37 | 56.03 | 1.66 |

EXAMPLE 3

D16S539 target sequences were amplified by Polymerase Chain Reaction (PCR) using the primers STRF2 and STRR2. Amplicon sizes vary with repeat number and range from 133 bp to 173 bp (see FIG. 4 for gene sequence).

```
STRF2
CAGATCCCAAGCTCTTCCTCTTCCCTAG         (SEQ ID: 19)

STRR2
ACGTTTGTGTGTGCATCTGTAAGCATGTATC      (SEQ ID: 20)
```

Seven saliva samples were analysed directly, without DNA purification, using the HYBSTR probe and a LightCycler instrument. Saliva samples were all heterozygous possessing 9/12, 13/15, 9/13, 11/14, 9/12, 11/13 and 8/13 repeat genotypes. Real-time fluorescence increases and the generation of melt peaks confirmed that D16 targets were amplified efficiently from saliva samples. Heterozygous genotypes possessing D16 alleles differing by 2, 3 or 4 repeats did not generate clear individual peaks for each constituent allele. Instead broad melt profiles combining the peaks from each D16 repeat were generated. A five repeat difference from an 8/13 D16 genotype was sufficient to generate clear peaks for each allele (FIG. 5).

EXAMPLE 4

The affect of an abasic site on duplex stability was investigated using probes possessing both 5' and 3' anchor sequences and probes possessing only a 3' anchor (Table 4). Probes were designed to the minus strand of DNA increasing the number of potential sites for fluorophore attachment. Probes were hybridised to complementary oligonucleotides possessing 5, 7, 10, 12 and 15 repeats (Table 5).

TABLE 4

Oligonucleotide probes employed to analyse the affect of an abasic site, where 4 and 5 represent the abasic site and fluorescein dT fluorescent labels respectively.

| Probe | SEQ ID | Sequence |
|---|---|---|
| 02466R | 21 | CAATGATA**5**CTATCTA**5**CTATCTA**5**CTATCTA**5**CTATCTA**5**CTATCTA**5**CTATCTATCTATCTATCCACC |
| 02467R | 22 | CAATGATA**5**CTATCTA**5**CTATCTA**5**CTATCTA**5**CTATCTA**5**CTATCTA**5**C**4**ATCTATCTATCTATCCACC |
| 02468R | 23 | TA**5**CTATCTA**5**CTATCTA**5**CTATCTA**5**CTATCTA**5**CTATCTATCTATCTATCTATCTATCCACC |
| 02469R | 24 | TA**5**CTATCTA**5**CTATCTA**5**CTATCTA**5**CTATCTA**5**CTATC**4**ATCTATCTATCTATCTATCCACC |

TABLE 5

Oligonucleotides employed as targets for probe evaluation, where $(GATA)_n$ represents the number of STR repeats.

| Oligo | SEQ ID | Sequence |
|---|---|---|
| C5 | 25 | CCCTAGATCAATACAGACAGACAGACAGGTG$(GATA)_5$TCATTGAAAG |
| C7 | 26 | CCCTAGATCAATACAGACAGACAGACAGGTG$(GATA)_7$TCATTGAAAG |
| C8 | 27 | CCCTAGATCAATACAGACAGACAGACAGGTG$(GATA)_8$TCATTGAAAG |
| C9 | 28 | CCCTAGATCAATACAGACAGACAGACAGGTG$(GATA)_9$TCATTGAAAG |
| C10 | 29 | CCCTAGATCAATACAGACAGACAGACAGGTG$(GATA)_{10}$TCATTGAAAG |
| C11 | 30 | CCCTAGATCAATACAGACAGACAGACAGGTG$(GATA)_{11}$TCATTGAAAG |
| C12 | 31 | CCCTAGATCAATACAGACAGACAGACAGGTG$(GATA)_{12}$TCATTGAAAG |
| C13 | 32 | CCCTAGATCAATACAGACAGACAGACAGGTG$(GATA)_{13}$TCATTGAAAG |
| C14 | 33 | CCCTAGATCAATACAGACAGACAGACAGGTG$(GATA)_{14}$TCATTGAAAG |
| C15 | 34 | CCCTAGATCAATACAGACAGACAGACAGGTG$(GATA)_{15}$TCATTGAAAG |

The inclusion of an abasic site generally reduced the Tm of probe hybridisation by approximately 1-2° C. However, no improvement to ΔTm was achieved (Table 6). High quality melt peaks were generated with probes comprising five and six fluorescently labelled T bases. Other probe designs generated high quality melt peaks when labelled with up to 8 fluorescent bases. Probes possessing greater than 8 fluorophores have not been tested to date, but are expected to be functional given a suitable probe length and spacing between labels.

TABLE 6

The affect of an abasic site on probe Tm

| Repeats | 02466R | 02467R | 02468R | 02469R |
|---|---|---|---|---|
| 5 | | | 47.2° C. | 49.0° C. |
| 7 | 60.6° C. | 58.6° C. | 54.9° C. | 54.0° C. |
| 10 | 64.8° C. | 63.2° C. | 63.0° C. | 57.5° C. |
| 12 | 67.0° C. | 64.3° C. | 67.4° C. | 66.1° C. |
| 15 | 68.9° C. | 66.8° C. | 68.9° C. | 68.0° C. |
| ΔTmfor7/15 | 8.3° C. | 8.2° C. | 14.0° C. | 14.0° C. |

EXAMPLE 5

Figure 6A:
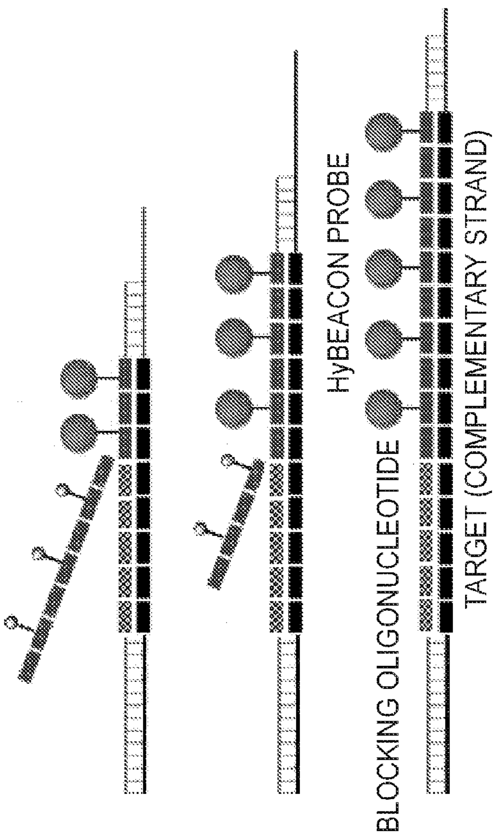

Alleles of D16S539 always possess at least 5 repeats of GATA. Therefore, the Tm of probe hybridisation may be reduced if STR repeats are separated into two oligonucleotides (Table 7). The first oligonucleotide is non-fluorescent and acts as a blocker, comprising the first five common repeats. The second oligonucleotide is a fluorescent probe that hybridises only to additional repeats, i.e. will only detect five repeats of a 10 repeat allele (FIG. 6A). The purpose of the blocker is to reduce the number of STR repeats available to the fluorescent probe, thereby increasing ΔTms between alleles of similar length.

The blocking oligo (B1) consists of 5 repeats of d(TATC), a 31-mer anchor sequence to prevent slippage (which is fully complementary to the flanking sequence) and a 3'-phosphate to prevent the extension of the probe during PCR. The fluorescent oligonucleotide probe (FL1) has 10 repeats of d(TATC), 5 internal fluorescein dT bases (Glen Research) a short six nucleotide anchor (which is fully complementary to the other flanking sequence) and an octanediol PCR blocker at the 3' end (Table 7).

TABLE 7

STR analysis using a bimolecular blocker and oligonucleotide probe, where P, 5 and 6T represent 3' phosphate, fluorescein dT and octanediol respectively.

| Oligo | SEQ ID | Sequence |
|---|---|---|
| B1 | 35 | TATCTATCTATCTATCTATCCACCT-GTCTGTCTGTCTGTATT GATCTAGGGP |
| FL1 | 36 | 5ATCTATC5ATCTATC5ATCTATC5ATCTATC5ATCTATC6T |

Figure 6B:
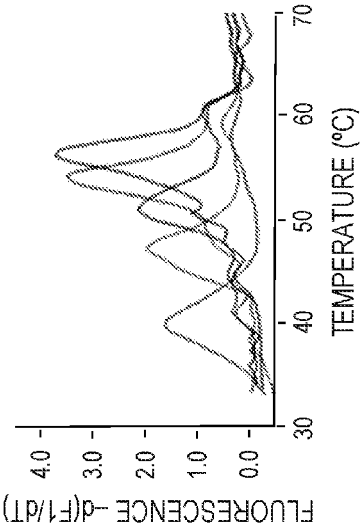

A molar excess of the blocker oligonucleotide was employed to favour hybridisation to the five common repeats. 100 nM of FL1 probe was employed along with 600 nM of B1 blocker to analyse complementary oligonucleotides possessing 8, 9, 10, 11 and 12 GATA repeats (FIG. 6B). Probe Tms and ΔTms for each target are presented in table 8. Splitting the STR probe design into two components considerably enhanced ΔTms and the ability to differentiate alleles of similar length. For example the ΔTm of a 10/11 genotype was 0.92° C. when analysed with the full length HYBSTR probe, but was increased to 2.2° C. with this bimolecular blocking strategy.

Figure 6C:
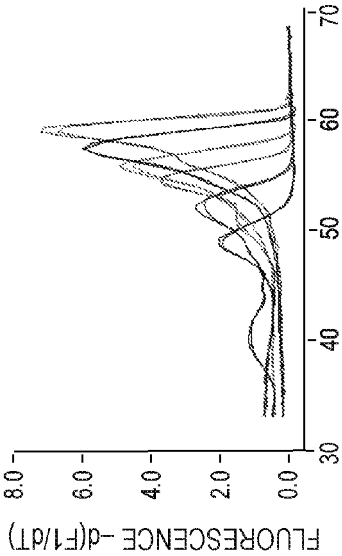

Detection of 5 and 7 repeat alleles would require the blocker oligonucleotide to be omitted from reactions. FIG. 6C illustrates the melt peaks generated with the FL1 probe in the absence of the B1 blocker. Assays possessing and lacking the blocker oligonucleotide may need to be performed in parallel to detect and identify the full range of D16S539 alleles.

TABLE 8

Probe Tms and ΔTms derived from FL1 probe hybridisation to oligonucleotide target sequences in the presence of the bimolecular blocker B1.

| Repeat combination | Tm & (ΔTm) |
|---|---|
| 8/8 | 40.0° C. |
| 9/9 | 47.5° C. |
| 10/10 | 51.8° C. |
| 11/11 | 54.0° C. |
| 12/12 | 57.0° C. |
| 8/9 | (7.5° C.) |
| 8/10 | (11.8° C.) |
| 8/11 | (14.0° C.) |
| 8/12 | (17.0° C.) |
| 9/10 | ( 4.3° C.) |
| 9/11 | (6.5° C.) |
| 9/12 | (9.5° C.) |
| 10/11 | (2.2° C.) |
| 10/12 | (5.2° C.) |
| 11/12 | (3.0° C.) |

EXAMPLE 6

Figure 7A:
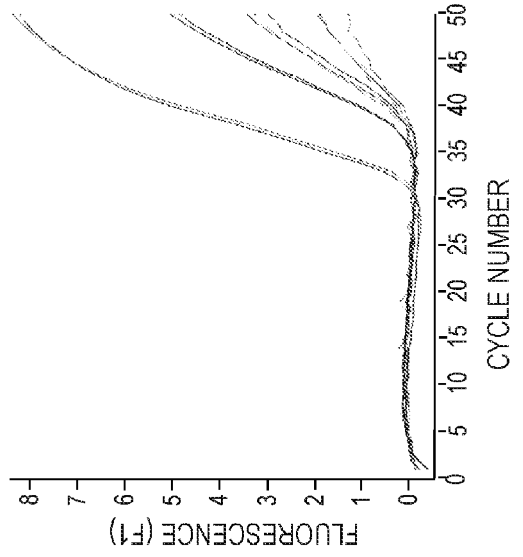
Figure 7B:
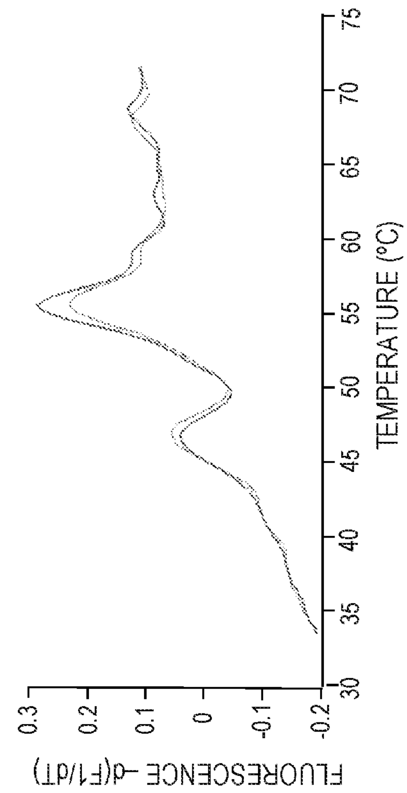

D16S539 target sequences were amplified from extracted DNA and directly from saliva samples using the primers STRF2 and STRR2. The relative concentrations of B1 blocker and FL1 probe oligonucleotides required optimisation to enable efficient target amplification whilst preventing full length probe hybridisation to targets possessing less than 15 repeats. Optimisation was achieved by analysing various concentrations and ratios of the blocking oligonucleotide and the probe oligonucleotide. A 6:1 ratio of blocking oligonucleotide to probe oligonucleotide was found to be useful. Insufficient B1 blocker caused the generation of a common peak at approximately 59° C. where the FL1 probe was not fully blocked allowing all 10 repeats to hybridise. Conversely, too much B1 blocker inhibited target amplification increasing the cycle number at which target was detected (FIG. 7A). The optimal concentration was found to be 37.5 nM of FL1 probe was employed along with 225 nM of B1 blocker. Analysis was performed with extracted DNA and saliva samples possessing 11/11, 10/11, 12/12, 10/13, 11/12, 13/13, 12/13 and 9/12 genotypes. The Tms of melt peaks corresponding to 9, 10, 11, 12 and 13 repeats were 47.0° C., 51.5° C., 53.5° C., 56.0° C. and 57.5° C. respectively. The sample of 9/12 genotype was the only melt profile that yielded two clear peaks (FIG. 7B). The 10 repeat peak was not efficiently detected with any sample. The 10 repeat peak had a reduced height compared with 11 and 13 repeats. The small ΔTm meant that the 10 repeat peak was hidden within the trace of the 11 and 13 repeat traces, such that not even a shoulder was visible. Increasing the ΔTm as shown with FL4 or attempting to standardise or improve peak heights of shorter repeats should overcome this problem. The 11/12 and 12/13 heterozygous samples generated single melt peaks with Tms intermediate between homozygous peaks (i.e. approximately 54.5° C. and 57.0° C. respectively). The use of HRM instruments should be useful to identify heterozygotes using these intermediate peak Tms.

The stability of the blocker was increased by incorporating the modified bases propynyl dU and propynyl dC and through the inclusion of a G-clamp and 5' trimethoxystilbene modification.

EXAMPLE 7

The STRF2 forward primer and B1 blocker sequences were combined into a single non-fluorescent oligonucleotide, using a hexaethylene glycol (HEG) as a linker and PCR blocker. The unimolecular primer/blocker oligonucleotide (BP1) comprised 5 repeats of d(TATC), a 10-mer anchor sequence to prevent slippage, HEG and the forward primer (table 9).

TABLE 9

STR analysis using a unimolecular blocker/primer and oligonucleotide probe, where P, 5, 6T and (HEG) represent 3' phosphate, fluorescein dT, octanediol and hexaethylene glycol respectively.

| Oligo | SEQ ID | Sequence |
|---|---|---|
| BP1 | 37 | TATCTATCTATCTATCTATCCACCTGTCTG(HEG)GAT CCCAAGCTCTTCCTCTT |
| FL1 | 38 | CAATGA5ATCTATC5ATCTATC5ATCTATC5ATCTATC 5ATCTATC6T |
| FL2 | 39 | CAATGATATC5ATCTATC5ATCTATCTATCTATCTATC 5ATCTATCP |
| FL3 | 40 | CAATGA5ATCTA5CTATC5ATCTA5CTATC5ATCTA5C TATC5ATCP |
| FL4 | 41 | CAATGATATC5ATCTA5CTATCTATCTATCTATCTATC 5ATCTATCP |
| FL5 | 42 | CAATGATATCTA5CTATCTA5CTATCTA5CTATCTA5C TATCTATC6T |

The advantage of this approach is that the blocker and target sequence become part of the same DNA strand following amplification. The unimolecular interaction between blocker and target is thermodynamically favoured over probe hybridisation. Furthermore, PCR efficiency is not comprised since the blocker cannot hybridise until after the target sequence is amplified (FIG. 8).

Figures 9A, 9B, 9C, 9D, 9E, 9F, 9G:
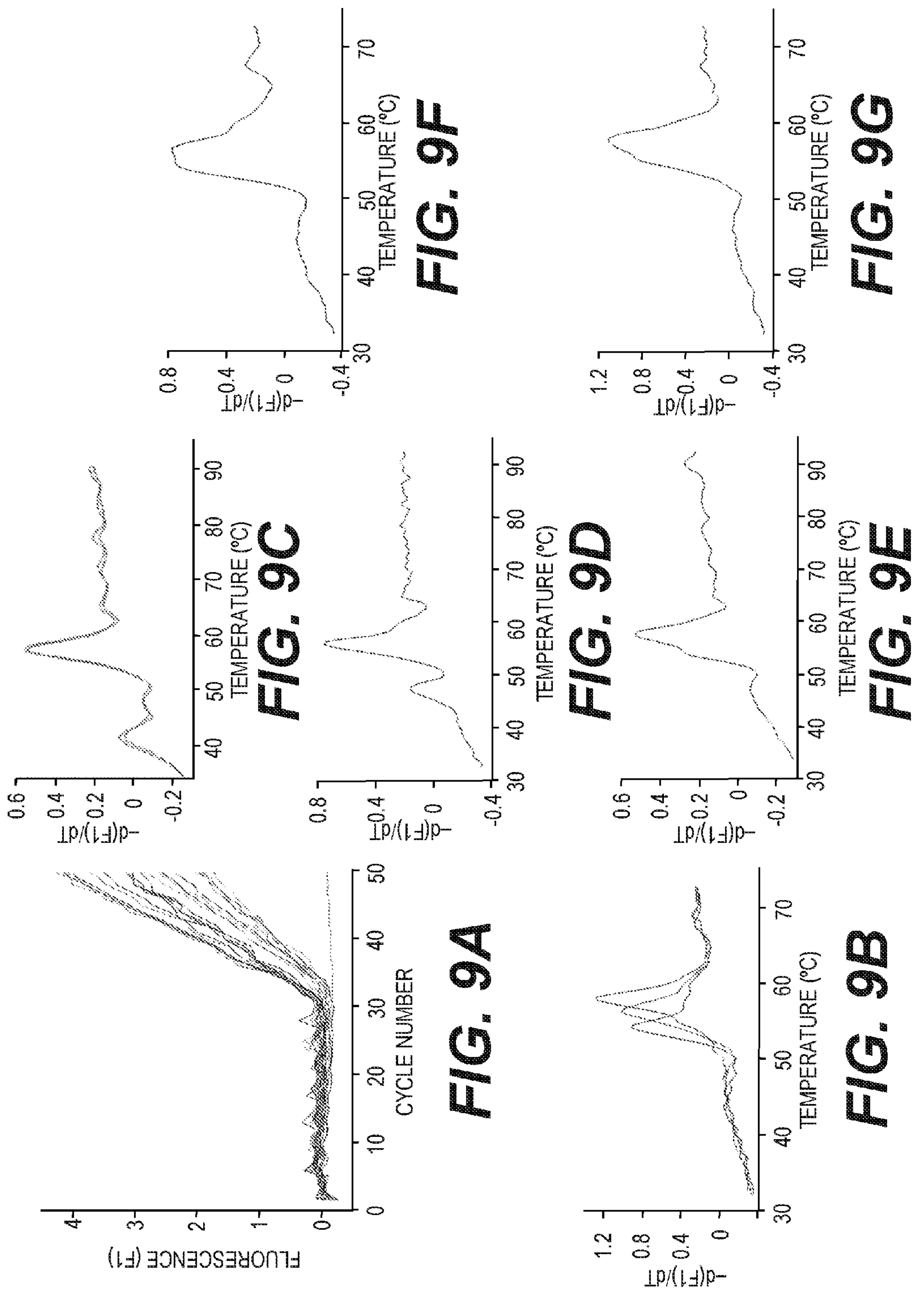

D16S539 target sequences were amplified from extracted DNA and directly from saliva samples using 0.5 μM of BP1 and 0.05 μM of STRR2 reverse primer. 50 nM of FL1 probe was employed to detect and identify target sequences amplified from samples of 11/11, 12/12, 13/13, 10/11, 10/13, 11/12, 12/13, 9/12, 11/13 and 8/13 genotype. Real-time LightCycler fluorescence data demonstrates that the efficiency of target amplification and detection is superior to that achieved using the bimolecular blocker approach (FIG. 9A). Target amplification was also performed using 384 well PCR plates followed by melt analysis using a LightTyper instrument. The Tms of melt peaks corresponding to 8, 9, 11, 12 and 13 repeats were 40.0° C., 46.0° C., 53.0° C., 55.5° C., 57.5° C. respectively (FIG. 9). The 10 repeat peak was not reliably detected in any of these samples because it was hidden within the traces of 11 and 13 repeats due to small ΔTm and reduced peak height. This may be overcome as discussed above. The samples of 8/13, and 9/12 genotype generated two clear melt peaks representing component alleles (FIG. 9C-D). Whereas heterozygous samples of 11/12, 12/13 genotype yielded a single melt peak Tm intermediate between the Tms of the homozygous alleles (i.e. approximately 54.5° C. and 56.0° C. respectively as presented in FIG. 9F-G).

Figure 10A:
Figure 10B:
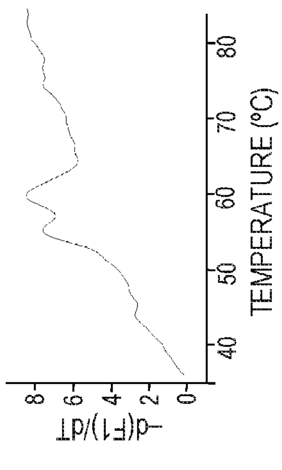
Figure 10C:
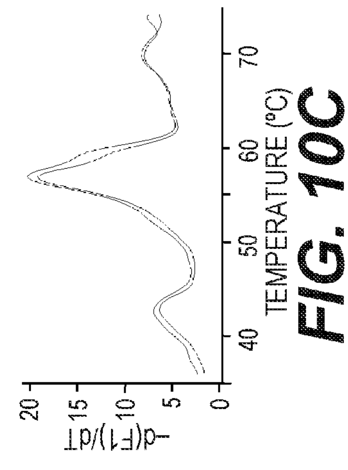
Figure 10D:
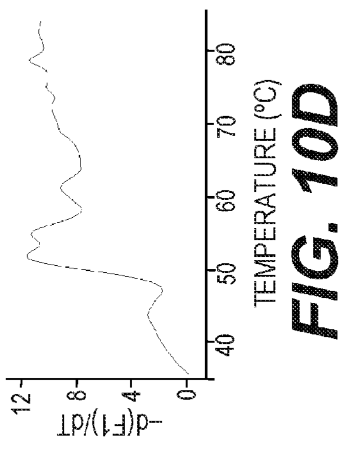
Figure 10E:
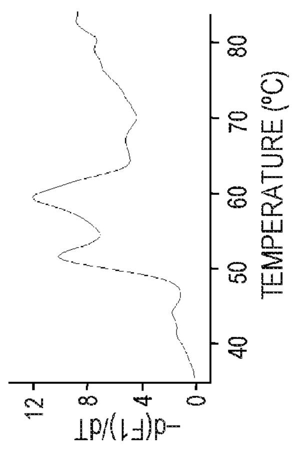

Analysis of DNA and saliva samples was repeated using BP1 and the oligonucleotide probes FL2, FL3, FL4 and FL5 which possessed different numbers of fluorophore-labelled bases and different spacings between fluorophores (Table 9). The Tms of melt peaks generated with amplified STR targets are presented in Table 10. Similar to the FL1 probe, FL3 and FL5 constructs were unable to reliably detect alleles possessing 10 repeats within heterozygous genotypes such as 10/11 and 10/13. The number and spacing of fluorescent-labelled bases influences the probe's signal-to-noise ratio and melt peak quality. Probes FL2 and FL4 only possess 3 fluorophore-labelled bases and were able to detect the 10 repeat allele in both 10/11 and 10/13 genotypes (FIG. 10D-E). The linear unmodified HYBSTR probe exhibited a Tm of 0.92° C. with 10 and 11 repeat alleles. A ΔTm of 3.5° C. was achieved using the unimolecular blocker BP1 and the FL4 HyBeacon.

TABLE 10

Tms of melt peaks generated with targets amplified from extracted DNA and unextracted saliva samples using the unimolecular BP1 blocker/primer.

| | Peak Tm | | | | |
|---|---|---|---|---|---|
| Repeats | FL1 | FL2 | FL3 | FL4 | FL5 |
| 8 | 40.0 | 42.5 | 39.0 | 41.0 | 42.5 |
| 9 | 46.0 | 48.0 | 44.5 | 47.5 | 47.0 |
| 10 | | 52.5 | | 52.5 | |
| 11 | 53.0 | 55.5 | 51.0 | 56.0 | 53.5 |
| 12 | 55.5 | 58.0 | 52.5 | 58.0 | 55.5 |
| 13 | 57.5 | 60.0 | 54.5 | 60.0 | 57.0 |

EXAMPLE 8

Figure 11A:
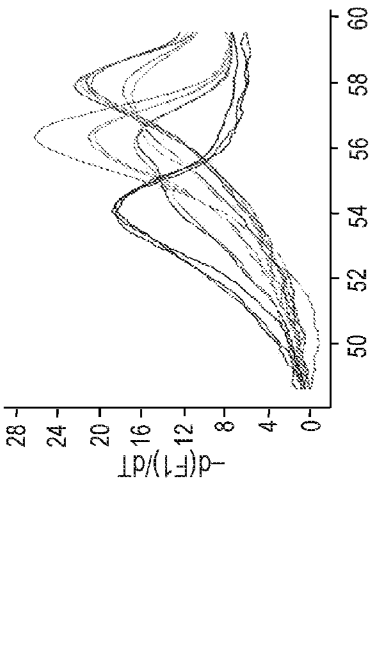
Figure 11B:
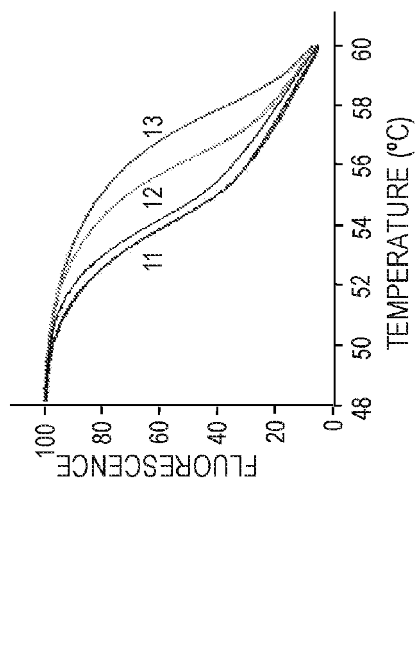
Figure 11C:
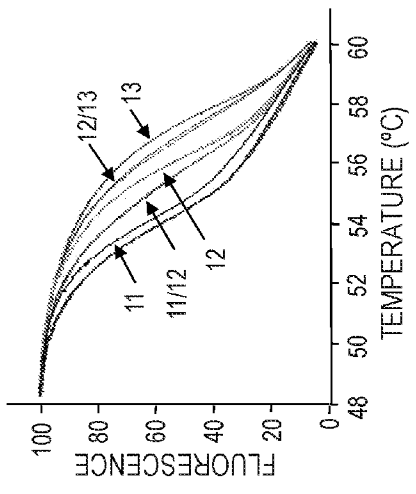
Figure 11D:
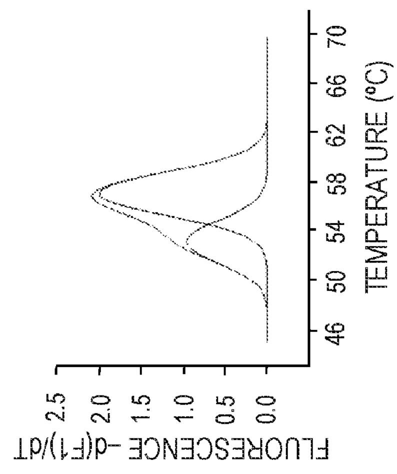

LightCycler capillaries containing amplified D16S539 targets, BP1 blocker and F6A oligonucleotide were reanalysed using a high resolution melting curve instrument (HR-1, Idaho Technology Inc, Utah, USA). The HR-1 could clearly discriminate melt peaks generated with 11, 12 and 13 repeat sequences (FIG. 11A). However, as described above, melt peaks could not be employed to identify heterozygous genotypes such as 11/12. The high resolution melting curve software did permit 9/12, 11/11, 11/12, 12/12, 12/13 and 13/13 genotypes to be clearly differentiated (FIG. 11B-C). High resolution analysis will not require ΔTms to exceed 3° C. to differentiate alleles of similar length. Furthermore, improved methods of data analysis will enable broad peaks and peak shoulders to be clearly separated into component alleles (FIG. 11D).

EXAMPLE 9

An alternative embodiment of the repeat blocking approach is to anchor the probe to the blocker rather than DNA sequence flanking the repetitive target. This approach increases the stability of probe hybridisation in the presence of the blocker, thereby increasing blocking efficiency. In a bimolecular format, the blocker oligonucleotide would comprise a defined number of sequence repeats, a suitable anchor sequence to prevent slippage and a GC rich clamp (FIG. 12). The clamp of the blocking oligonucleotide hybridises to a complementary clamp in the probe oligonucleotide. In a unimolecular format, the blocker repeats, anchor sequence and GC rich clamp would be attached to one of the PCR primers through a suitable spacer/PCR blocker (such as HEG). The fluorescent probes employed with these blockers would possess a GC rich sequence complementary to that of the blocker. The GC rich clamps will form a junction when blocker and probe oligonucleotides hybridise adjacently. The full length of the probe will be prevented from hybridising when target repeat number is less than 15 in the case of D16S539 (FIG. 12A-B).

Blocker oligonucleotides possessing 5 D16 repeats (5LSB1) and 7 repeats (7LSB2) were combined with fluorescent probes possessing 10 repeats (10SFL1) and 8 repeats (8SFL2) respectively. These junction probes and blockers (table 11) were hybridised to complementary target oligonucleotides possessing 8-15 repeats (Table 5) and analysed using a LightCycler instrument (FIG. 12C-D). Probe Tms are presented in Table 12. The ΔTms of 7LSB2 are enhanced due to the reduced length of the probe. Alleles comprising 9 repeats or less may be analysed in the absence of a blocker molecule.

TABLE 11

Sequences of junction probes and blockers, where 6 is pyrrolo-deoxycytosine (pdC), 5 is fluorescein dT, P is 3' phosphate and (HEG) is hexaethylene glycol.

| Oligo | SEQ ID | Sequence |
|---|---|---|
| 5LSB1 | 43 | GCGGCTATCTATCTATCTATCTATCCACCTGTCTGTCT GTCTGTA(HEG)GATCCCAAGCTCTTCCTCTT |
| 7LSB2 | 44 | GCGGCTATCTATCTATCTATCTATCTATCTATCCACCT GTCTGTCTGTCTGTATTGATCTAGGGP |
| 10SFL1 | 45 | TATCTATCTA56TATCTATCTA56TATCTAT65ATCTA TCGCCGCP |
| 8SFL2 | 46 | TATCTAT65ATCTAT65ATCTAT65ATCTATCGCCGCP |

TABLE 12

Tms of melt peaks generated with junction probes and blockers using oligonucleotide homologues.

| Repeats | Tm 5SBP1/10SFL1 | Tm 7LSB2/8SFL2 |
|---|---|---|
| 8 | 36.1° C. | |
| 9 | 44.6° C. | |
| 10 | 51.3° C. | 34.9° C. |
| 11 | 55.2° C. | 44.4° C. |
| 12 | 57.6° C. | 50.5° C. |
| 13 | 60.2° C. | 55.0° C. |
| 14 | 61.4° C. | 57.6° C. |
| 15 | 62.1° C. | 59.7° C. |

As a variation to the above, unimolecular blockers (PCR primers) may possess clamp portions of varying length and/or composition (A1, A2, A3 etc), and probe oligonucleotides may contain clamp portions complementary to the clamp portions on the PCR primers (A1', A2', A3' etc). In this way, for example, three or more probes may be included in PCR assays, and the sequence of the clamp portions may be used to modify peak Tms. This variation is shown diagrammatically in FIG. 15.

EXAMPLE 10

A second STR locus was investigated to demonstrate that detection and differentiation of repeating sequences by melting curve analysis is not unique to D16S539. The TH01 locus comprises repeats of $(AATG)_n$, with reported alleles possessing between 3 and 14 repeats (see FIG. 13 for gene sequence). TH01 sequences can comprise partial repeats, such as in the 9.3 allele $(AATG)_6ATG(AATG)_3$ (SEQ ID NO.: 47). Only the most common repeat alleles were considered when designing the proof-of-principle TH01 assay, where 99.5% of alleles comprise either 6 repeats (23%), 7 repeats (24.1%), 8 repeats (11.6%), 9 repeats (20%), 9.3 repeats (17.9%) or 10 repeats (2.9%). The additional challenge for the analysis of TH01 alleles was to discriminate not only the whole repeat alleles which differ in length by one or more multiples of 4 bases but also the 9.3 partial repeat and 10 whole repeat alleles that differ in length by only a single nucleotide.

The probe HYBTH01 was designed to detect and differentiate TH01 alleles. The probe comprised 6.1 repeats of AATG (Table 13) and a 5' anchor sequence of TGGFG. The probe was labelled with two fluorescein dT dyes, separated by 7 nucleotides, one of which was located within the anchor sequence. A bimolecular blocking strategy was employed as depicted in FIG. 6. The bimolecular blocker TH01_BL was designed to prevent the HYBTH01 probe from fully hybridising to target sequences when the number of repeats in the target allele was less than 10. The TH01_BL blocker comprised 3.3 repeats of AATG and a 3' anchor sequence of AGGGAAATAAGGG (SEQ ID NO 49) (Table 13).

TH01 target sequences were amplified from purified DNA samples and unpurified salivas using the primers TH01_F and TH01_R (Table 13). Asymmetric PCR was employed to enhance the efficiency of probe hybridisation to amplified target sequences, where TH01_F and TH01_R primer concentrations were 0.1 μM and 1 μM respectively. Probe and blocker oligonucleotides were employed at 75 nM and 375 nM concentrations respectively. A five times molar excess of blocker oligonucleotide was employed to prevent probe hybridisation to the common 3.1 AATG repeats shared by TH01 alleles. The blocker oligonucleotide limits the amount of target sequence available for probe hybridisation, effectively reducing the length of 6-10 repeat alleles to 2.1-6.1 repeats, thereby improving the ability to differentiate TH01 alleles on the basis of melting peak Tm.

TABLE 13

Analysis of TH01 repeats where 5 and P represent fluorescein dT and 3' phosphate respectively

| Oligo | SEQ ID | Sequence |
|---|---|---|
| HYBTH01 | 48 | TGG5GAATGAA5GAATGAATGAATGAATGAP |
| TH01_BL | 49 | ATGAATGAATGAATGAGGGAAATAAGGGP |
| TH01_F | 50 | GGCTTCCGAGTGCAGGTCA |
| TH01_R | 51 | GGTGATTCCCATTGGCCTG |

The combination of HYBTH01 probe and TH01_BL blocker enabled reliable detection and identification of amplified 8, 9, 9.3 and 10 repeat alleles, exhibiting melting peak Tms of approximately 53° C., 57° C., 60.5° C. and 61.5° C. respectively (FIG. 14). The melting temperatures of 6 and 7 repeat alleles were too low to enable reliable detection by this particular version of the probe structure which was designed to detect the more challenging longer repeat sequences within this locus. It is obvious that the same principle of the invention could be applied to the detection of 6 and 7 repeat alleles by decreasing the number of repeats in the blocker, increasing the number of repeats in the probe or increasing the Tm of the probe (either by increasing the length of the anchor sequence, through inclusion of DNA base analogues or cap phosphoramidites such as 5'-Trimethoxystilbene). Similarly, the TH01 assay is also expected to function efficiently in a unimolecular format using a long oligonucleotide comprising TH01_BL blocker and TH01_R primer sequences separated by a hexaethylene glycol (HEG) modification.

Conclusion

Repetitive sequences may be analysed using oligonucleotide probes, where the number of repeats is determined by target length and the proportion of probe hybridised. Long oligonucleotide probes in excess of 60 nucleotides are required to analyse short tandem repeats. The difference in probe Tm between long repeats is frequently small, preventing certain alleles from being reliably identified. ΔTm may be enhanced through probe destabilisation or by separating the repeating sequence into a non-fluorescent blocker and a fluorescent probe of reduced length. The various blocking strategies described here have enhanced probe ΔTms and the ability to differentiate D16S539 and TH01 alleles possessing large numbers of repeats. The examples of this invention may be extended to other STRs, including but not limited to D19S433 and D18S51.

EXAMPLE 11

Preventing Cross-Hybridisation of Probes and Blockers

D8S1179 and D3S1358 loci both comprise $(TCTA)_n$ repeating sequences. Probes and blockers may cross-hybridise preventing efficient target detection or causing erroneous results. Attaching blockers to primers (i.e. unimolecular blocking) prevents cross hybridisation. Attaching the probe to the unimolecular construct prevents detection of incorrect target alleles. An oligonucleotide spacer that separates blocker and probe components into two separate entities for the purpose of hybridisation stability is used to achieve this (see FIG. 16).

EXAMPLE 12

Including multiple blockers in a single tube uses a shift in melting peak Tms in order to detect additional repeat alleles. This is achieved using partial repeat (off-set) blockers which permit more or less of the probe (length/sequence) to hybridise.

Whilst D8S1179 alleles have been reported to comprise both TCTA and TCTG elements, TCTG repeats are restricted to alleles possessing 13 repeats and more and are located only in the second, third and fourth repeat positions (GenBank Accession No. AF216671). The variable TCTA and TCTG repeats were, therefore, located within blocking oligonucleotides, leaving only TCTA repeats available for probe hybridisation. D8S1179 loci have been reported with between 6 and 25 tetranucleotide repeats, however, only the most common repeat alleles were considered when designing the D8S1179 assay, where 99.9% of alleles comprise either 8 repeats (0.9%), 9 repeats (0.8%), 10 repeats (8.8%), 11 repeats (7.3%), 12 repeats (12.6%), 13 repeats (27.6%), 14 repeats (22.6%), 15 repeats (14.1%), 16 repeats (4.3%) and 17 repeats (0.9%).

The probe HYBD8 was designed to detect and differentiate D8S1179 alleles. The probe comprised 8 repeats of TCTA (Table 14) and a 3' anchor sequence of FTCCCCP. The probe was labelled with two fluorescein dT dyes, separated by 5 nucleotides, one of which was located within the anchor sequence. A bimolecular blocking strategy was employed as depicted in FIG. 6, using three blocker oligonucleotides to detect and differentiate the full range of common D8S1179 alleles. The bimolecular blockers D8BL5, D8BL8 and D8BL11 (Table 14) were designed to prevent the HYBD8 probe from fully hybridising to target sequences when the number of repeats in the target allele was less than 13, 16 and 19 respectively.

D8S1179 target sequences were amplified from purified DNA samples and unpurified salivas using the primers D8F and D8R (Table 14). Asymmetric PCR was employed to enhance the efficiency of probe hybridisation to amplified target sequences, where D8F and D8R primer concentrations were 0.1 μM and 1 μM respectively. Probe and blocker oligonucleotides were employed at 75 nM and 375 nM concentrations respectively. A five times molar excess of blocker oligonucleotide was employed to prevent full length probe hybridisation to inappropriate target repeats.

Melting curve analysis in the presence of D8BL5 permits reliable detection and identification of 8, 9 and 10 repeat alleles (Table 15). The D8BL8 blocker is used to detect 11, 12 and 13 repeat alleles and D8BL11 permits identification of 14, 15, 16 and 17 repeat alleles.

Hybridisation of the HYBD8 probe to 9 repeat. 12 repeat and 15 repeat target alleles results in melting peak Tms of 44.73° C., 44.4° C. and 44.4° C. when used in combination with D8BL5, D8BL8 and D8BL11 blockers respectively. Since D8BL5, D8BL8 and D8BL11 each leave three target repeats available for probe hybridisation, it is expected that 9, 12 and 15 repeat alleles would yield similar melting peak Tms. For this reason, the D8BL5, D8BL8 and D8BL11 blocker oligonucleotides may not be used together to simultaneously detect 9, 12 and 15 repeat alleles in a single tube.

TABLE 14

Analysis of D8S1179 repeats, where 5, P and X represent fluorescein dT, 3' phosphate and 3' amino C7 respectively

| Oligo | SEQ ID | Sequence |
|---|---|---|
| D8F | 52 | CGGCCTGGCAACTTATATGT |
| D8R | 53 | GCCTTAATTTATTTACCTATCCTGTAGA |
| HYBD8 | 54 | TCTATCTATCTATCTATCTATCTATC5ATCTA5TCCCCP |
| D8BL5 | 55 | GTATTTCATGTGTACATTCGTA$(TCTA)_5$X |
| D8BL8 | 56 | GTATTTCATGTGTACATTCGTA$(TCTA)_8$X |
| D8BL11 | 57 | GTATTTCATGTGTACATTCGTA$(TCTA)_{11}$X |
| D8BL7.2 | 58 | GTATTTCATGTGTACATTCGTA$(TCTA)_7$TCX |
| D8BL10.3 | 59 | GTATTTCATGTGTACATTCGTA$(TCTA)_{10}$TCTX |

Using blocker oligonucleotides with partial repeats will cause melting peak Tms to be shifted ("off-set"), increasing the number of STR alleles that may be detected simultaneously. Partial repeat blockers comprising 7.2 (i.e. $(TCTA)_7TC$) and 10.3 (i.e. $(TCTA)_{10}TCT$) repeats were evaluated with amplified targets possessing between 11 and 17 repeats. The reduction of blocker length, relative to D8BL8 and D8BL11, permits more of the probe to hybridise causing an increase in melting peak Tms (Table 15). For example, in the presence of the D8BL7.2 blocker, probe hybridisation to a 12 repeat target yields a melting peak Tm of 46.88° C., such that the D8BL5 and D8BL7.2 blockers may be used to simultaneously detect 9 and 12 repeat alleles (FIG. 18). FIG. 19 illustrates simultaneous detection of 11 and 15 repeat alleles using the D8BL7.2 and D8BL10.3 blockers in a single tube.

TABLE 15

| Blocker | Target | Tm | Offset blocker | Target | Predicted Tm | Tm | ΔTm |
|---|---|---|---|---|---|---|---|
| D8BL5 | 8 | 37.12 | | | | | |
| D8BL5 | 9 | 44.73 | | | | | |
| D8BL5 | 10 | 49.36 | | | | | |
| D8BL5 | 11 | 52.67 | | | | | |
| D8BL8 | 11 | 37.12 | D8BL7.2 | 11 | 40.76 | 40.43 | 3.31 |
| D8BL8 | 12 | 44.4 | D8BL7.2 | 12 | 46.88 | 46.38 | 1.98 |
| D8BL8 | 13 | 49.36 | D8BL7.2 | 13 | 51.02 | 50.68 | 1.32 |
| D8BL8 | 14 | 52.67 | D8BL7.2 | 14 | 53.83 | 53.66 | 0.99 |
| D8BL11 | 14 | 36.79 | D8BL10.3 | 14 | 39.33 | 39.1 | 2.31 |
| D8BL11 | 15 | 44.4 | D8BL10.3 | 15 | 46.27 | 45.72 | 1.32 |
| D8BL11 | 16 | | D8BL10.3 | 16 | 50.89 | | |
| D8BL11 | 17 | 52.67 | D8BL10.3 | 17 | 53.44 | 53.66 | 0.99 |

Tables of Suitable Dyes

TABLE 14

General fluorescent dyes for oligonucleotide labelling

| Dye | λ-excit | λ-emiss | colour |
|---|---|---|---|
| Fluorescein | 494 nm | 525 nm | Green |
| Tetrachloro Fluorescein TET | 521 nm | 536 nm | Orange |
| JOE | 525 nm | 555 nm | Green |
| Yakima Yellow | 530 nm | 549 nm | Yellow |
| Hexachloro Fluorescein HEX | 535 nm | 556 nm | Pink |
| Cy3 (also Quasar 570) | 546 nm | 563 nm | Red |
| 5-TAMRA | 541 nm | 568 nm | Rose |

TABLE 14-continued

| General fluorescent dyes for oligonucleotide labelling | | | |
|---|---|---|---|
| Dye | λ-excit | λ-emiss | colour |
| 6-TAMRA | 547 nm | 573 nm | Rose |
| Redmond Red | 579 nm | 595 nm | Red |
| Cy3.5 | 588 nm | 604 nm | Purple |
| ROX | 585 nm | 610 nm | Red |
| Pulsar 650 | 490 nm | 650 nm | purple |
| Cy5 (also Quasar 670) | 646 nm | 662 nm | Violet |
| Cy5.5 | 683 nm | 707 nm | Dark Blue |

TABLE 15

| Alexa dyes (Invitrogen) | | |
|---|---|---|
| Alexa Dye | λ-excit | λ-emiss |
| Alexafluor 350 | 350 nm | 442 nm |
| Alexafluor 405 | 405 nm | 421 nm |
| Alexafluor 430 | 430 nm | 540 nm |
| Alexafluor 488 | 488 nm | 518 nm |
| Alexafluor 500 | 502 nm | 524 nm |
| Alexafluor 514 | 518 nm | 542 nm |
| Alexafluor 532 | 534 nm | 553 nm |
| Alexafluor 546 | 546 nm | 565 nm |
| Alexafluor 555 | 552 nm | 567 nm |
| Alexafluor 568 | 578 nm | 603 nm |
| Alexafluor 594 | 591 nm | 618 nm |
| Alexafluor 610 | 612 nm | 628 nm |
| Alexafluor 633 | 633 nm | 650 nm |
| Alexafluor 647 | 647 nm | 662 nm |
| Alexafluor 660 | 663 nm | 690 nm |
| Alexafluor 680 | 679 nm | 702 nm |
| Alexafluor 700 | 696 nm | 719 nm |
| Alexafluor 750 | 752 nm | 779 nm |

TABLE 16

| ATTO dyes (ATTO-TEC GmbH) | | |
|---|---|---|
| ATTO Dye | λ-excit | λ-emiss |
| ATTO 425 | 436 nm | 484 nm |
| ATTO 465 | 453 nm | 508 nm |
| ATTO 488 | 501 nm | 523 nm |
| ATTO 495 | 495 nm | 527 nm |
| ATTO 520 | 525 nm | 545 nm |
| ATTO 532 | 532 nm | 553 nm |
| ATTO 550 | 554 nm | 576 nm |
| ATTO 565 | 563 nm | 592 nm |
| ATTO 590 | 594 nm | 624 nm |
| ATTO 610 | 615 nm | 634 nm |
| ATTO 620 | 619 nm | 643 nm |
| ATTO 635 | 635 nm | 659 nm |
| ATTO 647 | 645 nm | 669 nm |
| ATTO 655 | 633 nm | 684 nm |
| ATTO 680 | 680 nm | 700 nm |
| ATTO 700 | 700 nm | 719 nm |

TABLE 17

| Dyomics dyes (Dyomics GmbH) | | |
|---|---|---|
| Dyomics Dye | λ-excit | λ-emiss |
| DY415 | 418 nm | 465 nm |
| DY495 | 495 nm | 520 nm |
| DY505 | 505 nm | 530 nm |
| DY547 | 557 nm | 574 nm |
| DY548/549 | 558 nm | 572 nm |
| DY550 | 553 nm | 578 nm |
| DY555 | 555 nm | 580 nm |

TABLE 17-continued

| Dyomics dyes (Dyomics GmbH) | | |
|---|---|---|
| Dyomics Dye | λ-excit | λ-emiss |
| DY556 | 548 nm | 573 nm |
| DY560 | 559 nm | 578 nm |
| DY590 | 580 nm | 599 nm |
| DY610 | 609 nm | 629 nm |
| DY615 | 621 nm | 641 nm |
| DY630 | 636 nm | 657 nm |
| DY631 | 637 nm | 658 nm |
| DY632/633/634 | 637 nm | 657 nm |
| DY635 | 647 nm | 671 nm |
| DY636 | 645 nm | 671 nm |
| DY647 | 652 nm | 673 nm |
| DY648 | 653 nm | 674 nm |
| DY650 | 653 nm | 674 nm |
| DY651 | 653 nm | 678 nm |
| DY652 | 654 nm | 675 nm |
| DY675/676 | 674 nm | 699 nm |
| DY677 | 673 nm | 694 nm |
| DY680/682 | 690 nm | 709 nm |
| DY700 | 702 nm | 723 nm |
| DY701 | 706 nm | 731 nm |
| DY730 | 734 nm | 750 nm |
| DY731/734 | 736 nm | 759 nm |
| DY732 | 736 nm | 759 nm |
| DY750 | 747 nm | 776 nm |
| DY751 | 751 nm | 779 nm |
| DY752 | 748 nm | 772 nm |
| DY776 | 771 nm | 801 nm |
| DY781 | 783 nm | 800 nm |
| DY782 | 782 nm | 800 nm |

TABLE 18

| Dyomics Megastokes dyes (Dyomics GmbH). All can be excited at 488 nm | | |
|---|---|---|
| Dyomics Dye | λ-excit | λ-emiss |
| DY475XL | 493 nm | 514 nm |
| DY480XL | 500 nm | 630 nm |
| DY485XL | 485 nm | 560 nm |
| DY500XL | 505 nm | 555 nm |
| DY510XL | 509 nm | 590 nm |
| DY600XL | 603 nm | 634 nm |
| DY520XL | 520 nm | 664 nm |

TABLE 19

| Hilyte dyes (Cambridge Bioscience) | | |
|---|---|---|
| Dye | λ-excit | λ-emiss |
| Hilyte Fluor 488 | 502 nm | 527 nm |
| Hilyte Fluor 555 | 552 nm | 569 nm |
| Hilyte Fluor 647 | 649 nm | 674 nm |
| Hilyte Fluor 680 | 678 nm | 699 nm |

TABLE 20

| Low excitation wavelength (UV) fluorophores | | |
|---|---|---|
| Derivative | Abs * | Em * |
| Alexa Fluor 350 | 346 | 442 |
| Alexa Fluor 405 | 402 | 412 |
| Anilinonaphthalene | 326 | 462 |
| Bimane | 375 | 456 |
| Dansyl | 328 | 563 |
| Dapoxyl | 374 | 572 |
| Dibromobimane | 394 | 490 |

TABLE 20-continued

| Low excitation wavelength (UV) fluorophores | | |
|---|---|---|
| Derivative | Abs * | Em * |
| Diethylaminocoumarin | 384 | 470 |
| Dimethylaminocoumarin | 376 | 465 |
| Dimethylaminonaphthalene | 391 | 500 |
| Monobromobimane | 394 | 490 |
| Monochlorobimane | 394 | 490 |
| Naphthalene | 336 | 490 |
| Pyrene | 339 | 384 |
| Stilbene | 329 | 408 |

TABLE 21

Common STRs

| Locus Designation | Chromosome Location | Common Sequence Motif | Reported Alleles |
|---|---|---|---|
| D3S1358 | 3p | TCTA(TCTG)$_{1-3}$(TCTA)$_n$ (SEQ ID NOs.: 60-62) | 9, 10, 11, 12, 13, 14, 15, 15.2, 16, 16.2, 17, 17.1, 18, 19, 20 |
| vWA | 12p12-pter | TCTA(TCTG)$_{3-4}$(TCTA)$_n$ (SEQ ID NOs.: 63-64) | 10, 11, 12, 13, 14, 15, 15.2, 16, 17, 18, 18.2, 18.2, 19, 19.2, 20, 21, 22, 23, 24, 25 |
| D16S539 | 16q24-qter | (AGAT)$_n$ | 5, 8, 9, 10, 11, 12, 13, 14, 15 |
| D2S1338 | 2q35-37.1 | (TGCC)$_n$(TTCC)$_n$ (SEQ ID NO.: 65) | 15, 16, 17, 18, 19, 20, 21, 22, 23, 24, 25, 26, 27, 28 |
| Amelogenin | X: p22.1-22.3 Y: p11.2 | — | X, Y |
| D8S1179[a] | 8 | (TCTR)$_n$[b] | 6, 7, 8, 9, 10, 11, 12, 13, 14, 15, 16, 17, 18, 19, 20.2, 21.2 |
| D21S11 | 21q11.2-q21 | (TCTA)$_n$(TCTG)$_n$[(TCTA)$_3$TA(TCTA)$_3$TCA (SEQ ID NO.: 66) | 24, 24.2, 25, 25.2, 26, 26.1, 27, 27.2, 27.3, |
| | | (TCTA)$_2$TCCA TA](TCTA)$_n$ (SEQ ID NO.: 67) | 28, 28.2, 28.3, 29, 29.1, 29.2, 29.3, 30, 30.1, 30.2, 31, 31.1, 31.2, 31.3, 32, 32.1 32.2, 32.2, 33, 33.3, 34, 34.2, 34.3, 35, 35.2, 35.3, 36, 36.2, 36.3, 37, 37.2, 38, 38.2 |
| D18S51 | 18q21.3 | (AGAA)$_n$ | 7, 8, 9, 9.2, 10, 10.2, 11, 12, 12.2, 13, 13.2, 14, 14.2, 15, 15.1, 15.2, 15.3, 16, 16.2, 16.3, 17, 17.1, 17.3, 18, 18.1, 18.2, 19, 19.2, 20, 20.1, 20.2, 21, 21.2, 22, 23, 23.1, 24, 25, 26, 27 |
| D19S433 | 19q12-13.1 | (AAGG)(AAAG)(AAGG)(TAGG) (SEQ ID NO.: 68) | 9, 10, 11, 12, 12.2, 13, 13.2, 14, 14.2, 15, |
| | | (AAGG)$_n$ | 15.2, 16, 16.2, 17, 17.2, 18, 18.2, 19 |
| TH01 | 11p15.5 | (AATG)$_n$ | 3, 4, 5, 5.3, 6, 6.1, 6.3, 7, 7.1, 7.3, 8, 8.3, 9, 9.3, 10, 10.3, 11, 13.3, 14 |
| FGA | 4q28 | (TTTC)$_3$TTTT TTCT (CTTT)$_n$ CTCC (SEQ ID NO.: 69) | 12.2, 13, 15, 16, 16.1, 16.2, 17, 17.1, 17.2, |

TABLE 21-continued

| Common STRs | | | |
|---|---|---|---|
| Locus Designation | Chromosome Location | Common Sequence Motif | Reported Alleles |
| | | $(TTCC)_2$ | 18, 18.1, 18.2, 19, 19.1, 19.2, 19.3, 20, 20.1, 20.2, 20.3, 21, 21.2, 22, 22.1, 22.2, 22.3, 23, 23.2, 23.3, 24, 24.1, 24.2, 24.3, 25, 25.1, 25.2, 25.3, 26, 26.1, 26.2, 27, 27.1, 27.3, 28, 28.1, 29, 29.2, 30, 30.2, 31, 31.2, 32, 32.2, 33.2, 35.2, 42.2, 43.2, 44.2, 45.2, 46.2, 47.2, 48.2, 49.2, 50.2, 51.2 |

[a]In some literature references, this locus is designated as D6S502.
[b]R can represent either an A or G nucleotide.

STRs in Common Usage

The SGM+ loci used in the UK are:

D3S1358, VWA, D16S539, D2S1338, D8S1179, D21S11, D18S51, D19S433, TH01 FGA.

The 13 CODIS loci used in the US are:

CSF1PO, FGA, TH01, TPOX, VWA, D3S1358, D5S818, D7S820, D8S1179, D13S317, D16S539, D18S51, and D21S11

A core set of Y-chromosome STR (Y-STR) loci is widely used in laboratories worldwide for human identity testing and genetic genealogy. The minimal haplotype loci (MHL) were selected in the late 1990s from a small set of available Y-STRs. The MHL include DYS19, DYS389I, DYS389II, DYS390, DYS391, DYS392, DYS393, and the polymorphic, multi-copy marker DYS385. In 2003, the Y-chromosome subcommittee of the Scientific Working Group on DNA Analysis Methods (SWGDAM) recommended two additional Y-STRs named DYS438 and DYS439.

REFERENCES

Bart-Delabesse, E., Sarfati, J., Debeaupuis, J. P., van Leeuwen, W., van Belkum, A., Bretagne, S., Latge, J. P. (2001). Comparison of restriction fragment length polymorphism, microsatellite length polymorphism, and random amplification of polymorphic DNA analyses for fingerprinting *Aspergillus fumigatus* isolates. *J. Clin. Microbiol.* 39:2683-6.

Belgrader, P., Smith, J. K., Weedn, V. W., Northrup, M. A. (1998). Rapid PCR for identity testing using a battery-powered miniature thermal cycler. *J Forensic Sci.* 43(2): 315-9.

Bell, G. I., Selby, M. J., Rutter, W. J. (1982). The highly polymorphic region near the human insulin gene is composed of simple tandemly repeating sequences. *Nature* 295:31-5.

Brondani, C., Borba, T. C., Rangel, P. H. N., and Brondani, R. P. V. (1998). Determination of genetic variability of traditional varieties of Brazilian rice using microsatellite markers. *Genetics* 149: 2007-2023.

Brondani, C., Rangel, P. H., Borba, T. C., Brondani, R. P. (2003). Transferability of microsatellite and sequence tagged site markers in *Oryza* species. *Hereditas.* 138(3): 187-92.

Carrier. L, Hengstenberg. C, Beckmann. J, S, Guicheney. P., Dufour, C., Bercovici, J., Dausse, E., Berebbi-Bertrand, I., Wisnewsky, C., Pulvenis, D. et al (1993). Mapping of a novel gene for familial hypertrophic cardiomyopathy to chromosome 11. *Nat. Genet.* 4:311-3.

Frayling, I. M. (1999). Microsatellite instability. *Gut* 45: 1-4.

Goedecke, N., McKenna, B., El-Difrawy, S., Carey, L., Matsudaira, P., Ehrlich D. (2004). A high-performance multilane microdevice system designed for the DNA forensics laboratory. *Electrophoresis* 25:1678-86.

Ionov, Y., Peinado, M. A., Malkhosyan, S., Shibata D., and Perucho. M. (1993). Ubiquitous somatic mutations in simple repeated sequences reveal a new mechanism for colonic carcinogenesis. *Nature* 363: 558-561.

Jeffreys A J, Wilson V, Thein S L. (1985a). *Nature* 314:67-73. Hypervariable 'minisatellite' regions in human DNA.

Jeffreys A J, Wilson V, Thein S L. *Nature*. (1985b). 316:76-9. Individual-specific 'fingerprints' of human DNA.

Lagally, E. T., Emrich, C. A., Mathies, R. A. (2001). Fully integrated PCR-capillary electrophoresis microsystem for DNA analysis. *Lab Chip* 1:102-7.

Loeb, L. A. (1994). Microsatellite instability: marker of a mutator phenotype in cancer. *Cancer Res.* 54: 5059-5063.

Matute, D. R., Sepulveda, V. E., Quesada, L. M., Goldman, G. H., Taylor, J. W., Restrepo, A., McEwen, J. G. (2006). Microsatellite analysis of three phylogenetic species of *Paracoccidioides brasiliensis*. *J. Clin. Microbiol.* 44:2153-7.

McCormick, R. M., Nelson, R. J., Alonso-Amigo, M. G., Benvegnu, D. J., Hooper, H. H. (1997). Microchannel electrophoretic separations of DNA in injection-molded plastic substrates. *Anal. Chem.* 69:2626-30.

McCouch, S. R., Teytelman, L., Xu, Y., Lobos K. B., Clare K., Walton, M., Fu, B., Maghirang R., Li, Z., Xing, Y., Zhang, Q., Kono, I., Yano M., Fjellstrom, R., DeClerk, G., Schneider, D., Cartinhour, S., Ware, D. and Stein, L. (2002). Development and mapping of 2240 new SSR markers for rice (*Oryza sativa* L). *DNA Res.* 9:199-207.

Radtkey, R., Feng, L., Muralhidar, M., Duhon, M., Canter, D., DiPierro, D., Fallon, S., Tu, E., McElfresh, K., Nerenberg, M., Sosnowski, R. (2000). Rapid, high fidelity analysis of simple sequence repeats on an electronically active DNA microchip. *Nucleic Acids Res.* 28: E17.

Roder., M. S., Korzun, V., Wendehake, K., Plaschke, J., Tixier, M. H., Leroy, P., Ganal, M. W. (1998). *Genetics* 149:2007-23. A microsatellite map of wheat.

Schmalzing, D., Koutny, L., Chisholm, D., Adourian, A., Matsudaira, P., Ehrlich, D. (1999). Two-color multiplexed analysis of eight short tandem repeat loci with an electrophoretic microdevice. *Anal. Biochem.* 270:148-52.

Shi, Y., Simpson, P. C., Scherer, J. R., Wexler, D., Skibola, C., Smith, M. T., Mathies, R. A. (1999). Radial capillary array electrophoresis microplate and scanner for high-performance nucleic acid analysis. *Anal Chem.* 71:5354-61.

Sinden, R. R. (1999). Biological implications of the DNA structures associated with disease-causing triplet repeats. *Am. J. Hum. Genet.* 64:346-53.

Thierfelder, L., MacRae, C., Watkins, H., Tomfohrde, J., Williams, M., McKenna., W., Bohm K., Noeske, G., Schlepper, M., Bowcock, A. et al (1993). A familial hypertrophic cardiomyopathy locus maps to chromosome 15q2. *Proc. Natl. Acad. Sci. USA.* 90:6270-4.

Watkins, H., MacRae, C., Thierfelder, L., Chou, Y. H., Frenneaux, M., McKenna, W., Seidman, J. G., Seidman, C. E. (1993). A disease locus for familial hypertrophic cardiomyopathy maps to chromosome 1q3. *Nat. Genet.* 3:333-7.

Weissenbach, J., Gyapay, G., Dib, C., Vignal, A., Morissette, J., Millasseau, P., Vaysseix, G., Lathrop, M. (1992). A second-generation linkage map of the human genome. *Nature* 359:794-801.

Westin, L., Xu, X., Miller, C., Wang, L., Edman, C. F., Nerenberg, M. (2000). Anchored multiplex amplification on a microelectronic chip array. *Nature Biotechnol.* 18:199-204.

Wooley, A. T. and Mathies, R. A. (1994). *Proc. Natl. Acad. Sci. USA* 91:11348-11352.

---

The invention claimed is:

1. A method for determining the number of specific short tandem repeats at a specific polymorphic locus of a target polynucleotide, wherein the specific polymorphic locus is known to have multiple known alleles of known sequence which vary by the number of specific short tandem repeats, the method comprising (a) providing a sample containing a single stranded target polynucleotide, wherein the single stranded target polynucleotide comprises single-stranded specific short tandem repeats at the specific polymorphic locus of the target polynucleotide, wherein the number of specific short tandem repeats is within a known range, and wherein the arrangements of the specific short tandem repeats are known, (a1) hybridising one or more different blocking oligonucleotides to at least one but not all of the single-stranded specific short tandem repeats of the target polynucleotide so that the one or more different blocking oligonucleotides block any variable region within the specific polymorphic locus of the single stranded target polynucleotide and so that one or more of the specific short tandem repeats remain in single stranded form after hybridizing the one or more different blocking oligonucleotides to the target polynucleotide, wherein the sequences of the one or more different blocking oligonucleotides are known and are complementary with the target polynucleotide, (b) hybridising a labelled probe oligonucleotide to one or more of the specific short tandem repeats of the target polynucleotide which remain in single stranded form after step (a1), wherein the labelled probe oligonucleotide comprises identical repeated sequences complementary to the one or more specific short tandem repeats of the target polynucleotide which remain in single stranded form after step (a1) so that all of the single-stranded specific short tandem repeats of the target polynucleotide are fully occupied by one end of the labelled probe oligonucleotide and the one or more different blocking oligonucleotides, wherein the one end of the labelled probe oligonucleotide hybridises with the target polynucleotide to provide a stable hybrid whose melting peak temperature depends on the exact sequence of the target polynucleotide and the number of specific short tandem repeats of the target polynucleotide which remain in single stranded form after step (a1) while the other end of the labelled probe oligonucleotide does not hybridise with the target polynucleotide, and there is no gap between the labelled probe oligonucleotide and its adjacent blocking oligonucleotide of the different blocking oligonucleotides on the target polynucleotide after hybridising the labelled probe oligonucleotide to the target polynucleotide, and (c) determining the number of the specific short tandem repeats at the polymorphic locus of the target polynucleotide by comparing the melting peak temperature ($T_m$) of a hybrid formed by the target polynucleotide and the labelled probe oligonucleotide in the presence of the one or more different blocking oligonucleotides with $T_m$ information generated from a method using steps (a), (a1) and (b) above using different target polynucleotides consisting of known numbers of the specific short tandem repeats and identical other properties of the target polynucleotide, the one or more different blocking oligonucleotides and the labelled probe oligonucleotide.

2. The method according to claim 1 wherein the target polynucleotide is DNA.

3. The method according to claim 1 wherein step (c) further comprises melting curve analysis.

4. The method according to claim 3 wherein the one or more different blocking oligonucleotides are fully complementary to the at least one of the specific short tandem repeats in the target polynucleotide.

5. The method according to claim 1 wherein, in step (b), the probe oligonucleotide is complementary to at least two of the specific short tandem repeats in the target polynucleotide.

6. The method according to claim 1 wherein the probe oligonucleotide is complementary to at least 8 nucleotides in the specific short tandem repeats of the target polynucleotide.

7. The method according to claim 1 wherein, in step (a1), the one or more different blocking oligonucleotides hybridise to at least two of the specific short tandem repeats in the target polynucleotide.

8. The method according to claim 1 wherein, in step (a1), two or more of the specific short tandem repeats remain in single stranded form after the hybridisation of the one or more different blocking oligonucleotides to the target polynucleotide.

9. The method according to claim 1 wherein, in step (a1), the one or more different blocking oligonucleotides are two or more blocking oligonucleotides.

10. The method according to claim 1 wherein the sample in step (a) is produced during or after an amplification reaction.

11. The method according to claim 10 wherein the amplification reaction is a polymerase chain reaction (PCR).

12. The method according to claim 1 wherein the labelled probe oligonucleotide is fluorescently labelled.

13. The method according to claim 1 wherein the labelled probe oligonucleotide is fully complementary to the at least one of the specific short tandem repeats in the target polynucleotide.

14. The method according to claim 1 wherein the labelled probe oligonucleotide contains an anchor portion which is complementary to a region in the target polynucleotide which flanks the specific short tandem repeats.

15. The method according to claim 1 wherein, when the one or more different blocking oligonucleotides is one blocking oligonucleotide, the blocking oligonucleotide contains an anchor portion which is complementary to the region which flanks the specific short tandem repeats.

16. The method according to claim 15 wherein the labelled probe oligonucleotide contains an anchor portion which is complementary to a region in the target polynucleotide which flanks the specific short tandem repeats and which is not complementary to the anchor portion of the blocking oligonucleotide.

17. The method according to claim 1 wherein steps (a) and (a1) are carried out simultaneously.

18. The method according to claim 17 wherein the target polynucleotide is generated by a polymerase chain reaction using a primer, and the primer comprises one of the different blocking oligonucleotides.

19. The method according to claim 18 wherein the primer comprises at its 3' end a portion which is complementary to a region in the target polynucleotide which is 3' of one of the specific short tandem repeats and at its 5' end a portion which is complementary to at least one of the specific short tandem repeats.

20. The method according to claim 19 wherein the primer comprises, from 3' to 5', (i) the portion which is complementary to a region in the target polynucleotide which is 3' of one of the short tandem repeats, (ii) optionally, a spacer portion, (iii) an anchor portion which is complementary to a region which flanks the short tandem repeat in the target polynucleotide, and (iv) the portion which is complementary to at least one of the specific short tandem repeats.

21. The method according to claim 18 wherein the primer further comprises the probe oligonucleotide.

22. The method according to claim 20 wherein the primer further comprises (v) a spacer portion and (vi) the probe oligonucleotide.

23. The method according to claim 1 wherein the target polynucleotide is human genomic DNA.

* * * * *